US007666624B2

(12) United States Patent
Brennan

(10) Patent No.: US 7,666,624 B2
(45) **Date of Patent: *Feb. 23, 2010**

(54) MODIFIED PLANT VIRUSES AND METHODS OF USE THEREOF

(75) Inventor: Frank R. Brennan, Reading (GB)

(73) Assignee: Dow Global Technologies Inc., Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/880,195

(22) Filed: Jul. 20, 2007

(65) Prior Publication Data

US 2008/0124358 A1 May 29, 2008

Related U.S. Application Data

(63) Continuation of application No. 10/110,683, filed as application No. PCT/US00/28443 on Oct. 13, 2000, now Pat. No. 7,267,963.

(30) Foreign Application Priority Data

Oct. 14, 1999 (GB) ................................ 9924351.1

(51) Int. Cl.
*C12N 15/00* (2006.01)
*C12N 15/82* (2006.01)
*C12N 5/14* (2006.01)
*A16K 35/00* (2006.01)

(52) U.S. Cl. .................. 435/69.1; 435/93.1; 435/320.1; 435/91.1; 435/468; 435/410; 424/93.2; 424/185.1; 424/199.1; 424/193.1; 514/54; 514/44

(58) Field of Classification Search ................ 435/96.1, 435/91.4
See application file for complete search history.

(56) References Cited

U.S. PATENT DOCUMENTS

| | | | |
|---|---|---|---|
| 3,919,411 | A | 11/1975 | Glass et al. |
| 4,029,766 | A | 6/1977 | Helting |
| 4,619,896 | A | 10/1986 | Shattock et al. |
| 4,639,512 | A | 1/1987 | Audibert et al. |
| 4,702,909 | A | 10/1987 | Villarejos et al. |
| 4,795,803 | A | 1/1989 | Lindberg et al. |
| 4,837,306 | A | 6/1989 | Ling et al. |
| 4,839,275 | A | 6/1989 | Weil |
| 4,839,277 | A | 6/1989 | Sugahara et al. |
| 4,950,480 | A | 8/1990 | Barber et al. |
| 4,956,278 | A | 9/1990 | Hari et al. |
| 5,049,655 | A | 9/1991 | Vaughan et al. |
| 5,096,906 | A | 3/1992 | Mandell et al. |
| 5,151,511 | A | 9/1992 | Souza et al. |
| 5,194,254 | A | 3/1993 | Barber et al. |
| 5,200,393 | A | 4/1993 | Weiner et al. |
| 5,212,085 | A | 5/1993 | Wands et al. |
| 5,232,690 | A | 8/1993 | Bernhardt et al. |
| 5,268,265 | A | 12/1993 | Montagnier et al. |
| 5,314,996 | A | 5/1994 | Wright, Jr. |
| 5,342,770 | A | 8/1994 | Yamasaki |
| 5,424,199 | A | 6/1995 | Goeddel et al. |
| 5,442,043 | A | 8/1995 | Fukuta et al. |
| 5,444,167 | A | 8/1995 | Pettersson |
| 5,460,810 | A | 10/1995 | Williams et al. |
| 5,468,286 | A | 11/1995 | Wai-Chiu et al. |
| 5,547,669 | A | 8/1996 | Rogers |
| 5,574,142 | A | 11/1996 | Meyer, Jr. et al. |
| 5,589,367 | A | 12/1996 | Donson et al. |
| 5,639,640 | A | 6/1997 | Reddy et al. |
| 5,679,774 | A | 10/1997 | Wolf |
| 5,688,506 | A | 11/1997 | Grimes et al. |
| 5,693,495 | A | 12/1997 | Breiteneder |
| 5,693,616 | A | 12/1997 | Krstenansky et al. |
| 5,712,087 | A | 1/1998 | Houghton et al. |
| 5,736,146 | A | 4/1998 | Cohen et al. |
| 5,763,400 | A | 6/1998 | Adams et al. |
| 5,767,067 | A | 6/1998 | Arpaia et al. |
| 5,804,199 | A | 9/1998 | Aasjord et al. |
| 5,807,575 | A | 9/1998 | Dumoulin et al. |
| 5,830,671 | A | 11/1998 | Dennis et al. |
| 5,834,592 | A | 11/1998 | Reed et al. |
| 5,840,585 | A | 11/1998 | Rodkey et al. |
| 5,849,307 | A | 12/1998 | Metz et al. |
| 5,856,137 | A | 1/1999 | Reddy et al. |
| 5,866,686 | A | 2/1999 | Moore et al. |
| 5,869,288 | A | 2/1999 | Chapman et al. |
| 5,874,087 | A | 2/1999 | Lomonossoff et al. |
| 5,874,300 | A | 2/1999 | Blaser et al. |
| 5,874,527 | A | 2/1999 | Bamell |
| 5,885,783 | A | 3/1999 | Yoo et al. |
| 5,888,833 | A | 3/1999 | Serre et al. |
| 5,895,655 | A | 4/1999 | Eckhardt et al. |
| 5,897,863 | A | 4/1999 | Robson et al. |
| 5,897,867 | A | 4/1999 | Eckhardt et al. |
| 5,902,725 | A | 5/1999 | Robbins et al. |
| 5,904,925 | A | 5/1999 | Exner |

(Continued)

FOREIGN PATENT DOCUMENTS

WO 9602649 A1 2/1996

OTHER PUBLICATIONS

PCT International Search Report for Application PCT/US/2000/28443 dated Jun. 15, 2001.

(Continued)

*Primary Examiner*—Gary B. Nickol
*Assistant Examiner*—Bao Qun Li
(74) *Attorney, Agent, or Firm*—TraskBritt

(57) ABSTRACT

The present invention relates to modulating the nature and/or level of an immune response to a molecule. In particular, the invention relates to effecting an increase in the TH1 immune response to molecules such as, but not limited to, antigens or immunogens. The invention also relates to reducing a TH2 immune response to molecules. More particularly, the invention relates to altering the level of TH1- and TH2-associated immunoglobulins, the level of proliferation of TH1- and TH2-associated cytokines, and the level of proliferation of TH1 and TH2 cells.

18 Claims, No Drawings

U.S. PATENT DOCUMENTS

| | | | | |
|---|---|---|---|---|
| 5,910,306 | A | 6/1999 | Alving et al. | |
| 5,922,566 | A | 7/1999 | Bandman et al. | |
| 5,922,836 | A | 7/1999 | Watson et al. | |
| 5,928,861 | A | 7/1999 | Reyes | |
| 5,942,220 | A | 8/1999 | Warren et al. | |
| 5,942,237 | A | 8/1999 | Gizurarson et al. | |
| 5,945,105 | A | 8/1999 | Hiepe et al. | |
| 5,955,476 | A | 9/1999 | Muller et al. | |
| 5,958,415 | A | 9/1999 | Yuuki et al. | |
| 5,958,422 | A | 9/1999 | Lomonossoff | |
| 5,961,975 | A | 10/1999 | Fattom et al. | |
| 5,962,411 | A | 10/1999 | Rosen et al. | |
| 5,965,379 | A | 10/1999 | Tamarkin et al. | |
| 5,965,455 | A | 10/1999 | Singh et al. | |
| 5,973,121 | A | 10/1999 | Burks, Jr. et al. | |
| 5,976,539 | A | 11/1999 | Scott et al. | |
| 5,980,898 | A | 11/1999 | Glenn et al. | |
| 5,985,541 | A | 11/1999 | Jolivet-Reynaud | |
| 5,993,826 | A | 11/1999 | Hansen et al. | |
| 5,993,828 | A | 11/1999 | Morton | |
| 5,994,523 | A | 11/1999 | Kawakami et al. | |
| 6,004,760 | A | 12/1999 | Kobayashi et al. | |
| 6,007,806 | A | 12/1999 | Lathe et al. | |
| 6,013,433 | A | 1/2000 | Pellett et al. | |
| 6,013,481 | A | 1/2000 | DeBacker et al. | |
| 6,017,537 | A | 1/2000 | Alexander et al. | |
| 6,020,478 | A | 2/2000 | Hillman et al. | |
| 6,024,958 | A | 2/2000 | Lehner et al. | |
| 6,025,164 | A | 2/2000 | Bolin et al. | |
| 6,025,477 | A | 2/2000 | Calenoff | |
| 6,033,673 | A | 3/2000 | Clements | |
| 6,033,864 | A | 3/2000 | Braun et al. | |
| 6,034,227 | A | 3/2000 | Pecht et al. | |
| 6,037,165 | A | 3/2000 | Montagnier et al. | |
| 6,048,537 | A | 4/2000 | Violay et al. | |
| 6,063,402 | A | 5/2000 | Gebert et al. | |
| 6,069,233 | A | 5/2000 | Chen et al. | |
| 6,071,532 | A | 6/2000 | Chailof et al. | |
| 6,074,817 | A | 6/2000 | Landini et al. | |
| 6,074,833 | A | 6/2000 | Wientroub et al. | |
| 6,077,517 | A | 6/2000 | Thomas et al. | |
| 6,077,518 | A | 6/2000 | Thomas et al. | |
| 6,083,502 | A | 7/2000 | Pastan et al. | |
| 6,083,505 | A | 7/2000 | Miller et al. | |
| 6,083,703 | A | 7/2000 | Wang et al. | |
| 6,086,897 | A | 7/2000 | Thomas et al. | |
| 6,086,899 | A | 7/2000 | Balasubramanian et al. | |
| 6,087,110 | A | 7/2000 | Wang et al. | |
| 6,090,386 | A | 7/2000 | Griffith et al. | |
| 6,100,444 | A | 8/2000 | Frelinger et al. | |
| 6,103,219 | A | 8/2000 | Sherwood et al. | |
| 6,103,485 | A | 8/2000 | Mishiro et al. | |
| 6,103,501 | A | 8/2000 | Boime et al. | |
| 6,106,844 | A | 8/2000 | King | |
| 6,110,469 | A | 8/2000 | Singh et al. | |
| 6,110,687 | A | 8/2000 | Nilsen | |
| 6,110,724 | A | 8/2000 | Nakagomi et al. | |
| 6,110,892 | A | 8/2000 | Barbier et al. | |
| 6,117,631 | A | 9/2000 | Nilsen | |
| 6,124,436 | A | 9/2000 | McClanahan et al. | |
| 7,267,963 | B1 * | 9/2007 | Brennan .................... | 435/69.1 |

OTHER PUBLICATIONS

Brennan, F.R., et al., Pseudomonas Aeruginosa Outer-Membrane Protein F Epitopes are Highly Immunogenic in Mice When Expressed on a Plant Virus, Microbiology, vol. 145, Jan. 1999, pp. 211-220.

Brennan, F.R., et al., Immunogenicity of Peptides Derived From a Fibronectin-Binding Protein of *S. aureus* Expressed on Two Different Plant Viruses, Vaccine, vol. 17, Issues 15-16, Apr. 9, 1999, pp. 1846-1857.

Durrani, Z, et al., Intranasal Immunization with a Plant Virus Expressing a Peptide From HIV-1 gp41 Stimulates Better Mucosal and Systemic HIV-1-specific IgA and IgG than Oral Immunization, Journal of Immunological Methods, vol. 220, Issues 1-2, Nov. 1, 1998, pp. 93-103, Elsevier Science Publishers, B.V., Amsterdam.

McInerney, T.L., et al., Analysis of the Ability of Five Adjuvants to Enhance Immune Responses to a Chimeric Plant Virus Displaying an HIV-1 Peptide, Vaccine, vol. 17, Issues 11-12, Mar. 1999, pp. 1359-1368.

O'Neal et al., "Rotavirus virus-like particles administered mucosally induce protective immunity," J. Virol., 71:8707-8717 (1997).

Perez et al., "Stability of T(h)1 and T(h)2 populations," Intl. Immunol., 7:869-875 (1995).

Perez-Filgueira et al., "Isotype profiles induced in Balb/c mice during foot and mouth disease (FMD) virus infection or immunization with different FMD vaccine formulations," Vaccine 13:953-960 (1995).

Pertmer et al., "Influenza virus nucleoprotein-specific immunoglobulin G subclass and cytokine responses elicited by DNA vaccination are dependent on the route of vector DNA delivery," J. Virol., 70:6119-6125 (1996).

Peterson et al., "IgG subclass responses to Theiler's murine encephalomyelitis virus infection and immunization suggest a dominant role for Thl cells in susceptible mouse strains," Immunology, 75:652-658 (1992).

Porta et al., "Development of cowpea mosaic virus as a high yielding system for the presentation of foreign peptides," Virology, 202:949-955 (1994).

Rathnam et al., "Conjugation of a fetuin glycopeptide to human follicle-stimulating hormone and its subunits by photoactivation," Biochim. Biophys. Acta, 624:436-442 (1980).

Romagnani, S., et al., Induction of T(H)1 and T(H)2 Responses: a Key Role for the Natural Immune Response? Immunology Today, 1992, vol. 13, No. 10, pp. 379-381.

Romagnani, "Short analytical review TH1 and TH2 in human disease," Clin. Immunol. Immunopathol., 80:225-235 (1996).

Sant'Anna et al., "Basal immunoglobulin serum concentration and isotype distribution in relation to the polygenic control of antibody responsiveness in mice," Immunogenetics 22:131-139 (1985).

Scott et al., "IL-12 as an adjuvant for cell-mediated immunity," Seminl. Immunol., 9:285-291 (1997).

Sedlik et al., "Lack of T(h)1 or T(h)2 polarization of CD4 T cell response induced by particulate antigen targeted to phagocytic," Intl. Immunol., 9:91-103 (1997).

Sedgwick et al., "A solid-phase immunoenzymatic technique for the enumeration of specific antibody-secreting cells," J. Immunol. Methods, 57:301-309 (1983).

Shahinian et al., "A novel strategy affords high-yield coupling of antibody fab fragments to liposomes," Biochim. Biophys. Acta, 1239:157-167 (1995).

Sher et al., "Regulation of immunity to parasites by T cells and T cell-derived cytokines," Ann. Rev. Immunol., 10:385-409 (1992).

Smorlesi et al. Vaccine 2005, PMID 16288939 Oct. 24, pp. 1-10.

Tietze et al., "Conjugation of p-aminophenyl glycosides with squaric acid diester to a carrier protein and the use of neoglycoprotein in the histochemical detection of lectins," Bioconjug Chem., 2:148-153 (1991).

Verheul et al., "Monopalmitic acid-peptide conjugates induce cytotoxic T cell responses against malarial epitopes: importance of spacer amino acids," J. Immunol. Methods, 182:219-226 (1995).

Wechsler et al., "Heat-labile IgG2a antibodies affect cure of Trypanosoma muscull infection in C57BL/6 mice," J. Immunol, 137:2968-2972 (1986).

Zigterman et al., Nonionic block polymer surfactants modulate the humoral immune response against *Streptococcus pneumoniae*-derived hexasaccharide-protein conjugates Infect. Immun., 57:2712-2718 (1989).

Apostopoulos et al., "Oxidative/reductive conjugation of mannan to antigen selects for T(1) or T(2) immune responses," PNAS 92:10128-10132 (1995).
Balkovic et al., "Immunoglobulin G subclass antibody responses of mice to influenza virus antigens given in different forms," Antiviral Res., 8:151-160 (1987).
Ball et al., "Oral Immunization with Recombinant Norwalk Virus-Like Particles Induces a Systemic and Mucosal Immune Response in Mice," J. Virol., 72:1345-1353 (1998).
Bocher et al., "Synthesis of mono-and bifunctional peptide-dextran conjugates for the immobilization of peptide antigens on ELISA plates: properties and application," J. Immunol. Methods, 27:191-202 (1997).
Brennan et al., Immunogenicity of Peptides Derived From a Fibronectin-Binding Protein of *S. aureus* Expressed on Two Different Plant Viruses, Vaccine, Apr. 1999, vol. 17, pp. 1846-1857.
Brennan et al., "*Pseudomonas aeruginosa* outer-membrane protein F epitopes are highly immunogenic in mice when expressed on a plant virus," Microbiol., 145:211-220 (1999).
Brennan et al., "Chimeric plant virus particles administered nasally or orally induce systemic and mucosal immune response in mice," J. Virol., 73:930-938 (1999).
Brennan et al., A Chimaeric Plant Virus Vaccine Protects Mice Against a Bacterial Infection, Microbiology, 1999, vol. 145, pp. 2061-2067.
Brett et al., "Influence of the antigen delivery system on immunoglobulin isotype selection and cytokine production in response to influenza A nucleoprotein," Immunology, 80:306-312 (1993).
Brubaker et al., "Thl-Associated Immune Responses to B-Galactosidase Expressed by a Replication-Defective Herpes Simplex Virus," J. Immunol., 157:1598-1604 (1996).
Brusselle et al., Allergen-Induced Airway Inflammation and Bronchial Responsiveness in Wild-Type and Interleukin-4-Deficient Mice, American Journal of Respiratory Cell and Molecular Biology 1995, vol. 12, No. 3, pp. 254-259.
Charnow et al.,"Conjugation of Soluble CD4 without Loss of Biological Activity via a Novel Carbohydrate-directed Cross-linking Reagent," J. Biol. Chem., 267:15916-15922 (1992).
Chu et al., "CpG oligodexynucleotides act as adjuvants that switch on T helper 1 (Thl) immunity," J. Exp. Med., 186:1623-1631 (1997).
Cooper (1994) The selective induction of different immune responses by vaccine adjuvants. In:Vaccine Design (G.I. Ada., ed), R.G. Landes Company, pp. 125.
Coutelier et al.,"IgG2a Restriction of Murine Antibodies Elicited by Viral Infections," J. Exp. Med., 165:64-69 (1987).
D'Alessandro et al., "Peroxidase-labelling of human serum transferrin by conjugation to oligosaccharide moieties," Clin. Chim., Acta, 22:189-197 (1998).
Dalsgaard et al., "Plant-derived vaccine protects target animals against a viral disease," Nat. Biotechnol., 15:248-252 (1997).
Devi et al., "Capsular polysaccharide-protein conjugate vaccines of carbotype 1 vibrio vulnificus: construction, immunogenicity, and protective efficacy in a murine model," Infect. Immun., 63:2906-2911 (1995).
Drabick et al., "Covalent polymyxin B conjugate with human immunoglobulin G as an antiendotoxin reagent," Antimicrob. Agents Chemother., 42:583-588 (1988).
Durrani et al., Intranasal Immunization with a Plant Virus Expressing a Peptide From HIV-1 gp41 Stimulates Better Mucosal and Systemic HIV-1 Specific IgA and IgG than Oral Immunization, J. Immunological Method, 1998, vol. 220, pp. 93-103.
Erb et al.,"The role of Th2 type CD4 T cells and Th2 type CD8 T cells in asthma," Immunol. Cell Biol., 74:206-208 (1996).
Fernando et al., "Vaccine-induced Thl-type responses are dominant over Th2-type responses in the short term whereas pre-existing th2 responses are dominant in the longer term," Scand. J. Immunol., 47:459-465 (1998).
Friede et al., "Selective induction of protection against influenza virus infection in mice by a lipid-peptide conjugate delivered in liposomes," Vaccine, 12:791-797 (1994).
Hocart et al., "The IgG Subclass Responses to Influenza Virus Haemagglutinin in the Mouse: Effect of Route of Inculation," J. Gen. Virol., 70:809-818 (1989).
Hocart et al., "The Immunoglobulin G Subclass Responses of Mice to Influenza A Virus: the Effect of Mouse Strain, and the Neutralizing Abilities of Individual Protein A-purified Subclass Antibodies," J. Gen. Virol., 70:2439-2448 (1989).
Heusser et al., "Receptors for IgG: Subclass specificity of Receptors on different mouse cell types and the definition of two distinct receptors on a macrophage cell line," J. Exp. Med., 145:1316-1327 (1977).
Ishizaka et al., "IgG subtype is correlated with efficiency of passive protection and effector function of anti-herpes simplex virus glycoprotein D monoclonal antibodies," J. Infect. Dis., 172:1108-1111 (1995).
Jahn-Schmid et al., "Immunoreactivity of allergen (Bet v 1) conjugated to crystalline bacterial cell surface layers (S-layers)," Immuntechnology, 2:103-113 (1996).
Jahn-Schmid et al., "Bet v 1, the major birch pollen allergen, conjugated to crystalline bacterial cell surface proteins, expands allergen-specific T Cells and T(h)l/T(h)0 phenotype in vitro by induction of 1L-12," Intl. Immunol., 9:1867-1874 (1997).
James, Judith, et al., An Increased Prevalence of Epstein-Barr Virus Infection in Young Patients Suggests a Possible Etiology for Systemic Lupus Erythematosus, The Journal of Clinical Investigation, Dec. 12, 1997, vol. 100, No. 12, pp. 3019-3026.
James, Judith, et al., Immunoglobulin Epitope Spreading and Autoimmune Disease After Peptide Immunization: Sm B/B'-Derived PPPGMRPP and PPPGIRGP Induce Spliceosome Autoimmunity, The Journal of Experimental Medicine, 1995, pp. 453-461, vol. 181.
Kabir, "Preparation and immunogenicity of a bivalent cell-surface protein-polysaccharide conjugate of *Vibrio cholerae*," J. Med. Microbiol., 23:9-18 (1987).
Kaminski et al., "Importance of antibody isotype in monoclonal anti-idiotype therapy of a murine B cell lymphoma. A study of hybridoma class switch variants," J. Immunol., 136:1123-1124 (1986).
Kamps et al., "Preparation and characterization of conjugates of (modified) human serum albumin and liposomes: drug carriers with an intrinsic abti-HIV activity," Biochem. Biophys. Acta, 1278:183-190 (1996).
Krebitz, Monika, et al., Plant-Based Heterologous Expression of Mal d 2, a Thaumatin-Like Protein and Allergen of Apple (Malus Domestica) and its Characterization as an Antifungal Protein, Journal of Molecular Biology, Jun. 13, 2003, pp. 721-730, vol. 329, Issue 4.
Klaus et al., "Activation of mouse complement by different classes of mouse antibody", Immunology, 38:687-695 (1979).
Lees et al., "Activation of soluble polysaccharides with 1-cyano-4-dimethylaminopyridinium tetrafluoroborate for use in protein-polysaccharide conjugate vaccines and immunological reagents," Vaccine, 14:190-198 (1996).
Londono et al., "Immunization of mice using *Salmonella typhimurium* expressing human papillomavirus type 16 E7 epitopes inserted into hepatitis B virus core antigen," Vaccine 14:545-552 (1996).
Maddox, Lee, et al., The Pathophysiology of Asthma, Annual Review of Medicine, Feb. 2002, pp. 477-498, vol. 53.
Mazer et al., "An ELISA spot assay for quantitation of humann immunoglobulin-secreting cells," J. Allergy Clin. Immunol., 88:235-243 (1991).
McInerney, Tracey, et al., Analysis of the Ability of Five Adjuvants to Enchance Immune Response to a Chimeric Plant Virus Displaying an HIV-1 Peptide, Vaccine, Mar. 1999, vol. 17, pp. 1359-1368.
McKendall et al., "Murine IgG subclass responses to herpes simplex virus type 1 and polypetides," J. Gen. Virol., 69:847-857 (1988).
McLain et al., "Human immunodeficiency virus type 1-neutralizing antibodies raised to a glycoprotein 41 peptide expressed on the surface of a plant virus," AIDS Res. Hum. Retro., 11:327-334 (1995).
Mosmann et al.,"Two Types of Murine Helper T Cell Clone. I. Definition According to Profiles of Lymphokine Activities and Secreted Proteins," J. Immunol., 136:2348-2357 (1986).

Mueller et al., Peroxisome Proliferator-Activated Receiptor y Ligands Attenuate Immunological Sysptoms of Experimental Allergic Asthma, Achives of Biochemistry and Biophysics, Oct. 2003, vol. 418, Issue 2, pp. 186-196.

Munoz-Valle, et al., T(H)1/T(H)2 Cytokine Profile, Metalloprotease-9 Activity and Hormonal Status in Pregnant Rheumatoid Arthritis and Systemic Lupus Erythematosus Patients, Clin. Exp. Immunnol., 2003, vol. 131, pp. 377-384.

Murray, "How the MHC selects Thl/Th2 immunity," Immunol. Today, 19:157-163 (1998).

Natsuume-Sakai et al., "Quantitative estimations of five classes of immunoglobulin in inbred mouse strains," Immunology, 32:861 (1977).

Nguyen et al., "Mechanism of virus-induced Ig subclass shifts," J. Immunol., 152:478-484 (1994).

* cited by examiner

SEQUENCE LISTING

```
<160> NUMBER OF SEQ ID NOS: 30

<210> SEQ ID NO 1
<211> LENGTH: 4
<212> TYPE: PRT
<213> ORGANISM: Artificial Sequence
<220> FEATURE:
<223> OTHER INFORMATION: Synthetic

<400> SEQUENCE: 1

Asp Asp Asp Asp
1


<210> SEQ ID NO 2
<211> LENGTH: 5
<212> TYPE: PRT
<213> ORGANISM: Artificial Sequence
<220> FEATURE:
<223> OTHER INFORMATION: Synthetic

<400> SEQUENCE: 2

Lys Lys Lys Lys Lys
1               5


<210> SEQ ID NO 3
<211> LENGTH: 5
<212> TYPE: PRT
<213> ORGANISM: Artificial Sequence
<220> FEATURE:
<223> OTHER INFORMATION: Synthetic

<400> SEQUENCE: 3

Lys Lys Arg His Lys
1               5
```

-continued

<210> SEQ ID NO 4
<211> LENGTH: 4
<212> TYPE: PRT
<213> ORGANISM: Artificial Sequence
<220> FEATURE:
<223> OTHER INFORMATION: Synthetic

<400> SEQUENCE: 4

Arg Arg His Lys
1

<210> SEQ ID NO 5
<211> LENGTH: 4
<212> TYPE: PRT
<213> ORGANISM: Artificial Sequence
<220> FEATURE:
<223> OTHER INFORMATION: Synthetic

<400> SEQUENCE: 5

Asp Cys Glu Asp
1

<210> SEQ ID NO 6
<211> LENGTH: 5
<212> TYPE: PRT
<213> ORGANISM: Artificial Sequence
<220> FEATURE:
<223> OTHER INFORMATION: Synthetic

<400> SEQUENCE: 6

Asp Asp Glu Glu Glu
1               5

<210> SEQ ID NO 7
<211> LENGTH: 4
<212> TYPE: PRT
<213> ORGANISM: Artificial Sequence
<220> FEATURE:
<223> OTHER INFORMATION: Synthetic

<400> SEQUENCE: 7

Glu Cys Lys Arg
1

<210> SEQ ID NO 8
<211> LENGTH: 6
<212> TYPE: PRT
<213> ORGANISM: Artificial Sequence
<220> FEATURE:
<223> OTHER INFORMATION: Synthetic

<400> SEQUENCE: 8

Asp Cys Glu His Arg Lys
1               5

<210> SEQ ID NO 9
<211> LENGTH: 12
<212> TYPE: PRT
<213> ORGANISM: Artificial Sequence
<220> FEATURE:
<223> OTHER INFORMATION: Synthetic

<400> SEQUENCE: 9

Asp Lys Asp Lys Asp Lys Asp Lys Asp Lys Asp Lys
1               5                   10

<210> SEQ ID NO 10

-continued

<211> LENGTH: 12
<212> TYPE: PRT
<213> ORGANISM: Artificial Sequence
<220> FEATURE:
<223> OTHER INFORMATION: Synthetic

<400> SEQUENCE: 10

Glu Cys Lys Arg Glu Cys Lys Arg Glu Cys Lys Arg
1 5 10

<210> SEQ ID NO 11
<211> LENGTH: 12
<212> TYPE: PRT
<213> ORGANISM: Artificial Sequence
<220> FEATURE:
<223> OTHER INFORMATION: Synthetic

<400> SEQUENCE: 11

Asp Cys Glu His Arg Lys Asp Cys Glu His Arg Lys
1 5 10

<210> SEQ ID NO 12
<211> LENGTH: 18
<212> TYPE: PRT
<213> ORGANISM: Artificial Sequence
<220> FEATURE:
<223> OTHER INFORMATION: Synthetic

<400> SEQUENCE: 12

Asp Cys Glu His Arg Lys Asp Cys Glu His Arg Lys Asp Cys Glu His
1 5 10 15

Arg Lys

<210> SEQ ID NO 13
<211> LENGTH: 30
<212> TYPE: PRT
<213> ORGANISM: Artificial Sequence
<220> FEATURE:
<223> OTHER INFORMATION: Synthetic

<400> SEQUENCE: 13

Cys Asp Asp Glu Cys Lys Arg Arg Arg His Cys Asp Asp Glu Cys Lys
1 5 10 15

Arg Arg Arg His Cys Asp Asp Glu Cys Lys Arg Arg Arg His
20 25 30

<210> SEQ ID NO 14
<211> LENGTH: 8
<212> TYPE: PRT
<213> ORGANISM: Artificial Sequence
<220> FEATURE:
<223> OTHER INFORMATION: Synthetic

<400> SEQUENCE: 14

Glu Arg Glu Arg Glu Arg Glu Arg
1 5

<210> SEQ ID NO 15
<211> LENGTH: 10
<212> TYPE: PRT
<213> ORGANISM: Artificial Sequence
<220> FEATURE:
<223> OTHER INFORMATION: Synthetic

<400> SEQUENCE: 15

Asp His Asp His Asp His Asp His Asp His

-continued

```
1               5                   10


<210> SEQ ID NO 16
<211> LENGTH: 123
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(41)
<223> OTHER INFORMATION: Glu at these positions can be from one residue
      to forty consecutive residues.
<220> FEATURE:
<221> NAME/KEY: MISC_FEATURE
<222> LOCATION: (43)..(82)
<223> OTHER INFORMATION: Lys at these positions can be from one residue
      to forty consecutive residues.
<220> FEATURE:
<221> NAME/KEY: MISC_FEATURE
<222> LOCATION: (84)..(123)
<223> OTHER INFORMATION: Glu at these positions can be from one residue
      to forty consecutive residues.

<400> SEQUENCE: 16

Asp Glu Glu Glu Glu Glu Glu Glu Glu Glu Glu Glu Glu Glu Glu Glu
1               5                   10                  15

Glu Glu Glu Glu Glu Glu Glu Glu Glu Glu Glu Glu Glu Glu Glu Glu
            20                  25                  30

Glu Glu Glu Glu Glu Glu Glu Glu Glu Gly Lys Lys Lys Lys Lys Lys
        35                  40                  45

Lys Lys Lys Lys Lys Lys Lys Lys Lys Lys Lys Lys Lys Lys Lys Lys
    50                  55                  60

Lys Lys Lys Lys Lys Lys Lys Lys Lys Lys Lys Lys Lys Lys Lys Lys
65                  70                  75                  80

Lys Lys Asp Glu Glu Glu Glu Glu Glu Glu Glu Glu Glu Glu Glu Glu
                85                  90                  95

Glu Glu Glu Glu Glu Glu Glu Glu Glu Glu Glu Glu Glu Glu Glu Glu
            100                 105                 110

Glu Glu Glu Glu Glu Glu Glu Glu Glu Glu Glu
        115                 120


<210> SEQ ID NO 17
<211> LENGTH: 124
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(41)
<223> OTHER INFORMATION: Glu at these positions can be from one residue
      to forty consecutive residues.
<220> FEATURE:
<221> NAME/KEY: MISC_FEATURE
<222> LOCATION: (43)..(122)
<223> OTHER INFORMATION: Lys at these positions can be from one residue
      to eighty consecutive residues.

<400> SEQUENCE: 17

Asp Glu Glu Glu Glu Glu Glu Glu Glu Glu Glu Glu Glu Glu Glu Glu
1               5                   10                  15

Glu Glu Glu Glu Glu Glu Glu Glu Glu Glu Glu Glu Glu Glu Glu Glu
            20                  25                  30

Glu Glu Glu Glu Glu Glu Glu Glu Glu Gly Lys Lys Lys Lys Lys Lys
        35                  40                  45
```

-continued

```
Lys Lys Lys Lys Lys Lys Lys Lys Lys Lys Lys Lys Lys Lys Lys Lys
    50                  55                  60

Lys Lys Lys Lys Lys Lys Lys Lys Lys Lys Lys Lys Lys Lys Lys Lys
65                  70                  75                  80

Lys Lys Lys Lys Lys Lys Lys Lys Lys Lys Lys Lys Lys Lys Lys Lys
                85                  90                  95

Lys Lys Lys Lys Lys Lys Lys Lys Lys Lys Lys Lys Lys Lys Lys Lys
            100                 105                 110

Lys Lys Lys Lys Lys Lys Lys Lys Lys Lys Asp Glu
        115                 120


<210> SEQ ID NO 18
<211> LENGTH: 46
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(41)
<223> OTHER INFORMATION: Arg at these positions can be from one residue
      to forty consecutive residues.

<400> SEQUENCE: 18

Lys Arg Arg Arg Arg Arg Arg Arg Arg Arg Arg Arg Arg Arg Arg Arg
1               5                   10                  15

Arg Arg Arg Arg Arg Arg Arg Arg Arg Arg Arg Arg Arg Arg Arg Arg
            20                  25                  30

Arg Arg Arg Arg Arg Arg Arg Arg Arg Ser Gly Asp Glu Asp
        35                  40                  45


<210> SEQ ID NO 19
<211> LENGTH: 85
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(41)
<223> OTHER INFORMATION: Arg at these positions can be from one residue
      to forty consecutive residues.
<220> FEATURE:
<221> NAME/KEY: MISC_FEATURE
<222> LOCATION: (45)..(84)
<223> OTHER INFORMATION: Asp at these positions can be from one residue
      to forty consecutive residues.

<400> SEQUENCE: 19

Lys Arg Arg Arg Arg Arg Arg Arg Arg Arg Arg Arg Arg Arg Arg Arg
1               5                   10                  15

Arg Arg Arg Arg Arg Arg Arg Arg Arg Arg Arg Arg Arg Arg Arg Arg
            20                  25                  30

Arg Arg Arg Arg Arg Arg Arg Arg Arg His Pro Met Asp Asp Asp Asp
        35                  40                  45

Asp Asp Asp Asp Asp Asp Asp Asp Asp Asp Asp Asp Asp Asp Asp Asp
    50                  55                  60

Asp Asp Asp Asp Asp Asp Asp Asp Asp Asp Asp Asp Asp Asp Asp Asp
65                  70                  75                  80

Asp Asp Asp Asp Glu
                85
```

-continued

<210> SEQ ID NO 20
<211> LENGTH: 12
<212> TYPE: PRT
<213> ORGANISM: Artificial Sequence
<220> FEATURE:
<223> OTHER INFORMATION: Synthetic

<400> SEQUENCE: 20

Asp Glu Gly Lys Gly Lys Gly Lys Gly Lys Asp Glu
1 5 10

<210> SEQ ID NO 21
<211> LENGTH: 14
<212> TYPE: PRT
<213> ORGANISM: Pseudomonas aeruginosa

<400> SEQUENCE: 21

Asn Glu Tyr Gly Val Glu Gly Gly Arg Val Asn Ala Val Gly
1 5 10

<210> SEQ ID NO 22
<211> LENGTH: 14
<212> TYPE: PRT
<213> ORGANISM: Pseudomonas aeruginosa

<400> SEQUENCE: 22

Asn Ala Thr Ala Glu Gly Arg Ala Ile Asn Arg Arg Val Glu
1 5 10

<210> SEQ ID NO 23
<211> LENGTH: 30
<212> TYPE: PRT
<213> ORGANISM: Staphylococcus aureus

<400> SEQUENCE: 23

Gly Gln Asn Asn Gly Asn Gln Ser Phe Glu Glu Asp Thr Glu Lys Asp
1 5 10 15

Lys Pro Lys Tyr Glu Gln Gly Gly Asn Ile Ile Asp Ile Asp
20 25 30

<210> SEQ ID NO 24
<211> LENGTH: 37
<212> TYPE: PRT
<213> ORGANISM: Homo sapiens

<400> SEQUENCE: 24

Thr Cys Asp Asp Pro Arg Phe Gln Asp Ser Ser Ser Ser Lys Ala Pro
1 5 10 15

Pro Pro Ser Leu Pro Ser Pro Ser Arg Leu Pro Gly Pro Ser Asp Thr
20 25 30

Pro Ile Leu Pro Gln
35

<210> SEQ ID NO 25
<211> LENGTH: 24
<212> TYPE: PRT
<213> ORGANISM: Homo sapiens

<400> SEQUENCE: 25

Thr Cys Asp Asp Pro Arg Phe Gln Asp Ser Ser Arg Leu Pro Gly Pro
1 5 10 15

-continued

```
Ser Asp Thr Pro Ile Leu Pro Gln
            20


<210> SEQ ID NO 26
<211> LENGTH: 14
<212> TYPE: PRT
<213> ORGANISM: Homo sapiens

<400> SEQUENCE: 26

Glu Leu Asp Val Cys Val Glu Glu Ala Glu Gly Glu Ala Pro
1               5                   10


<210> SEQ ID NO 27
<211> LENGTH: 13
<212> TYPE: PRT
<213> ORGANISM: Homo sapiens

<400> SEQUENCE: 27

Leu Glu Glu Lys Lys Gly Asn Tyr Val Val Thr Asp His
1               5                   10


<210> SEQ ID NO 28
<211> LENGTH: 17
<212> TYPE: PRT
<213> ORGANISM: Parvovirus

<400> SEQUENCE: 28

Asp Gly Ala Val Gln Pro Asp Gly Gly Gln Pro Ala Val Arg Asn Glu
1               5                   10                  15

Arg


<210> SEQ ID NO 29
<211> LENGTH: 12
<212> TYPE: PRT
<213> ORGANISM: Artificial Sequence
<220> FEATURE:
<223> OTHER INFORMATION: Synthetic

<400> SEQUENCE: 29

Asp Glu Gly Lys Gly Lys Gly Lys Gly Lys Asp Glu
1               5                   10


<210> SEQ ID NO 30
<211> LENGTH: 6
<212> TYPE: PRT
<213> ORGANISM: Artificial Sequence
<220> FEATURE:
<223> OTHER INFORMATION: Synthetic

<400> SEQUENCE: 30

Arg Glu Arg Glu His Cys
1               5
```

MODIFIED PLANT VIRUSES AND METHODS OF USE THEREOF

CROSS-REFERENCE TO RELATED APPLICATIONS

This application is a continuation of application Ser. No. 10/110,683, filed Apr. 12, 2002, now U.S. Pat. No. 7,267,963, issued Sep. 11, 2007, which is a U.S. national entry of International Application No. PCT/US00/28443, filed on Oct. 13, 2000, which claims priority from Great Britain application 9924351.1, filed Oct. 14, 1999, now abandoned. The disclosure of each of the previously referenced U.S. patent applications and patents (if applicable) is hereby incorporated herein by this reference in its entirety.

FIELD OF THE INVENTION

The present invention relates to modulating the nature and/or level of an immune response to a molecule. In particular, the invention relates to effecting an increase in the TH1 immune response to molecules such as, but not limited to, antigens or immunogens. The invention also relates to reducing a TH2 immune response to molecules. More particularly, the invention relates to altering the level of TH1- and TH2-associated immunoglobulins, the level of proliferation of TH1- and TH2-associated cytokines, and the level of proliferation of TH1 and TH2 cells.

BACKGROUND OF THE INVENTION

The priming of the TH1, rather than TH2, subset of CD4+ T cells is of primary importance in vaccine design. This is because TH1 cells produce IL-2, IFN-γ, and TNF-β cytokines that mediate macrophage and cytotoxic T cell activation (CTL), and are the principal effectors of cell-mediated immunity against intracellular microbes and of delayed type hypersensitivity (DTH) reactions. IFN-γ also induces B cell isotype class-switching to the principal effector isotype of mouse IgG. $IgG_{2a}$, and to a lesser extent $IgG_{2b}$, enhances antibody-dependent cell mediated cytotoxicity (ADCC) and strongly binds Clq of the classical complement pathway which opsonizes cells or antibody clusters for phagocytosis. For example, as a result of these effector functions in mouse, $IgG_{2a}$ has been found to better protect mice against virus infections (Ishizaka et al. (1995) J. Infect. Dis. 172:1108), murine tumors (Kaminski et al. (1986) J. Immunol. 136: 1123), and parasites (Wechsler et al. (1986) J. Immunol. 137:2968), and to enhance bacterial clearance (Zigterman et al. (1989) Infect. Immun. 57:2712).

In contrast, TH2 cells produce IL-4, IL-5, IL-10, and IL-13, which have the undesirable effect of suppressing cell mediated immunity (Mossman et al. (1986) J. Immunol. 136: 2248). Furthermore, IL-4 induces B cells to produce both an IgG subclass that poorly fixes complement and does not mediate ADCC, as well as IgE that binds to mast cells and basophils.

The prior art has attempted to improve vaccine design by directing the development of TH1 cells, while recognizing that the priming of TH cell subsets is affected by the strain of animal used (Hocart et al. (1989) J. Gen. Virol. 70:2439), the identity of the antigen, the route of antigen delivery (Hocart et al. (1989) J. Gen. Virol. 70:809), and the immunization regimen (Brett et al. (1993) Immunology 80:306).

One approach of the prior art to generate antigen-specific TH1 responses has been through the use of the oxidative/reductive conjugation of mannan to antigen (Apostopoulos et al. (1995) Proc. Natl. Acad. Sci. USA 92:10128-10132) or the conjugation of proteins to bacterial proteins (Jahn-Schmid et al. (1997) Intl. Immunol. 9:1867). However, coupling to commonly used carriers such as KLH and tetanus toxoid, is often unsuccessful at increasing the $IgG_{2a}$:$IgG_1$ ratio.

Other methods of inducing TH1 responses include the use of immunomodulatory agents, such as extraneous adjuvants (for example: ISCOMS, QS-21, Quil A, etc.). However, alum is the only adjuvant which is currently approved for use in humans and is known to favor undesirable TH2-type responses rather than the more desirable TH1-type response.

Other immunomodulatory agents that have been used by the prior art include CpG oligodeoxyribonucleotides (Chu et al. (1997) J. Exp. Med. 186:1623) or cytokines, such as interleukin-12 (IL-12, Scott et al (1997) Semin. Immunol. 9:285), which may be added to immunogenic compositions leading to the production of high levels of $IgG_{2a}$ directed against soluble protein antigens. However, the cytokines' short half-life and considerable cost make utilizing them both technically and commercially unattractive in large-scale vaccination.

Yet another approach has been to use live animal virus vaccines to generate predominantly virus-specific $IgG_{2a}$ in mice (Hocart et al (1989) J. Gen. Virol. 70:809; Coutelier et al. (1987) J. Exp. Med. 165:64; Nguyen et al. (1994) J. Immunol. 152:478; Brubaker et al. (1996) J. Immunol. 157:1598). This approach has several disadvantages. First, live virus vaccines do not consistently result in a TH1-type immune response, since some live viruses favor production of other immunoglobulin isotypes characteristic of alternate T helper pathways (Coutelier et al. (1987) J. Exp. Med. 165:64; Perez-Filgueira et al. (1995) Vaccine 13:953). In addition, such animal virus vaccines are produced from viruses that are grown in cell culture systems that are expensive to design and run.

Moreover, the animal virus used as the vector is often a virus to which the animal may already have been exposed, and the animal may already be producing antibodies to the vector. The vector may, therefore, be destroyed by the immune system before the incorporated antigenic site of the second virus induces an immune response. Additionally, the composite animal virus approach involves genetic manipulation of live, animal-infecting viruses, with the risk that mutations may give rise to novel forms of the virus with altered infectivity, antigenicity and/or pathogenicity. Indeed, there are safety concerns over the use of live animal viral vaccines (World Health Organization, 1989). Furthermore, the safety concerns over the use of live animal viral vaccines are not overcome by using inactive animal viruses since inactive animal viruses generally do not favor $IgG_{2a}$ production. Indeed, it is thought that the infection process typified by live viruses per se generates IFN-γ leading to a predominance of TH1 response immunoglobulins (Nguyen et al. (1994) J. Immunol. 152:478).

While another approach has involved using live bacterial vectors and DNA immunization that favor the generation of TH1 responses to expressed peptides, this approach is, however, often dependent on, and sensitive to, either the route of delivery or adjuvant used. Moreover, safety concerns over the use of live bacterial vaccines and DNA vaccines (World Health Organization, 1989) further limit their clinical application.

Thus, there is a need for compositions and methods of generating TH1-type responses. Preferably, the generation of TH1-type responses by these compositions and methods is unaffected by the genetic background of the host animal, the identity of the antigen, the route of antigen delivery, and the immunization regimen.

SUMMARY OF THE INVENTION

The present invention provides methods and compositions that are effective in modulating the nature and/or level of an immune response to a molecule exemplified by, but not limited to, an antigen or immunogen. In particular, the invention provides methods and means for effecting a TH1 bias in the immune response to molecules, such as antigens or immunogens, and/or reducing a TH2 bias in the immune response to such molecules. More particularly, the invention provides methods and means for increasing a TH1 immune response that is directed against molecules that otherwise generally stimulate a TH2-type response. The invention further provides compositions and methods to reduce a TH2 immune response to molecules. Additionally provided herein are compositions and methods for altering (that is, increasing or decreasing) the level of TH1- and TH2-associated immunoglobulins, the level of proliferation of TH1- and TH2-associated cytokines, and the level of proliferation of TH1 and TH2 cells.

More particularly, the invention provides a method of altering the level of TH1-associated immunoglobulin in an animal, comprising: a) providing: i) aplant virus containing a heterologous peptide and ii) a host animal; b) administering the plant virus to the host animal to generate a treated animal; and c) testing for an increase in the level of TH1-associated immunoglobulin in the treated animal relative to the level of TH1-associated immunoglobulin in a control animal. In one embodiment, the method further comprises d) observing an increase in the level of TH1-associated immunoglobulin in the treated animal. Without intending to limit the invention to any particular route of administration, in another embodiment, the administering is selected from intranasal, oral, parenteral, subcutaneous, intrathecal, intravenous, intraperitoneal, and intramuscular administration. Also, without limitation of the invention to the type or source of compositions included in administration of the invention's viruses, in yet another embodiment, the administering further comprises administering a composition selected from immune adjuvant, cytokine, and pharmaceutical excipient. In a further embodiment, the administering results in reducing symptoms associated with exposure of the host animal to the heterologous peptide.

Although it is not intended that the invention be limited to any particular type of host animal, in yet another embodiment, the host animal is a mammal. It is not intended that the invention be limited to any particular mammal. However, in a preferred embodiment, the mammal is selected from mouse and human. In a more preferred embodiment, the host animal is mouse, and the TH1-associated immunoglobulin is selected from $IgG_{2a}$ and $IgG_{2b}$. In a yet more preferred embodiment, the TH1-associated immunoglobulin is $IgG_{2a}$. In another preferred embodiment, the host animal is human, and the TH1-associated immunoglobulin is selected from $IgG_1$ and $IgG_3$.

Without restricting the specificity of the TH1-associated immunoglobulin, in an alternative embodiment, the TH1-associated immunoglobulin is selected from immunoglobulin specific for the heterologous peptide and immunoglobulin specific for the plant virus. In another alternative embodiment, the plant virus is an RNA virus. In a further alternative embodiment, the plant virus is an icosahedral plant virus selected from Comoviruses, Tombusviruses, Sobemoviruses, and Nepoviruses. In a preferred embodiment, the plant virus is a Comovirus. In a more preferred embodiment, the Comovirus is cowpea mosaic virus (CPMV).

While the invention is not limited to any particular source or type of heterologous peptide, in an additional alternative embodiment, the heterologous peptide is selected from the β-subunit of the human chorionic gonadotrophin, human membrane bound IgE, human mutant epidermal growth factor receptor variant III, canine parvovirus, a peptide hormone, a gonadotrophin-releasing hormone, an allergen, a peptide derived from a cancer cell, and a peptide derived from an animal pathogen.

The invention is not intended to be limited to the location on the virus at which the heterologous peptide is expressed. Nonetheless, in yet another alternative embodiment, the heterologous peptide is expressed at an exposed portion of the coat protein of the plant virus. In a preferred embodiment, the coat protein has a beta-barrel structure and the heterologous peptide is inserted in a loop between individual strands of the beta sheet of the beta-barrel structure. In a more preferred embodiment, the heterologous peptide is inserted in the βB-βC loop of the plant virus. In another preferred embodiment, the heterologous peptide is inserted between alanine 22 and proline 23 of the small coat protein (VP-S) of CPMV. In another embodiment, a nucleic acid sequence encoding the heterologous peptide is inserted in the plant virus genome at a site that is free from direct nucleotide sequence repeats flanking the nucleic acid sequence.

It is not contemplated that the invention be restricted to the type of heterologous peptide. However, in yet another embodiment, the heterologous peptide is antigenic. In a preferred embodiment, the heterologous peptide is derived from an animal virus. In a more preferred embodiment, the animal virus is selected from foot-and-mouth disease virus, human immune deficiency virus, human rhinovirus, and canine parvovirus. In an alternative preferred embodiment, the heterologous peptide is derived from a composition selected from an animal pathogen, a hormone, and cytokine. In a more preferred embodiment, the animal pathogen is selected from a virus, bacterium, protozoan, nematode, and fungus. In yet a further embodiment, the heterologous peptide is immunogenic.

The invention additionally provides a method of altering the level of proliferation of TH1 cells in an animal, comprising: a) providing: i) a plant virus containing a heterologous peptide and ii) a host animal; b) administering the plant virus to the host animal to generate a treated animal; and c) testing for an increase in the level of proliferation of TH1 cells from the treated animal relative to the level of proliferation of TH1 cells from a control animal. In one embodiment, the method further comprises d) observing an increase in the proliferation level of TH1 cells from the treated animal relative to the proliferation level of TH1 cells from a control animal. In another embodiment, the administering results in reducing symptoms associated with exposure of the host animal to the heterologous peptide.

Also provided herein is a method of altering the level of a TH1-associated cytokine in an animal, comprising: a) providing: i) a plant virus containing a heterologous peptide and ii) a host animal; b) administering the plant virus to the host animal to generate a treated animal; and c) testing for an increase in the level of the cytokine produced by T cells from the treated animal relative to the level of the cytokine produced by T cells from a control animal. In one embodiment, the method further comprises d) observing an increase in the level of the cytokine produced by T cells from the treated animal relative to the level of the cytokine produced by T cells from a control animal. In another embodiment, the administering results in reducing symptoms associated with exposure of the host animal to the heterologous peptide. In yet another embodiment, the cytokine is selected from IL-2, TNF-β and IFN-γ. In a preferred embodiment, the cytokine is INF-γ. In a further embodiment, the level of a TH2-associated cytokine in the treated animal is the same as the level of the second cytokine in the host animal. In a preferred embodiment, the second cytokine is selected from IL-4, IL-5, IL-6, IL-9, IL-10, and IL-13. In a more preferred embodiment, the second cytokine is IL-4. In an additional embodiment, the level of a TH2-associated cytokine in the treated animal is reduced relative to the level of the second cytokine in the host animal.

The invention additionally provides a method of increasing the level of a TH1-type immune response to a molecule of interest in an animal comprising: a) providing: i) the molecule of interest; ii) a plant virus expressing a heterologous peptide capable of conjugating to the molecule of interest; and iii) a host animal; b) conjugating the molecule of interest to the heterologous peptide to generate a conjugate; and c) administering the conjugate to the host animal to generate a treated animal under conditions such that the level of TH1-type immune response to the molecule of interest in the treated animal is increased relative to the level of TH1-type immune response to the molecule of interest in a control animal. In one embodiment, the method further comprises d) testing for an increase in the level of TH1-type immune response to the molecule of interest in the treated animal relative to the level of TH1-type immune response to the molecule of interest in a control animal. In a preferred embodiment, the method further comprises e) observing an increase in the level of TH1-type immune response to the molecule of interest in the treated animal relative to the level of TH1-type immune response to the molecule of interest in a control animal.

While not limiting the nature or extent of the increased level of TH1-type response, in another preferred embodiment, the increased level of TH1-type immune response is selected from (a) increased level of TH1-associated immunoglobulin in the treated animal relative to the level of TH1-associated immunoglobulin in a control animal, (b) increased level of proliferation of TH1 cells from the treated animal relative to the level of proliferation of TH1 cells from a control animal, and (c) increased level of TH1-associated cytokine in the treated animal relative to the level of TH1-associated cytokine in a control animal. In another embodiment, the TH1-associated cytokine is selected from IL-2, TNF-β and IFN-γ. In a more preferred embodiment, the cytokine is INF-γ. In yet another embodiment, the administering results in reducing symptoms associated with exposure of the host animal to the molecule of interest. In an alternative embodiment, the molecule of interest comprises a peptide, polysaccharide, nucleic acid, or lipid. In a preferred embodiment, the molecule of interest is derived from a source selected from an animal pathogen, an allergen, and a cancer cell.

It is not intended that the invention be limited to the type or nature of virus. However, in another alternative embodiment, the plant virus is an icosahedral plant virus selected from Comoviruses, Tombusviruses, Sobemoviruses, and Nepoviruses.

In a preferred embodiment, the plant virus is a Comovirus. In a more preferred embodiment, the Comovirus is CPMV.

Although the location of introduction of the heterologous peptide into the virus is not intended to be limited, in a yet more preferred embodiment, the heterologous peptide is inserted between alanine 22 and proline 23 of the small coat protein (VP-S) of CPMV. In a further alternative embodiment, the heterologous peptide is expressed at an exposed portion of the coat protein of the plant virus.

The invention is not limited to the nature or type of heterologous peptide. Nonetheless, in an additional alternative embodiment, the heterologous peptide comprises one or more charged amino acids selected from negatively charged amino acids and positively charged amino acids, wherein the negative charge on the negatively charged amino acids is balanced by the positive charge on the positively charged amino acids. In a preferred embodiment, the negatively charged amino acids are selected from aspartic acid, glutamic acid, and cysteine. In another preferred embodiment, the positively charged amino acids are selected from lysine, arginine, and histidine. In yet another preferred embodiment, the heterologous peptide comprises a sequence of contiguous charged amino acids selected from a first sequence consisting of contiguous negatively charged amino acids and a second sequence consisting of contiguous positively charged amino acids. In a more preferred embodiment, the sequence of contiguous charged amino acids occurs in the heterologous peptide as a repeating sequence. In another more preferred embodiment, the heterologous sequence comprises the first and second sequences. In a yet more preferred embodiment, the first sequence is contiguous with the second sequence. In a particularly preferred embodiment, the contiguous first and second sequences occur in the heterologous peptide as a repeating sequence. In a further preferred embodiment, the heterologous peptide comprises non-contiguous negatively charged amino acids and non-contiguous positively charged amino acids. In a more preferred embodiment, the heterologous peptide further comprises a sequence of contiguous charged amino acids selected from a first sequence consisting of contiguous negatively charged amino acids, and a second sequence consisting of contiguous positively charged amino acids. In a yet more preferred embodiment, the heterologous peptide comprises the first sequence. In an additionally preferred embodiment, the first sequence of contiguous negatively charged amino acids has the general formula Asp-$Glu_n$-Gly-$Lys_{2n}$-Asp-$Glu_n$ listed as SEQ ID NO:16, where n is an integer of from 1 to 40. In a particularly preferred embodiment, the first sequence is the amino acid sequence Asp-Glu-Gly-Lys-Gly-Lys-Gly-Lys-Gly-Lys-Asp-Glu listed as SEQ ID NO:20.

Without limiting the route or mode of administration, in a further embodiment, the administering is selected from intranasal, oral, parenteral, subcutaneous, intrathecal, intravenous, intraperitoneal, and intramuscular administration. In an additional embodiment, the administering further comprises administering a composition selected from immune adjuvant, cytokine, and pharmaceutical excipient.

While the type of animal is not limited, the invention contemplates that, in yet another embodiment, the host animal is a mammal. In a preferred embodiment, the mammal is selected from mouse and human. In an alternative embodiment, the conjugate is immunogenic.

Also provided by the invention is a method of reducing the level of TH2-type immune response to a molecule of interest, comprising: a) providing: i) the molecule of interest; ii) a plant virus; and iii) a host animal; b) conjugating the molecule of interest to the plant virus to generate a conjugate; and c) administering the conjugate to the host animal to generate a treated animal under conditions such that the level of TH2-type immune response to the molecule of interest in the treated animal is reduced relative to the level of TH2-type immune response to the molecule of interest in a control animal. In one embodiment, the method further comprises d) testing for a reduction in the level of TH2-type immune response to the molecule of interest in the treated animal relative to the level of TH2-type immune response to the molecule of interest in a control animal. In a preferred embodiment, the method further comprises e) observing a reduction in the level of TH2-type immune response to the molecule of interest in the treated animal relative to the level of TH2-type immune response to the molecule of interest in a control animal. In another embodiment, the administering results in reducing symptoms associated with exposure of the host animal to the molecule of interest. In an alternative embodiment, the reduced level of TH2-type immune response is selected from (a) reduced level of TH2-associated immunoglobulin in the treated animal relative to the level of TH2-associated immunoglobulin in a control animal, (b) reduced level of proliferation of TH2 cells from the treated animal relative to the level of proliferation of TH2 cells from a control animal, and (c) reduced level of TH2-associated cytokine in the treated animal relative to the level of TH2-associated cytokine in a control animal. In a preferred embodiment, the TH2-associated cytokine is selected from IL-4, IL-5, IL-6, IL-9, IL-10, and IL-13. In a more preferred embodiment, the TH2-associated cytokine is IL-4. In another alternative embodiment, the molecule of interest comprises a peptide, polysaccharide, nucleic acid, or lipid. In an additional alternative embodiment, the molecule of interest is selected from an antigen and adjuvant. In a preferred embodiment, the antigen is a peptide. In yet another alternative embodiment, the host animal is mouse, and the TH2-associated immunoglobulin is selected from $IgG_1$ and $IgG_3$. In an additional embodiment, the host animal is human, and the TH2-associated immunoglobulin is $IgG_2$.

The invention also provides a method of reducing the level of an extant TH2-type immune response to a molecule of interest, comprising: a) providing: i) the molecule of interest, ii) a plant virus, and iii) a host animal exhibiting a TH2-type immune response to the molecule of interest; b) conjugating the molecule of interest to the plant virus to generate a conjugate; and c) administering the conjugate to the host animal to generate a treated animal under conditions such that the level of TH2-type immune response in the treated animal is reduced relative to the level of TH2-type immune response in the host animal. In one embodiment, the method further comprises d) testing for a reduction in the level of TH2-type immune response to the molecule of interest in the treated animal relative to the level of TH2-type immune response to the molecule of interest in a control animal. In a preferred embodiment, the method further comprises e) observing a reduction in the level of TH2-type immune response to the molecule of interest in the treated animal relative to the level of TH2-type immune response to the molecule of interest in a control animal. In another embodiment, the TH2-type response in the host animal is dominant.

The invention also provides a process of increasing the level of a TH1-type immune response to a molecule of interest in an animal, comprising: a) providing: i) the molecule of interest, ii) a plant virus expressing a heterologous peptide capable of conjugating to the molecule of interest, and iii) a host animal; b) conjugating the molecule of interest to the heterologous peptide to generate a conjugate; c) administering the conjugate to the host animal to generate a treated animal under conditions such that the level of TH1-type immune response to the molecule of interest in the treated animal is increased relative to the level of TH1-type immune response to the molecule of interest in a control animal; d) optionally testing for an increase in the level of TH1-type immune response to the molecule of interest in the treated animal relative to the level of TH1-type immune response to the molecule of interest in a control animal; and e) optionally observing an increase in the level of TH1-type immune response to the molecule of interest in the treated animal relative to the level of TH1-type immune response to the molecule of interest in a control animal. In one embodiment, the increased level of TH1-type immune response is selected from (a) increased level of TH1-associated immunoglobulin in the treated animal relative to the level of TH1-associated immunoglobulin in a control animal, (b) increased level of proliferation of TH1 cells from the treated animal relative to the level of proliferation of TH1 cells from a control animal, and (c) increased level of TH1-associated cytokine in the treated animal relative to the level of TH1-associated cytokine in a control animal. In another embodiment, the TH1-associated cytokine is selected from IL-2, TNF-β and IFN-γ. In yet another embodiment, the administering results in reducing symptoms associated with exposure of the host animal to the molecule of interest. In a further embodiment, the molecule of interest comprises a peptide, polysaccharide, nucleic acid, or lipid. In an alternative embodiment, the molecule of interest is derived from a source selected from an animal pathogen, an allergen, and a cancer cell. In yet another embodiment, the plant virus is an icosahedral plant virus selected from Comoviruses, Tombusviruses, Sobemoviruses, and Nepoviruses. In an alternative embodiment, the plant virus is a Comovirus. In a more preferred embodiment, the Comovirus is CPMV. In yet another embodiment, the heterologous peptide is expressed at an exposed portion of the coat protein of the plant virus. In an alternative embodiment, the heterologous peptide comprises one or more charged amino acids selected from negatively charged amino acids and positively charged amino acids, wherein the negative charge on the negatively charged amino acids is balanced by the positive charge on the positively charged amino acids. In another embodiment, the negatively charged amino acids are selected from aspartic acid, glutamic acid, and cysteine, and the positively charged amino acids are selected from lysine, arginine, and histidine. In another embodiment, the heterologous peptide comprises a sequence of contiguous charged amino acids selected from a first sequence consisting of contiguous negatively charged amino acids and a second sequence consisting of contiguous positively charged amino acids. In yet another embodiment, the sequence of contiguous charged amino acids occurs in the heterologous peptide as a repeating sequence. In a further embodiment, the heterologous sequence comprises the first and second sequences, and wherein the first sequence is contiguous with the second sequence. In yet a further embodiment, the contiguous first and second sequences occur in the heterologous peptide as a repeating sequence. In still a further embodiment, the heterologous peptide comprises non-contiguous negatively charged amino acids and non-contiguous positively charged amino acids, and wherein the heterologous peptide further comprises a sequence of contiguous charged amino acids selected from a first sequence consisting of contiguous negatively charged amino acids, and a second sequence consisting of contiguous positively charged amino acids. In another embodiment, the first sequence of contiguous negatively charged amino acids has the general formula Asp-$Glu_n$-Gly-$Lys_{2n}$-Asp-$Glu_n$ listed as SEQ ID NO:16, where n is an integer of from 1 to 40. In still another embodiment, the administering is selected from intranasal, oral, parenteral, subcutaneous, intrathecal, intravenous, intraperitoneal, and intramuscular administration. In yet another embodiment, the administering further comprises administering a composition selected from immune adjuvant, cytokine, and pharmaceutical excipient. In a further embodiment, the host animal is a mammal. In another alternative embodiment, the mammal is selected from mouse and human. In one preferred embodiment, the conjugate is immunogenic.

The invention also provides a method for stimulating a predominantly TH1-type peptide-specific immune response comprising the conjugation of an antigen to a plant virus and administering the resultant immunogenic complex to an animal. Preferably, the plant virus is an icosahedral plant virus. More preferably, the plant virus is a Comovirus. Yet more preferably, the plant virus is CPMV. In one embodiment, the antigen is a foreign peptide that is expressed as an insertion polypeptide encoded by a recombinant structural gene of the plant virus. Preferably, the antigen is expressed as a fusion polypeptide encoded by a recombinant coat protein structural gene. In yet another embodiment, the immunogenic complex is administered in the presence of a pharmaceutically acceptable excipient. In a further embodiment, the mode of administration of the immunogenic complex is selected from intranasal inoculation, oral inoculation, parenteral inoculation, and subcutaneous inoculation. In yet another embodiment, the immunogenic complex is administered in the presence of an immunomodulatory agent. Preferably, the immunomodulatory agent is an immune adjuvant. More preferably, the immune adjuvant is selected from the group comprising: cholera toxin (CT) and mutants thereof, heat-labile enterotoxin (LT) and mutants thereof, Quil A (QS-21), the R1B1 adjuvant and ISCOMs. In an alternative preferred embodiment, the immunomodulatory agent is a cytokine, preferably a cytokine that can be secreted from a CD4+ TH1 lymphocyte of an animal. More preferably, the cytokine is selected from the group of interleukin-2, interferon-γ, and tumor necrosis factor-β. In an additional embodiment, the immunogenic complex is administered by a subcutaneous route at one site in a single dose, by a subcutaneous route at more than one site in a single contemporaneous dose, by a parenteral route at one site in a single dose, by a parenteral route at more than one site in a single contemporaneous dose, by a subcutaneous route at one site in more than one dose, by a parenteral route at one site in more than one dose, by a subcutaneous route at more than one site in more than one dose, and/or by a parenteral route at more than one site in more than one dose.

Also provided by the invention is a chimeric virus particle, which is useful in any of the above-described methods, and in which a reactive peptide capable of having chemically conjugated to it a proteinaceous or non-proteinaceous molecule is encoded within a structural gene of the chimeric plant virus genome. In one embodiment, the chemically reactive peptide is inserted into a coat protein of the chimeric virus particle. In another embodiment, the insertion of the chemically reactive peptide is between alanine 22 and proline 23 of the small coat protein (VP-S) of CPMV. In yet another embodiment, the positive charges on the reactive amino acid residues (X) are balanced by the inclusion of a corresponding number of negatively charged amino acid residues (Y) within the reactive peptide, conforming to a general formula X(n)Y(n), where n is an integer of between 1 and 40. In another embodiment, the inserted chemically reactive peptide has an amino acid sequence of the general formula DE(n)GK(n)DE(n) listed as SEQ ID NO:16, where n is an integer of between 1 and 40. In a preferred embodiment, the inserted chemically reactive peptide has the amino acid sequence DEGKGKGKGKDE (SEQ ID NO:20, also listed as SEQ ID NO:29). In a further embodiment, the antigen is a carbohydrate moiety conjugated via a chemical bond to a reactive peptide expressed as an inserted fusion within a structural protein of a chimeric plant virus.

The invention also provides a method of bypassing a TH2-type immune reaction favored by the inherent immune stimulatory characteristics of an antigen comprising conjugating the antigen to a plant virus and administering the resultant immunogenic complex to an animal.

Also disclosed herein is a method of bypassing a TH2-type immune reaction favored by the inherent immune stimulatory characteristics of a peptide comprising expressing the peptide as a fusion polypeptide encoded by the recombinant genome of a plant virus and administering the resultant immunogenic complex to an animal.

The invention additionally provides a method of bypassing a TH2-type immune reaction favored by the genetic constitution of an animal to an antigen comprising conjugating the antigen to a plant virus and administering the resultant immunogenic complex to the animal.

Moreover, the invention provides a method of bypassing a TH2-type immune reaction favored by the genetic constitution of an animal to a peptide comprising expressing the peptide as a fusion polypeptide encoded by the recombinant genome of a plant virus and administering the resultant immunogenic complex to an animal.

Also provided by the invention is a method of bypassing a TH2-type immune reaction favored by inherent immune stimulatory characteristics of an adjuvant present in an immunogenic complex containing an antigen comprising conjugating the antigen to a plant virus and administering the resultant immunogenic complex to an animal.

The invention additionally provides a method of treating an animal for an infectious disease by the stimulation of a TH1-biased immune response comprising conjugating an antigen associated with the infectious agent to a plant virus and administering the resultant immunogenic complex to the animal.

Also, the invention provides a method of treating an animal for an allergy by the stimulation of a TH1-biased immune response comprising conjugating an antigen derived from the cognate allergen associated with the allergy to a plant virus and administering the resultant immunogenic complex to the animal.

In addition, the invention discloses a method of treating an animal suffering from cancer by the stimulation of a TH1-biased immune response comprising conjugating an antigen associated with the cancer to a plant virus and administering the resultant immunogenic complex to the animal.

Furthermore, provided herein is a method for inducing a shift in an extant TH2-type immune response to an antigen present in one immunogenic complex used to prime an immune response in an animal which comprises inoculating an animal with an immunogenic complex containing that antigen conjugated to a plant virus particle in a secondary or subsequent booster dose.

DEFINITIONS

To facilitate understanding of the invention, a number of terms are defined below.

The terms “antigen” and “antigenic” refer to any substance that is specifically recognized by antibody or a T cell receptor. Antigens contain one or more epitopes (also referred to as “antigenic determinants”). An “epitope” is a structure on an antigen that interacts with the binding site of an antibody or T cell receptor as a result of molecular complementarity. An epitope may compete with the intact antigen, from which it is derived, for binding to an antibody. Generally, secreted antibodies and their corresponding membrane-bound forms are capable of recognizing a wide variety of substances as antigens, whereas T cell receptors are capable of recognizing only fragments of proteins that are complexed with MHC molecules on cell surfaces. Antigens recognized by immunoglobulin receptors on B cells are subdivided into three categories: T cell-dependent antigens, type 1 T cell-independent antigens; and type 2 T cell-independent antigens. An antigen may contain one or more of the following molecules: a peptide, polysaccharide, nucleic acid sequence, and lipid.

The terms "immunogen," "immunogenic," and "immunologically active" refer to any substance that is capable of inducing a specific humoral or cell-mediated immune response. By definition, an immunogen must contain at least one epitope, and generally contains several epitopes. Immunogens are exemplified by, but not restricted to, molecules that contain a peptide, polysaccharide, nucleic acid sequence, and/or lipid. Complexes of peptides with lipids, polysaccharides, or nucleic acid sequences are also contemplated, including (without limitation) glycopeptide, lipopeptide, glycolipid, etc. These complexes are particularly useful immunogens where smaller molecules with few epitopes do not stimulate a satisfactory immune response by themselves.

The term "allergen" refers to an antigen or immunogen that induces one or more hypersensitivity (allergic) reactions, exemplified by, but not limited to, the production of IgE antibodies. Allergens include, but are not restricted to, pollens of ragweed, grasses, or trees, or those of fungi, animal danders, house dust, or foods. Individuals exposed to an allergen generally, though not necessarily, develop hives or the manifestations of hay fever or asthma.

The term "adjuvant" as used herein refers to any compound that, when injected together with an antigen, non-specifically enhances the immune response to that antigen.

The term "excipient" refers herein to any inert substance (for example, gum arabic, syrup, lanolin, starch, etc.) that forms a vehicle for delivery of an antigen. The term excipient includes substances that, in the presence of sufficient liquid, impart to a composition the adhesive quality needed for the preparation of pills or tablets.

The terms "antibody" and "immunoglobulin" are interchangeably used to refer to a glycoprotein evoked in an animal by an immunogen. An antibody demonstrates specificity to the immunogen or, more specifically, to one or more epitopes contained in the immunogen.

Native antibody comprises at least two light polypeptide chains and at least two heavy polypeptide chains. Antibodies may be polyclonal or monoclonal. The term "polyclonal antibody" refers to immunoglobulin produced from more than a single clone of plasma cells; in contrast, "monoclonal antibody" refers to immunoglobulin produced from a single clone of plasma cells.

The term "isotype" or "class" when made in reference to an antibody refers to an antibody class that is encoded by a particular type of heavy chain constant region gene. Thus, different antibody isotypes differ in the amino acid sequence of the heavy chain constant ($C_H$) region. Several antibody isotypes are known, including IgA, IgD, IgG, IgE, and IgM. Thus, IgG possesses γ heavy chain constant domain (Cγ); IgM possesses μ heavy chain constant domain (Cμ); IgA possesses ∝ heavy chain constant domain (C∝); IgD possesses δ heavy chain constant domain (Cδ); and IgE possesses ϵ heavy chain constant domain (Cϵ). Different antibody classes exhibit different effector functions and display different tissue localization. Each antibody class can be expressed as a membrane (m) or a secreted (s) form that differs in sequence at the carboxyl terminus of the heavy chain. Most antigens elicit prompt serum expression of IgM, followed later by a secondary isotype switching response in which products of downstream heavy chain genes, such as Cγ1 and Cγ2a predominate. The antibody isotype that predominates generally depends on the type of antigen (for example, polypeptide, polysaccharide, etc.) used to elicit production of the antibody.

The terms "subtype" and "subclass" when made in reference to an antibody isotype interchangeably refer to antibodies within an isotype that contain variation in the heavy chain structure. For example, the human IgG class contains the four isotypes $IgG_1$, $IgG_2$, $IgG_3$, and $IgG_4$, while the mouse IgG isotype contains the four subtypes $IgG_1$, $IgG_2a$, $IgG_2b$, $IgG_3$. Human IgA isotype contains $IgA_1$ and $IgA_2$ subtypes. The genes coding for the constant heavy chain have been mapped in mouse and are located on chromosome 12 in the order (from the 5' end) Cμ-Cδ-Cγ3-Cγ1-Cγ2b-Cγ2a-Cϵ-C∝ corresponding to isotypes IgM, IgD, $IgG_3$, $IgG_1$, $IgG_2b$, $IgG_2a$, IgE and IgA.

The term "isotype switching" refers to the phenomenon by which one antibody isotype (for example, IgM) changes to another antibody isotype (for example, IgG). Similarly, the term "subtype switching" refers to the phenomenon by which an antibody subtype (for example, $IgG_1$) changes to another subtype (for example, $IgG_2a$) of the same antibody isotype.

The term "effector functions" as used herein in reference to an antibody refers to non antigen-binding activities that are mediated by the antibody molecules and that are executed through the constant heavy chain region of the molecule. Effector functions are exemplified by receptor-binding on immune cells, complement fixation, etc. Effector functions facilitate the removal of antigen from the body by means of complement-mediated lysis or phagocytosis.

The terms "specific binding" or "specifically binding" when used in reference to the interaction of an antibody and an antigen means that the interaction preferably shows a preference for, and more preferably is dependent upon, the presence of a particular structure (that is, the antigenic determinant or epitope) on the antigen; in other words, the antibody is recognizing and binding to a specific antigen structure (including related structures) rather than to antigens in general. For example, if an antibody is specific for epitope "A," the presence of an antigen containing epitope A (or free, unlabeled A) in a reaction containing labeled "A" and the antibody will reduce the amount of labeled A bound to the antibody.

As used herein, the term "immunogenically effective amount" refers to that amount of an immunogen required to invoke the production of antibodies in a host upon vaccination. It is preferred, though not required, that the immunologically effective amount is a "protective" amount. The terms "protective" and "therapeutic" amount of an immunogen refer to that amount of the immunogen that diminishes one or more undesirable symptoms that are associated with exposure of the host animal to the immunogen. The terms to "diminish" and "reduce" symptoms as used herein in reference to the effect of a particular composition or of a particular method is meant to reduce, delay, or eliminate one or more symptoms as compared to the symptoms observed in the absence of treatment with the particular composition or method. As used herein, the term "reducing" symptoms refers to decreasing the levels of one or more symptoms. The term "delaying" symptoms refers to increasing the time period between exposure to the immunogen and the onset of one or more symptoms.

The term "eliminating" symptoms refers to completely "reducing" and/or completely "delaying" one or more symptoms.

The term "animal" refers to any animal whose antibodies, or T cell receptors, are capable of specifically recognizing an antigen. Alternatively, the term "animal" includes any animal that is capable of inducing a specific humoral or cell-mediated immune response to an immunogen. Preferred animals include, but are not limited to, mammals such as rodents, humans, primates, ovines, bovines, ruminants, lagomorphs, porcines, caprines, equines, canines, felines, aves, etc. Preferred animals are selected from the "order Rodentia" that refers to rodents, that is, placental mammals (class Euthria), which include the family Muridae (for example, rats and mice), most preferably mice. The terms "nucleic acid sequence" and "nucleotide sequence," as used herein, refer to an oligonucleotide or polynucleotide, and fragments or portions thereof, and to DNA or RNA of genomic or synthetic origin that may be single- or double-stranded, and represent the sense or antisense strand.

The terms "amino acid sequence," "peptide," "peptide sequence," "polypeptide," and "polypeptide sequence" are used interchangeably herein to refer to a sequence of amino acids.

The terms "peptide of interest," "nucleotide sequence of interest," and "molecule of interest" refer to any peptide sequence, nucleotide sequence, and molecule, respectively, the manipulation of which may be deemed desirable for any reason by one of ordinary skill in the art. Exemplary molecules of interest include, but are not limited to, a peptide, glycopeptide, polysaccharide, lipopeptide, glycolipid, lipid, steroid, nucleic acid, etc.

The term "derived" when in reference to a peptide derived from a cancer cell as used herein is intended to refer to a peptide that has been obtained (for example, isolated, purified, etc.) from a cancer cell.

The term "biologically active" when applied to any molecule (for example, polypeptide, nucleotide sequence, etc.) refers to a molecule having structural, regulatory and/or biochemical functions of the naturally occurring molecule.

A peptide sequence and nucleotide sequence may be "endogenous" or "heterologous" (that is, "foreign"). The term "endogenous" refers to a sequence that is naturally found in the cell or virus into which it is introduced so long as it does not contain some modification relative to the naturally occurring sequence. The term "heterologous" refers to a sequence which is not endogenous to the cell or virus into which it is introduced. For example, heterologous DNA includes a nucleotide sequence that is ligated to, or is manipulated to become ligated to, a nucleic acid sequence to that it is not ligated in nature, or to that it is ligated at a different location in nature. Heterologous DNA also includes a nucleotide sequence that is naturally found in the cell or virus into which it is introduced and that contains some modification relative to the naturally occurring sequence. Generally, although not necessarily, heterologous DNA encodes heterologous RNA and heterologous proteins that are not normally produced by the cell or virus into which it is introduced. Examples of heterologous DNA include reporter genes, transcriptional and translational regulatory sequences, DNA sequences that encode selectable marker proteins (for example, proteins that confer drug resistance), etc.

The term "wild-type" when made in reference to a peptide sequence and nucleotide sequence refers to a peptide sequence and nucleotide sequence, respectively, that have the characteristics of that peptide sequence and nucleotide sequence when isolated from a naturally occurring source. A wild-type peptide sequence and nucleotide sequence is that which is most frequently observed in a population and is thus arbitrarily designated the "normal" or "wild-type" form of the peptide sequence and nucleotide sequence, respectively. In contrast, the term "modified" or "mutant" refers to a peptide sequence and nucleotide sequence that displays modifications in sequence and/or functional properties (that is, altered characteristics) when compared to the wild-type peptide sequence and nucleotide sequence, respectively. It is noted that naturally occurring mutants can be isolated; these are identified by the fact that they have altered characteristics when compared to the wild-type peptide sequence and nucleotide sequence.

The term "isolated" when used in relation to a molecule (for example, a nucleic acid sequence, amino acid sequence, etc.) refers to a molecule that is identified and separated from at least one contaminant molecule with which it is associated.

As used herein, the term "purified" refers to a molecule (for example, a nucleic acid sequence, amino acid sequence, etc.) that is removed from its natural environment, isolated, or separated. An "isolated" molecule is, therefore, a purified molecule. "Substantially purified" molecules are at least 60% free, preferably at least 75% free, and more preferably at least 90% free from other components with which they are associated.

The terms "pathogen" and "animal pathogen" refer to any organism that causes a disease in an animal. Pathogens include, but are not limited to, viruses, bacteria, protozoa, nematodes, fungus, etc.

The term "cancer cell" refers to a cell undergoing early, intermediate or advanced stages of multi-step neoplastic progression. The features of early, intermediate and advanced stages of neoplastic progression have been described using microscopy. Cancer cells at each of the three stages of neoplastic progression generally have abnormal karyotypes, including translocations, inversion, deletions, isochromosomes, monosomies, and extra chromosomes. Cancer cells include "hyperplastic cells," that is, cells in the early stages of malignant progression, "dysplastic cells," that is, cells in the intermediate stages of neoplastic progression, and "neoplastic cells," that is, cells in the advanced stages of neoplastic progression.

The term "modified plant virus" refers to a plant virus, any part of which has been modified by chemical, biochemical, and/or molecular biological techniques. A "chimeric plant virus" is a plant virus that has been modified by means of molecular biological techniques.

The terms "TH1-type response" and "TH1 response" when made in reference to a response in an animal refer to any cellular and/or humoral response that is generated by TH1 lymphocytes upon stimulation by an antigen, including, but not limited to, changes in the level of TH1-associated immunoglobulin, TH1 cell proliferation, and/or TH1-associated cytokine. In contrast, "TH2-type response" and "TH2 response" when made in reference to a response in an animal refer to any cellular and/or humoral response that is generated by TH2 lymphocytes upon stimulation by an antigen, including, but not limited to, changes in the level of TH2-associated immunoglobulin, TH2 cell proliferation, and/or TH2-associated cytokine.

The terms "TH1-associated immunoglobulin" and "TH1 cell-derived immunoglobulin" refer to one or more of the immunoglobulins (for example, IgG) that are generated by TH1 cells. In contrast, the terms "TH2-associated immunoglobulin" and "TH2 cell-derived immunoglobulin" refer to one or more of the immunoglobulins (for example, IgG) that are generated by TH2 cells. The subtypes of TH1-associated immunoglobulins and of TH2-associated immunoglobulins are species-specific in that they vary from species to species. For example, whereas in mouse, $IgG_2$ (and in particular, $IgG_{2a}$ and $IgG_{2b}$) is the principle TH1-associated immunoglobulin, in man, $IgG_1$ and $IgG_3$ are the TH1-associated immunoglobulins that perform TH1 functions. With respect to TH2-associated immunoglobulins, these include mouse $IgG_1$ and $IgG_3$, and human $IgG_2$. Methods for determining immunoglobulin subtypes are known in the art and also described herein using, for example, enzyme-linked immunosorbent assay (ELISA) techniques that employ coating sample wells with commercially available alkaline phosphatase (AP)-labeled anti-IgG conjugates (for example, alkaline phosphatase (AP)-conjugated goat anti-mouse $IgG_1$, $IgG_{2a}$, $IgG_{2b}$ or $IgG_3$ (Southern Biotechnologies Inc., USA)) for detection using p-nitrophenyl phosphate (PNPP, Sigma-Aldrich) as the substrate.

The terms "TH1-associated cytokine" and "TH1 cell-derived cytokine" refer to one or more of the cytokines produced by TH1 type cells, including, without limitation, interleukin-2 (IL-2), tumor necrosis factor-β (TNF-β), and interferon-γ (IFN-γ). In a preferred embodiment, the TH1-associated cytokine is FN-γ. In contrast, the terms "TH2-associated cytokine" and "TH2 cell-derived cytokine" refer to one or more of the cytokines produced by TH2 type cells, including, without limitation, interleukin-4 (IL-4), interleukin-5 (IL-5), interleukin-6 (IL-6), interleukin-9 (IL-9), interleukin-10 (IL-10), and interleukin-13 (IL-13). In a preferred embodiment, the TH2-associated cytokine is IL-4.

DESCRIPTION OF THE INVENTION

The present invention provides methods and compositions that are effective in modulating the nature and/or level of an immune response to a molecule exemplified by, but not limited to, an antigen or immunogen. In particular, the invention provides methods and means for effecting a TH1 bias in the immune response to molecules such as antigens or immunogens, and/or reducing a TH2 bias in the immune response to such molecules. More particularly, the invention provides methods and means for increasing a TH1 immune response that is directed against molecules that otherwise generally stimulate a TH2-type response. The invention further provides compositions and methods to reduce a TH2 immune response to molecules. Additionally provided herein are compositions and methods for altering (that is, increasing or decreasing) the level of TH1- and TH2-associated immunoglobulins, the level of proliferation of TH1- and TH2-associated cytokines, and the level of proliferation of TH1 and TH2 cells.

In a first aspect, the invention provides modified plant virus particles that are capable of presenting to cells of the immune system molecules that are effective as either immunogens or antigens for the generation of antibodies and/or cytokines. More particularly, molecules presented via the invention's modified plant virus particles stimulate a TH1-type response, more preferably to stimulate a predominant TH1-type response.

In a second aspect, the present invention discloses means to modulate the particular branch of T helper pathways to reduce or overcome an undesirable bias toward a TH2-type response that is inherent in certain molecules. More preferably, such modulation results in exclusively or predominantly a TH1-type response in an animal inoculated with the molecule.

In a third aspect, the invention discloses methods for modulating an immune reaction in the absence of extraneous immunomodulatory agents (for example, adjuvants, cytokines, etc.)

In a fourth aspect, methods for preventing, treating, or vaccinating against diseases (exemplified, but not limited to, infectious diseases, allergies, and cancer) are described.

More particularly, the invention discloses the use of non-replicating plant viruses as carriers of molecules (for example, antigens and immunogens).

Data presented herein shows that, surprisingly, immunization with modified plant viruses as a platform for molecule presentation results in plant virus-specific and molecule-specific TH1 cells. A profound bias towards a TH1-type immune response is shown herein using the exemplary CPMV to present peptides that are derived from a wide range of sources, including bacteria, virus, immunoglobulin, hormone, and cancer-associated cell surface protein. The bias in favor of a TH1-type immune response is demonstrated herein to be independent of the source of the molecule, the dosage of the molecule, the presence or absence of adjuvant, the nature of the immunomodulating activity of the adjuvant if present, the route of administration, and the genetic constitution (genotype) of the immunized animal. This result is surprising in view of the prior art's reports that the priming of TH cell subsets is affected by the strain of animal used, the identity of the antigen, the route of antigen delivery, and the immunization regimen. This result is also surprising in view of the non-replication nature of the invention's modified plant viruses and the prior art's reports that live viruses are required for a predominant TH1 response (Nguyen et al. (1994) supra).

A number of peptides are immunogenic when expressed on CPMV (McLain et al. (1995) AIDS Res Hum Retro 11:327; Dalsgaard et al. (1997) Nat. Biotechnol. 15:248; Brennan et al. (1999) Microbiol. 145:211; Brennan et al. (1999) J. Virol 73:930). Peptides derived from fibronectin-binding protein (FnBP) found in the outer membrane of *Staphylococcus aureus* and expressed on the surface of CPMV elicit predominantly peptide-specific $IgG_{2a}$ in C57BL/6 mice (Brennan et al. (1999) Microbiology 145:211), suggesting a TH1-bias in the responses to these particular chimeric virus particle (CVP)-expressed peptides inoculated into one strain of mice. However, no cellular (T cell) responses associated with this particular phenomenon are reported.

In particular, the invention discloses that, surprisingly, peptides derived from a wide range of sources, including bacteria, virus, immunoglobulin, hormone and cancer-associated cell surface protein, tend to generate much higher levels of peptide-specific $IgG_{2a}$ relative to levels of peptide-specific $IgG_1$ when displayed on the exemplary CPMV. This plant virus does not replicate in human cells and thus behaves like a whole inactive virus in a mammalian system. Of the different CVPs tested herein, six generated a predominance of peptide-specific $IgG_{2a}$ antibody over $IgG_{2b}$ antibody, while only CPMV-MAST1 seemed to favor $IgG_{2b}$ production over that of $IgG_{2a}$ under certain conditions. The CPMV-specific antibody responses also showed the same predominance of $IgG_{2a}$ over $IgG_1$. At the cellular level, much higher numbers of both peptide- and CPMV-specific $IgG_{2a}$-producing spot forming cells (SFCs) (B cells) were produced compared to $IgG_1$-producing SFCs in the spleens of CVP-immunized mice.

While an understanding of mechanism is not required, and without intending to limit the invention to any particular mechanism, the strong polarization of the isotype response to both the peptide and virus in favor of a TH1-type response appears to be related to the ability of the virus to prime virus-specific CD4+ TH1, thereby facilitating the class-switching of peptide- (and virus)-specific naive B cells to TH1-associated immunoglobulin-producing plasma cells.

The predominance of peptide-specific $IgG_{2a}$ over $IgG_1$ is demonstrated herein in five different inbred mouse strains encompassing the $H-2^b$ (C57BL/6), $H-2^d$ (BALB/c), $H-2^q$ (NIH), $2^{dql}$ (Biozzi AB/H), and $H-2^s$ (DBA/1). Even in the TH2-biased BALB/c and Biozzi AB/H mice (Natsuume-Sakai et al. (1977) Immunology 32:861; Sant'Anna et al. (1985) Immunogenetics 22:131), $IgG_{2a}$ surprisingly predominated over $IgG_1$. Adjuvants tested herein with the CVPs included those that favor TH1 responses, such as Freund's Complete Adjuvant, and those that favor TH2 responses (alum and QS-21: Cooper (1994) "The Selective Induction of Different Immune Responses by Vaccine Adjuvants," in Vaccine Design (G. I. Ada., ed.), R. G. Landes Company, pp. 125). Again, levels of $IgG_{2a}$ generated using these adjuvants or in the absence of adjuvant were surprisingly much higher than levels of $IgG_1$, highlighting that it is indeed the carrier plant virus rather than the adjuvant that is driving the TH1 responses. Importantly, unlike the case with the animal viruses described above, the predominance of $IgG_{2a}$ over $IgG_1$ was observed irrespective of the mouse strain or the adjuvant used for immunization.

The invention further discloses that immunization of both high and low doses (ranging from 2-300 μg) of CVPs led to the generation of TH1-type responses. Thus, the dose over three orders of magnitude of administered antigen, previously shown to influence the generation of mouse IgG isotypes (Hocart et al (1989) J. Gen. Virol. 70:2439; Hocart et al. (1989) J. Gen. Virol. 70:809) surprisingly did not appear to affect the TH1 bias in the isotypes of peptide-specific IgG.

The results obtained with the exemplary icosahedral plant viruses described herein were surprising because, in part, other icosahedral virus-like particles (VLPs) derived from animal viruses, such as Norwalk virus (Ball et al. (1998) J. Virol 72:1345) and rotavirus (O'Neal et al. (1997) J. Virol. 71:8707), do not elicit such a strong predominance of $IgG_{2a}$ over $IgG_1$ as that reported here. It is reported elsewhere that targeting of particulate antigens to macrophages is not sufficient in itself to stimulate a polarized TH1 response (Sedlik et al. (1997) Intl. Immunol. 9:91) since co-immunization with immune-modulators such as IL-12 and poly(1):(C) is required.

The compositions and methods of the invention are useful in generating antibodies to a molecule, in inducing a desirable TH1-type response and/or reducing an undesirable TH2-type response to a molecule for the purpose of, for example, detecting, preventing, and/or treating diseases. In particular, the modified plant viruses of the invention find particular (although not exclusive) use in clinical applications since their immunomodulatory effects may be achieved in the absence of extraneous immunomodulatory agents (such as cytokines and adjuvants), thereby avoiding the expense and adverse side effects that are associated with administration of these agents. Moreover, because the modified plant viruses of the invention do not replicate in human cells, they represent an advantage over existing vaccine carriers since they avoid safety concerns that are implicated in the existing live animal viruses/bacteria and DNA carrier systems.

The invention is further described under (A) Development of TH1/TH2 Cells, (B) TH1-Type and TH2-Type Responses and Pathology, (C) Plant Viruses, (D) Molecules of Interest, (E) Expression of Polypeptides by Plant Viruses, (F) Conjugating Molecules to Plant Viruses, (G) Administering Compositions to Animals, (H) Increasing a TH1-Type Response, and (D) Reducing a TH2-Type Response.

A. Development of TH1/TH2 Cells

In mice, naive CD4+ T cells are classified into two groups, TH1 and TH2, that are characterized by differential cytokine secretion profiles and hence distinct effector functions (for review see Mosmann et al. (1986) J. Immunol. 136:2248-2357). While an understanding of mechanism is not necessary to practice the invention, and without limiting the invention to any particular mechanism, T cell clones which demonstrate the archetypal TH1 or TH2 properties may be extremes of a continuum of differentiated CD4+ cells and the in vivo cytokine profile that is produced in a "typical" TH1 or TH2 response is produced by a spectrum of cell types.

However, for simplicity, it is easier to refer to the two cell types as if they are separable entities. Thus, the term "TH1 cell" as used herein refers to a T helper cell that produces one or more TH1-associated immunoglobulins (for example, mouse $IgG_{2a}$, mouse $IgG_{2b}$, human $IgG_1$, and human IgG3) and/or one or more TH1-associated cytokines (for example, IL-2, TNF-β, and IFN-γ). In contrast, a "TH2 cell" as used herein refers to a T helper cell that produces one or more TH2-associated immunoglobulins (for example, mouse $IgG_1$, mouse $IgG_3$, and human $IgG_2$) and/or one or more TH2-associated cytokines (for example, IL-4, IL-5, IL-6, IL-9, IL-10, and IL-13).

TH1 and TH2 cells develop from a common pool of naive CD4+ cells. Several factors may influence TH cell differentiation into the polarized TH1 or TH2 pathway. The cytokine profile of "natural immunity" evoked by different agents, the nature of the peptide ligand, the identity and level of microenvironmentally secreted hormones, the levels of antigen, and the presence on the T cells of co-stimulatory signaling receptors and MHC genotype can determine the development of the subsets, with TH2 cells being more dependant on high levels of antigen and the presence of co-stimulatory molecules. For example, the prior art has observed that, in mouse vaccination models, several factors influence which TH cell subsets are primed and the generation of specific mouse IgG isotypes. Such factors include the genetic background of the mouse strain used, the route of antigen delivery and the immunization regimen (including antigen quantity and half life), and the nature of the antigen. TH2-type cytokine profiles often appear later than TH1 responses in vivo.

The key cytokine for TH1 generation is believed to be IL-12, produced by activated macrophages and dendritic cells. The key cytokine for TH2 generation is believed to be IL-4. IL-4 is produced in small amounts during initial T cell activation (a particular subset of CD4 cells called the NK1.1 cell has been suggested as the initial source of IL-4 production). The development of a TH2 response is believed to be driven by development of local concentrations of IL-4, possibly as a result of persistent T cell stimulation.

With respect to the function of TH1 cells, these cells produce interleukin-2 (IL-2), interferon-γ (IFN-γ) and tumor necrosis factor-β (TNF-β), which mediate macrophage and cytotoxic T cell activation (CTL) and are the principle effectors of cell-mediated immunity against intracellular microbes and of DTH (delayed-type hypersensitivity) reaction (Mosmann et al. (1986), supra). CTL reactions are increasingly recognized as important therapeutic factors in the treatment of, or response to, solid tumors. IFN-γ, produced by TH1 lymphocytes, also induces B cell isotype class-switching to the $IgG_{2a}$ subclass, which is the principal effector isotype of mouse IgG. $IgG_{2a}$ (and to a lesser extent $IgG_{2b}$) enhances antibody-dependent cell-mediated cytotoxicity (ADCC) (Huesser et al. (1977) J. Exp. Med. 146:1316) and strongly binds Clq of the classical complement pathway, which opsonizes cells or antibody clusters for phagocytosis (Klaus et al. (1979) Immunology 38:687). In man, $IgG_1$ and $IgG_3$ mediate these functions. Thus, as a result of these effector functions, $IgG_{2a}$ better protects mice against virus infections, tumors (Kaminski et al. (1986) J. Immunol. 136:1123) and parasites (Wechsler et al. (1986) J. Immunol. 137:2968) and enhances bacterial clearance (Zigterman et al. (1989) Infect. Immun. 57:2712).

In contrast to TH1 cells, TH2 cells produce interleukin-4 (IL-4), interleukin-5 (IL-5), interleukin-10 (IL-10) and interleukin-13 (IL-13), which suppress cell-mediated immunity (Mosmann et al. (1986), supra). IL-4 induces B cells to produce $IgG_1$, which in mice poorly fixes complement and does not mediate ADCC (Klaus et al. (1979) Immunology 38:687). It also induces the production of immunoglobulin E (IgE), which binds to mast cells and basophils. Consequently, TH2 cells are mainly responsible for phagocyte independent host defense against, for example, helminthic parasites (Sher et al. (1992) Ann. Rev. Immunol. 10:385) and in the development of allergic reactions (Erb et al. (1996) Immunol. Cell Biol. 74:206).

B. TH1-Type and TH2-Type Responses and Pathology

A number of factors (for example, type of antigen, genetic background of the host animal, route of administration, choice of adjuvant) are reported by the prior art to dictate the nature and extent of an immune response elicited by the exposure of a molecule to an animal's immune system. For example, murine antibody responses to soluble proteins and to carbohydrates are generally restricted to the $IgG_1$ and $IgG_3$ subclasses, respectively. This suggests that IgG isotypes are not randomly selected. Indeed, live viruses (including a range of RNA and DNA viruses) preferentially induce the production of specific $IgG_{2a}$ antibodies (Coutelier et al. (1987) J. Exp. Med. 165:64). It is argued that the infection process generated by live viruses may be crucial for the production of IFN-γ that preferentially elicits virus-specific TH1 responses and the predominance of virus-specific $IgG_{2a}$ (Nguyen et al. (1994) J. Immunol. 152:478). This may also explain why replicating (live) bacterial and DNA vaccines generate TH1-biased responses (Londono et al. (1996) Vaccine 14:545; Pertmer et al. (1996) J. Virol. 70:6119). However, it is known that some live viruses, such as influenza virus (Balkovic et al. (1987) Antiviral Res. 8:151), herpes simplex virus type I (HSV-1; McKendall et al. (1988) J. Gen Virol 69:847), Theiler's murine encephalomyelitis virus (Peterson et al. (1992) Immunology 75:652) and foot-and-mouth disease virus (Perez-Filgueira et al. (1995) Vaccine 13:953) elicit predominant isotypes other than $IgG_{2a}$. In addition to the nature of antigen, the genetic background of the host animal influences the nature and extent of an immune response. Thus, in the case of influenza virus, BALB/c mice produce predominantly $IgG_{2a}$ yet C57Ba1/6 mice produce predominantly $IgG_1$ (Hocart et al. (1989) J. Gen. Virol. 70:2439). Thus, the immune reaction against these live viruses is sensitive to a genetic element (immunogenomic factor).

The nature of the adjuvant also plays a role in determining the nature of the immune response. For foot-and-mouth disease virus (FMDV), $IgG_{2b}$ is the predominant isotype produced to both live and inactive whole virus, except when a water-in-oil adjuvant is used with the inactive virus. With the latter adjuvant combination, a predominance of $IgG_{2a}$ (Perez-Filgueira et al. (1995) Vaccine 13:953) results. Hence, the choice of adjuvant can clearly influence the branch of the T helper response.

Furthermore, some inactivated viruses can elicit predominantly $IgG_{2a}$ antibodies. So, overall, a variety of studies shows that the ability to elicit virus-specific $IgG_{2a}$ may not simply be due to the infection process, but may also be dependent on the nature of the virus itself, the H-2 haplotype of the mouse, the route of immunization and also on the choice of adjuvant.

The cytokine profiles generated by the TH1- and TH2-type T cells lead to differing physiological responses to pathogens that seek to reduce, ameliorate or remove the pathogen burden. However, tissue damage can also occur due to persistent or overreaction to the pathogen.

In particular, in the case of TH1, the recruitment and activation of macrophages can lead to undesirable granulomatous inflammation, the preeminent example being the tuberculoid form of leprosy. If the infecting microorganism is an intracellular organism like the ones that cause tuberculosis, brucellosis, or the organisms *Pneumocystis carini* (protozoan), a fungus like *Candida albicans* or *Leishmania major* (an intracellular parasite-protozoan), the TH1 response leads to a delayed-type hypersensitivity (DTH) response that results in the elimination of the cells containing these organisms. The release of IFN-γ in the vicinity of the infection activates macrophages. The localized release of lysosomal enzymes from the macrophage kills infected cells and healthy bystander cells, resulting in the destruction of the invading microorganism. In addition, there is a release by the TH1 cell of a protein called MIF (macrophage inhibition factor). This protein is an anti-chemotactic factor that renders immobile any macrophage in the TH1 cell's vicinity. Thus, macrophages remain at the site of the infection. The lung damage seen due to tuberculosis and perhaps to *Pneumocystis carinii* is the result of indiscriminate cell damage caused by active macrophages and lysosomal enzyme release into the tissue. TH1-dominated responses may also be involved in the pathogenesis of organ-specific autoimmune disorders, acute allograft rejection, unexplained recurrent abortions, contact dermatitis, and some chronic inflammatory disorders of unknown etiology (summarized by Romagnani (1996) Clin. Immunol. Immunopathol. 80:225).

Inappropriate TH2 responses also can result in undesirable results including recruitment of basophils and eosinophils that can have adverse consequences in the development of allergies and asthma. The response to an early form of the RSV (respiratory syncytial virus) vaccine (containing alum-conjugated killed virus vaccine) is an example of an inappropriate TH2 response that led to cases of eosinophilia and bronchospasm. Similar reactions can lead to asthmatic symptoms. TH2-type responses are also responsible for Omenn's syndrome, reduced protection against some intracellular pathogens, transplantation tolerance, chronic GVHD (graft-versus-host disease), atopic disorders, and some systemic autoimmune diseases.

It has been noted that altering the sequence (and hence affinity) of peptides within the MHC class II complex can affect the nature of the CD4+ T cell response (Murray (1998) Immunol. Today 19:157). Thus, peptide epitopes derived from proteins from infectious agents can become modified through evolution to cause the redirection of the host response to the pathogen, for example, between TH1 and TH2 responses. Parallel evolution of host and pathogen can result in the development of T epitopes on pathogens that bind with particular affinities to MHC subsets. The host response must be balanced to meet the requirements of detecting multiple pathogens and forms of pathogens. Therefore, a certain degree of sequence variation in immunogenic determinants of a pathogen might be expected to occur. To some extent, this represents one means by which the immunomodulation of a reaction to a particular immunogen might be contemplated, that is, the mutation of amino acids within a peptide to achieve a distinct type of immune reaction over that raised against the wild-type peptide.

C. Plant Viruses

The invention provides non-replicating modified plant virus particles that are capable of presenting to cells of the immune system molecules that are effective as either immunogens or antigens to generate antibodies and/or cytokines, stimulate a TH1-type response, preferably a predominant TH1-type response, reduce an undesirable bias toward an extant, or an expected, TH2-type response, which is inherent in certain molecules.

The invention contemplates the use of any virus in which the nucleic acid coding for the capsid is a separate moiety from that which codes for other functional molecules, and whose coat proteins have a β-barrel structure. An advantage of the use of viruses that have this structure is that the loops between the individual strands of β-sheet provide convenient sites for the insertion of foreign peptides. Modification of one or more loops is a preferred strategy for the expression of foreign peptides in accordance with the present invention. In one embodiment, the invention contemplates the use of comoviruses (such as CPMV and bean pod mottle virus), nepoviruses (such as tomato ringspot virus and strawberry latent ringspot virus), tombusviruses (such as tomato bushy stunt virus (TBSV)), and sobemoviruses (such as southern bean mosaic virus (SBMV)). In particular, the tombusviruses and sobemoviruses have similar three-dimensional structures to those of comoviruses and nepoviruses, but have a single type of β-barrel.

In a more preferred embodiment, the virus is a comovirus. An advantage of the comoviruses is that their capsid contains sixty copies each of three different β-barrels that can be individually manipulated, thus allowing expression of 60-180 copies of a peptide by a single virus particle.

Comoviruses are a group of at least fourteen plant viruses that predominantly infect legumes. Their genomes consist of two molecules of single-stranded, positive-sense RNA of different sizes that are separately encapsidated in isometric particles of approximately 28 nm diameter. The two types of nucleoprotein particles are termed middle (M) and bottom (B) component as a consequence of their behavior in caesium chloride density gradients, the RNAs within the particles being known as M and B RNA, respectively. Both types of particle have an identical protein composition consisting of 60 copies each of a large (VP37) and a small (VP23) coat protein. In addition to the nucleoprotein particles, comovirus preparations contain a variable amount of empty (protein-only) capsids, which are known as top (T) component. In a preferred embodiment, the comovirus is CPMV.

In the case of the exemplary member of the comovirus group, CPMV, it is known that both M and B RNA are polyadenylated and have a small protein (VPg) covalently linked to their 5' terminus. More limited studies on other comoviruses suggest that these features are shared by the RNAs of all members of the group. Both RNAs from CPMV have been sequenced and shown to consist of 3481 (M) and 5889 (B) nucleotides, excluding the poly (A) tails. Both RNAs contain a single, long open reading frame, expression of the viral gene products occurring through the synthesis and subsequent cleavage of large precursor polypeptides. Though both RNAs are required for infection of whole plants, the larger B RNA is capable of independent replication in protoplasts, though no virus particles are produced in this case. This observation, coupled with earlier genetic studies, established that the coat proteins are encoded by M RNA.

A 3.5 A electron density map of CPMV shows that there is a clear relationship between CPMV and the T-3 plant viruses, such as the tombusviruses, in particular, TBSV and the sobemoviruses, and in particular, SBMV. The capsids of these latter viruses are composed of 180 identical coat protein subunits, each consisting of a single β-barrel domain. These can occupy three different positions, A, B and C, within the virions. The two coat proteins of CPMV were shown to consist of three distinct P-barrel domains, two being derived from VP37 and one from VP23. Thus, in common with the T-3 viruses, each CPMV particle is made up of 180 β-barrel structures. The single domain from VP23 occupies a position analogous to that of the A type subunits of TBSV and SBMV, whereas, the N- and C-terminal domains of VP37 occupy the positions of the C and B type subunits, respectively (U.S. Pat. No. 5,874,087; incorporated herein in its entirety by reference).

X-ray diffraction analysis of crystals of CPMV and other members of the group, bean pod mottle virus (BPMV) shows that the 3-D structures of BPMV and CPMV are very similar and are typical of the comovirus group in general.

In the structures of CPMV and BPMV, each β-barrel consists principally of 8 strands of antiparallel β-sheet connected by loops of varying length. The flat β-sheets are named the B, C, D, E, F, G, H and I sheets, and the connecting loops are referred to as the βB-βC, βB-βE, βF-βG and βH-βI loops.

The comoviruses are also structurally related to the animal picornaviruses. The capsids of picornaviruses consist of 60 copies of each of three different coat proteins VP1, VP2 and VP3, each one consisting of a single β-barrel domain. As in the case of comoviruses, these coat proteins are released by cleavage of a precursor polyprotein and are synthesized in the order VP2-VP3-VP1. Comparison of the three-dimensional structure of CPMV with that of picornaviruses has shown that the N- and C-terminal domains of VP37 are equivalent to VP2 and VP3, respectively, and that VP23 is equivalent to VP1. The equivalence between structural position and gene order suggests that VP37 corresponds to an uncleaved form of the two picornavirus capsid proteins, VP2 and VP3.

One of the principal differences between the comoviruses and picornaviruses is that the protein subunits of comoviruses lack the large insertions between the strands of the β-barrels found in picornaviruses though the fundamental architecture of the particles is very similar. The four loops (βB-βC, βD-βE, βF-βG and (βH-βI) between the β-sheets are not critical for maintaining the structural integrity of the virions but, in accordance with this invention, are used as sites of expression of heterologous peptide sequences, such as exemplary antigenic sites that are derived from a wide range of sources including a bacterium, a virus, an immunoglobulin, a hormone, and a cancer-associated cell surface protein.

D. Molecules of Interest

The invention's modified plant virus particles are capable of presenting to cells of the immune system any molecule for the purpose of, for example, generating antibodies and/or cytokines, increasing a TH1-type response, and/or reducing a TH2-type response to the molecule. The antibodies that are generated in response to the invention's modified plant virus particles may be used to isolate and purify the molecule. Alternatively, these antibodies may be used to prevent, diagnose, or treat diseases that are associated with exposure of an animal to the molecule.

Molecules that are suitable for application in the instant invention include any molecule that is capable of being presented at an exposed portion of the coat protein of the invention's viruses. Exemplary molecules include, but are not limited to, those that contain a peptide sequence, nucleic acid sequence, polysaccharide, and/or lipid, such as glycopeptide, lipopeptide, glycolipid, etc.

Molecules that may be used to advantage in the instant invention include those that are purified but whose structure is unknown, as well as purified molecules of known structure (for example, peptides with known amino acid sequences, nucleic acid sequences with known nucleic acid sequences, polysaccharides of known composition and structure, etc.). In a preferred embodiment, the molecules are purified and of known structure.

Where the molecule is a peptide, it may be presented by the invention's modified viruses using molecular biological techniques to insert a nucleic acid sequence that encodes the peptide into the virus genome such that the peptide is expressed at an exposed portion of the coat protein of the invention's viruses (further described below). Alternatively, where the molecule is, or contains, a peptide sequence, nucleic acid sequence, polysaccharide, and/or lipid, such a molecule may be chemically conjugated to a reactive peptide expressed by a plant virus of the invention, as described below.

The invention contemplates polypeptide molecules that are derived from any source. Without intending to limit the scope thereof, the invention contemplates polypeptides that are derived from cancer cells and pathogenic parasites (for example, bacteria, viruses, protozoa, nematodes, fungi, etc.) and, in particular, antigenic and immunogenic peptides derived from these pathogenic parasites. Also included within the invention's scope are polypeptides that are associated with the development of disease, polypeptides that encode cytokines, polypeptide allergens, hormones, enzymes, growth factors, anti-idiotypic antibodies, receptors, adhesion molecules, and parts of any of the foregoing peptides or of precursors thereof.

Polypeptides that are derived from cancer cells that are contemplated to be within the scope of this invention are exemplified by, but not limited to, the esophageal cancer-associated antigen (U.S. Pat. No. 6,069,233), the mammary-specific protein (mammaglobin), which is associated with breast cancer (U.S. Pat. No. 5,922,836), the prostate mucin antigen, which is associated with prostate adenocarcinomas (U.S. Pat. No. 5,314,996), human prostate specific antigen (PSA) (U.S. Pat. Nos. 6,100,444; 5,902,725), the SF-25 antigen of colon adenocarcinoma (U.S. Pat. No. 5,212,085), urinary tumor-associated antigens (U.S. Pat. No. 5,993,828), melanogenic antigen (U.S. Pat. No. 6,087,110), the MART-1 melanoma antigen (U.S. Pat. No. 5,994,523), human tumor-associated antigen (PRAT) (U.S. Pat. No. 6,020,478), TRP-2 protein tumor antigen (U.S. Pat. No. 6,083,703), the human tumor-associated antigen (TUAN) (U.S. Pat. No. 5,922,566), and the tumor-specific T antigen, which is associated with virally induced tumors (U.S. Pat. No. 6,007,806). Each of the above-referenced U.S. patents is incorporated herein in its entirety by this reference.

Exemplary polypeptides that are derived from pathogenic bacteria include *Bordetella pertussis* antigens (U.S. Pat. Nos. 4,029,766; 5,897,867; 5,895,655), *Mycobacterium tuberculosis* antigens (U.S. Pat. No. 6,110,469), porin antigens from Bacterioides that are associated with ulcerative colitis and inflammatory bowel disease (U.S. Pat. No. 6,033,864), *Helicobacter pylori* antigens (U.S. Pat. No. 6,025,164), *Streptococcus* antigens associated with dental caries (U.S. Pat. No. 6,024,958), antigens derived from *Campylobacter jejuni* that are associated with diarrheal disease (U.S. Pat. No. 5,874, 300), the β-glycoprotein cell surface antigen that is correlated with multidrug resistance in mammalian species (U.S. Pat. No. 4,837,306), a pilus antigen present in adhesion-forming bacteria (U.S. Pat. No. 4,795,803), and *Moraxella catarrhalis* outer membrane vesicle antigens associated with pulmonary disease (U.S. Pat. No. 5,993,826). Each of the above-referenced U.S. patents is incorporated herein in its entirety by this reference.

Polypeptides that are derived from pathogenic viruses are illustrated by, but are not limited to, polypeptides that have been isolated and purified from viruses as exemplified by the rotavirus antigen (U.S. Pat. No. 6,110,724), Human Immunodeficiency Virus Type II (HIV-II,) antigens and Simian Immunodeficiency Virus (SIV) antigens (U.S. Pat. No. 5,268, 265), non-A, non-B hepatitis virus antigen (U.S. Pat. Nos. 4,702,909; 6,103,485), delta antigen of hepatitis D virus (U.S. Pat. No. 4,619,896), and influenza virus antigens (U.S. Pat. No. 6,048,537). Also included are viral polypeptides whose sequences are known, including, but not limited to, those derived from picornaviruses such as FMDV, poliovirus, human rhinovirus (HRV), and human papillomavirus (HPV) (U.S. Pat. No. 5,874,087), hepatitis C virus (HCV) antigen (U.S. Pat. No. 5,712,087), hepatitis B core antigen (U.S. Pat. No. 4,839,277), Epstein Barr virus-related antigens (U.S. Pat. No. 5,679,774), hepatitis V virus C33 antigen (U.S. Pat. No. 5,985,541), cytomegalovirus (CMV) antigens (U.S. Pat. No. 6,074,817), human immunodeficiency virus type 2 antigen (HIV-2) (U.S. Pat. No. 6,037,165), herpes simplex virus antigens (U.S. Pat. No. 6,013,433), and HTLV-I and HTLV-II antigens (U.S. Pat. No. 5,928,861). Each of the above-referenced U.S. patents is incorporated herein in its entirety by this reference.

Polypeptides within the scope of the invention, which are derived from pathogenic protozoa and nematodes include, for example, the peptide antigens derived from *Plasmodium vivax*, which causes malaria (U.S. Pat. No. 5,874,527), *Leishmania* antigens, which are associated with Leishmaniasis (U.S. Pat. No. 5,834,592), the antigens of the nematode parasite *Dirofilaria immitis* (U.S. Pat. No. 4,839,275), and antigens of *Anaplasma marginale*, which causes bovine anaplasmosis (U.S. Pat. No. 4,956,278). Each of the above-referenced U.S. patents is incorporated herein in its entirety by this reference.

Other polypeptides that are associated with the development of disease are also included within the scope of the invention. These include, but are not limited to, the exemplary GAGE tumor rejection antigen precursor that is associated with cancer development (U.S. Pat. No. 6,013,481), the antigens extracted from mammalian malpighian epithelia (for example, esophagus and epidermis) and associated with rheumatoid arthritis (U.S. Pat. No. 5,888,833), the Rh blood group antigens (U.S. Pat. No. 5,840,585), antigens indicative of the presence and progression of atherosclerotic plaque (U.S. Pat. No. 6,025,477), the IgG Fc-binding protein antigen associated with autoimmune diseases, such as ulcerative colitis, Crohn's disease, rheumatoid arthritis, and systemic lupus (U.S. Pat. No. 6,004,760), the Sm-D antigen associated with systemic lupus erythematosus (SLE) (U.S. Pat. No. 5,945, 105), monocyte antigens (U.S. Pat. No. 6,124,436), the antigen associated with autoimmune inner ear Meniere's disease (U.S. Pat. No. 5,885,783), the mesothelin differentiation-associated antigen, which is implicated in mesotheliomas and ovarian cancers (U.S. Pat. No. 6,083,502), the osteogenic and fibroblastic antigen (OFA) associated with bone-related diseases (U.S. Pat. No. 6,074,833), and the mast cell function-associated antigen (MAFA), which is associated with inflammatory and allergic reactions (U.S. Pat. No. 6,034,227). Each of the above-referenced U.S. patents is incorporated herein in its entirety by this reference.

Also included within the invention's scope are polypeptides that encode cytokines such as the exemplary interleukin-1α, interleukin-1β (U.S. Pat. Nos. 5,965,379; 5,955,476; 5,096,906), interleukin-2, interferon-α, interferon-γ, and tumor necrosis factor (U.S. Pat. No. 5,965,379), interleukin-6 (U.S. Pat. Nos. 5,965,379; 5,955,476; 5,942,220; 5,460,810), the TGF-β superfamily, which includes the TGF-β family (that is, including TGFβ1, TGFβ2, TGFβ3, TGFβ4, TGFβ5, and TGFβ1.2), the inhibin family (that is, including activins and inhibins), the DPP/VG1 family (that is, including bone marrow morphogenetic proteins (BMPs), DPP, and Vgl), and Mullerian Inhibiting Substance Family (that is, including Mullerian inhibiting substance (MIS)) (U.S. Pat. No. 5,830, 671), interleukin-11, leukemia inhibitory factor, oncostatin M, and ciliary neurotrophic factor (U.S. Pat. No. 5,460,810), and interleukin-12 (U.S. Pat. No. 5,955,476). Each of the above-referenced U.S. patents is incorporated herein in its entirety by this reference.

The invention also contemplates polypeptide allergens such as, but without limitation to, the vespid antigen 5, which is used to treat patients with vespid venom allergy (U.S. Pat. No. 6,106,844), the CRX JII *Cryptomeria japonica* major pollen allergens (U.S. Pat. No. 6,090,386), ryegrass pollen allergens Lol p lb.1 and Lol p lb.2 (U.S. Pat. No. 5,965,455), allergens of alder pollen, hazel pollen and birch pollen (U.S. Pat. No. 5,693,495), the house dust mite *Dermatophagoides farinae* Derf I and Derf II allergens, and *D. pteronyssinus* Der p I and Der p VII allergens (U.S. Pat. Nos. 5,958,415; 6,086, 897; 6,077,518; 6,077,517), cat allergen (Fel d I) (U.S. Pat. No. 5,547,669), cockroach (CR) allergens (U.S. Pat. No. 5,869,288), and peanut allergen (Ara h II) (U.S. Pat. No. 5,973,121). Each of the above-referenced U.S. patents is incorporated herein in its entirety by this reference.

Also included within the scope of the invention are polypeptide hormones that include, for example, parathyroid hormone (PTH), parathyroid hormone-related peptide (PTHrp), and their synthetic analogs (U.S. Pat. Nos. 5,693, 616 and 6,110,892), naturally occurring human growth hormone and its variants (U.S. Pat. Nos. 5,424,199; 5,962,411), avian growth hormone (U.S. Pat. No. 5,151,511), luteinizing hormone-releasing hormone (LHRH) and its analogues (U.S. Pat. No. 5,897,863), nuclear hormone receptor protein (U.S. Pat. No. 5,866,686), ecdysis-triggering hormone (U.S. Pat. No. 5,763,400), gonadotropin-releasing hormone (U.S. Pat. No. 5,688,506), and melanin-concentrating hormones (MCH) (U.S. Pat. No. 5,049,655). Each of the above-referenced U.S. patents is incorporated herein in its entirety by this reference.

Nucleic acid molecules within the scope of this invention include those that encode each of the polypeptide molecules described supra.

Molecules that contain a polysaccharide and that are within the scope of this invention are exemplified by polysaccharide and glycoprotein antigens derived from pathogenic parasites (in particular from bacteria), as well as glycoprotein hormones, such as follicle-stimulating hormone (FSH), luteinizing hormone (LH), and thyroid-stimulating hormone (U.S. Pat. Nos. 6,103,501; 5,856,137; 5,767,067; 5,639,640; 5,444, 167; each of which is hereby incorporated herein in its entirety by this reference).

Lipid-containing molecules that find use in this invention include, without limitation, those that are derived from pathogenic parasites (for example, lipoproteins, lipopolysaccharides, etc.).

In a particularly preferred embodiment, the molecule is a peptide. In a more preferred embodiment, the peptide is derived from a bacteria (for example, the OM protein F of *Pseudomonas aeruginosa* and the fibronectin-binding protein (FnBP) of *Staphylococcus aureus*), a virus (for example, canine parvovirus), an immunoglobulin (for example, human mIgE), a hormone (for example, human chorionic gonadotrophin), and a cancer-associated cell surface protein (for example, epithelial growth factor receptor).

E. Expression of Polypeptides by Plant Viruses

The plant viruses of the invention may be engineered in accordance with U.S. Pat. Nos. 5,874,087 and 5,958,422 (each incorporated herein in its entirety by this reference) to express peptides of interest that are derived from any source as described, supra. For example, the exemplary comoviruses (for example, CPMV) are capable of expressing externally from a single virus from 60 to 180 copies of a peptide (one peptide copy on each of the 60 copies of the small (S) coat protein and of the 60 copies of the large (L) coat protein).

The peptides that may be incorporated into the invention's modified plant viruses preferably contain at least four (4) amino acids and are subject only to the limitation that the nature and size of the peptide and the site at which it is placed in or on the virus particle do not interfere with the capacity of the modified virus to assemble when cultured in vitro or in vivo. While not intending to limit the invention to any type or source of peptide, in one embodiment, the peptide is one whose function requires a particular conformation for its activity. Biological activity of the peptide may be maintained by association of the peptide with a larger molecule (for example, to improve its stability or mode of presentation in a particular biological system) as previously described (U.S. Pat. No. 5,958,422; incorporated herein in its entirety by this reference).

The plant viral nucleic acid is modified by introducing a nucleotide sequence coding for the peptide of interest, either as an addition to (that is, insertion into) the existing viral genome or as a substitution for part of the viral genome. The choice of the method of introduction is determined largely by the structure of the capsid protein and the ease with which additions or replacements can be made without interference with the capacity of the modified virus to assemble in plants.

In one embodiment, the nucleotide sequence coding for the peptide of interest is inserted into the viral genome. In a first embodiment, the site of insertion of, or substitution with, the nucleotide sequence coding for the peptide of interest is selected such that direct sequence repeats flanking the site are absent. In the context of the present invention, the term "direct sequence repeat" when made in reference to a construct that contains a nucleotide sequence of interest means that an identical oligonucleotide sequence is present on both sides of the nucleotide sequence of interest. Constructs that contain direct sequence repeats flanking a nucleotide sequence of interest are undesirable because they are genetically unstable as a result of recombination between the flanking sequence repeats, leading to loss of the flanked nucleotide sequence and reversion to the wild-type sequence.

In an alternative embodiment, where the foreign oligonucleotide sequence is introduced into the plant virus genome as a substitution for part of the existing sequence, it is preferred that the substituted virus genome sequence does not encode an amino acid sequence in the viral coat protein, which is important for virus replication, encapsidation, and/ or propagation in a host plant. This defect may be readily determined and avoided using methods known in the art in combination with the teachings herein.

The nucleotide sequence encoding the peptide of interest may be introduced into the plant virus by identifying that part of the virus genome that encodes an exposed portion of a coat protein. The term "exposed portion of a coat protein" as used herein in reference to a virus is that part of the virus coat protein that is disposed on the outer surface of the coat protein. The location of portions of the coat protein that are exposed, and which are, therefore, potentially optimum sites for introduction of the polypeptide of interest, may readily be identified by examination of the three-dimensional structure of the plant virus. In a further embodiment, the amino acid sequence of the exposed portions of a coat protein is examined for amino acids that break α-helical structures because these are potentially optimum sites for insertion. Examples of suitable amino acids are proline and hydroxyproline, both of which interrupt the α-helix and create a rigid kink or bend in the structure whenever they occur in a polypeptide chain.

Once a suitable site in the virus coat protein is selected in accordance with the teachings above and those of U.S. Pat. Nos. 5,958,422 and 5,874,087 (each is incorporated herein in its entirety by this reference), the nucleotide sequence that encodes the peptide of interest may be introduced into the viral genome at a site that encodes the desired site. Such introduction may be achieved by either insertion into, or substitution for, a viral sequence.

Where insertion is desired, this may be achieved by selecting two different restriction enzyme sites and cleaving the nucleic acid using the selected restriction enzymes. A double-stranded nucleotide sequence that encodes the peptide of interest is synthesized using methods known in the art (for example, polymerase chain reaction, PCR) such that oligonucleotides terminate in ends that are compatible with the selected restriction enzyme sites, thus allowing insertion into the cleaved virus nucleic acid. This procedure results in the introduction of a nucleotide sequence coding for the peptide of interest while avoiding the presence of direct sequence repeats flanking the insert. Preferably, though not necessarily, complementary oligonucleotides are synthesized in which the sequence encoding the peptide of interest is flanked by plant virus sequences so that the nucleotide sequence of interest is introduced as an addition to the existing nucleic acid.

In a preferred embodiment, the plant virus is CPMV and the peptide of interest is inserted in the βB-βC loop in the small coat protein (VP23). This loop is clearly exposed on the surface of the viral particle, and computer modeling has shown that even large loops inserted at this site are unlikely to interfere with the interaction between adjacent subunits responsible for capsid structure and stability. This loop has a unique NheI site at position 2708 of the M RNA-specific sequence where foreign sequences may be inserted.

Alternatively, where substitution of a viral genome sequence is desired, the viral sequence that is selected for substitution is cleaved using appropriate restriction enzymes (for example, the sequence between the NheI and AatII restriction sites of the exemplary CPMV) and a nucleotide sequence encoding the peptide of interest is substituted therefor as previously described (U.S. Pat. No. 5,958,422).

Having determined the site and mode of introduction of the peptide of interest into the plant virus, manipulation of the plant virus may proceed using previously described methods (U.S. Pat. Nos. 5,958,422 and 5,874,087). For example, where the plant virus is an RNA virus (for example, CPMV), it is necessary to express the peptide of interest using cDNA clones of the RNA. cDNA clones of CPMV RNAs M and B have been constructed, in which the cDNA clone of the M RNA contains an inserted oligonucleotide sequence encoding a heterologous peptide, which make use of the cauliflower mosaic virus (CaMV) 35S promoter sequence linked to the 5' ends of the viral cDNAs to generate infectious transcripts in the plant. This technique overcomes some of the problems encountered with the use of transcripts generated in vitro and is applicable to all plant RNA viruses.

Referring specifically to manipulating the genome of the exemplary CPMV, a full-length cDNA clone of CPMV M RNA in the transcription vector pPM1 is available (pPMM2902), as is a full-length cDNA clone of CPMV B RNA(pBT7-123). A mixture of transcripts from pPMM2902 and pBT7-123 gives rise to a full virus infection when electroporated into cowpea protoplasts.

In order to avoid the creation of a direct repeat sequence flanking the insert, a second restriction enzyme cutting site may be created in the nucleotide sequence of the region of the CPMV genome encoding VP23. For example, a single silent base change (U to C) at position 2740 of the mRNA creates a unique AatII site at amino acid valine 27 (position 2735 of the nucleotide sequence). This may be achieved by site-directed mutagenesis of M13-JR-1 using methods described in U.S. Pat. No. 5,874,087. The creation of the AatII site enables the nucleotide sequence encoding the six amino acids from the native βB-βC loop in CPMV to be removed by digestion with NheI and AatII. The sequence can then be replaced by any sequence with NheI- and AatII-compatible ends.

Without intending to limit the invention to any type of plant virus, any mode of introduction of the peptide of interest into the virus, and/or any site of insertion in the virus, in a preferred embodiment, the plant virus is CPMV and the peptide of interest is inserted between the alanine 22 ($Ala^{22}$) and proline 23 ($Pro^{23}$) residues in the βB-βC loop of the small capsid protein (VP23) as previously described (U.S. Pat. No. 5,958,422).

F. Conjugating Molecules to Plant Viruses

The plant viruses of the invention may be modified to present any molecule of interest to the humoral and/or cellular components of the immune system by chemically conjugating the molecule of interest to the plant virus as described below.

The term "conjugating" when made in reference to a molecule of interest and a virus as used herein means covalently linking the molecule of interest to the virus subject to the single limitation that the nature and size of the molecule of interest and the site at which it is covalently linked to the virus particle do not interfere with the capacity of the modified virus to assemble when cultured in vitro or in vivo.

1. Reactive Peptide

In one embodiment, the invention contemplates conjugating molecules of interest to the virus at an exposed portion of the virus coat protein. This may be achieved by conjugating the molecule of interest to a wild-type reactive peptide of the plant virus or, alternatively, to a heterologous reactive peptide that is expressed on the surface of the virus coat protein. In a preferred embodiment, the molecule of interest is conjugated to a heterologous reactive peptide that is expressed on an exposed surface of the plant coat protein.

The term "reactive peptide" refers to a peptide (whether wild-type or heterologous) that is capable of covalently binding to the molecule of interest. The term "capable of covalently binding" when made in reference to the interaction between a peptide and a molecule of interest means that the peptide covalently binds to the molecule in the presence of suitable conditions, such as suitable concentrations of salts, chemical reagents, temperature, pH, etc.

Reactive peptides of interest may range in size from 1 to 100, more preferably from 1 to 50, yet more preferably from 1 to 20 amino acids. Notably, it has been established that at least 38 amino acid residues may be displayed at the surface of the exemplary CPMV (U.S. Pat. Nos. 5,958,422 and 5,874,087).

While not intending to limit the amino acids in the reactive peptide to any particular type of amino acid residue, in one preferred embodiment, the reactive peptide contains one or more "reactive amino acids," that is, amino acids that are capable of forming a covalent linkage with a molecule of interest either directly or indirectly, for example, via a bifunctional molecule that is capable of covalent linkage with both the reactive amino acid and the molecule of interest. In a preferred embodiment, the reactive amino acid is a charged amino acid. A "charged amino acid" is an amino acid that contains a net positive charge or a net negative charge. "Positively charged amino acids," which are also referred to as "basic amino acids," include lysine, arginine, and histidine. "Negatively charged amino acids," which are also referred to as "acidic amino acids," include aspartic acid, glutamic acid, and cysteine. Given the sensitivity of the invention's plant viruses to the presence of destabilizing charged residues at the capsid surface, it is preferred, though not required, that the level of charge on the reactive peptide is minimized. This may be achieved by including both negatively charged and positively charged amino acids into the reactive peptide, such that the negative charge on the negatively charged amino acids is at least partially counter-balanced (that is, neutralized) by the positive charge on the positively charged amino acids, so that the reactive peptide has a net positive or negative charge. In a more preferred embodiment, the negative charge on the negatively charged amino acids is completely counter-balanced by the positive charge on the positively charged amino acids, such that the reactive polypeptide possesses a net charge of zero.

The charged amino acids of the reactive peptide may be contiguous (that is, two or more charged amino acids arranged in the absence of intervening uncharged amino acid residues or uncharged amino acid analogs) or non-contiguous (that is, two or more charged amino acids arranged with at least one intervening uncharged amino acid residue or amino acid analog). Contiguous charged amino acids may be composed of one (for example, Asp-Asp-Asp-Asp (SEQ ID NO:1); Arg-Arg-Arg; Lys-Lys-Lys-Lys-Lys (SEQ ID NO:2); or His-His) or more (for example, Asp-Glu; Cys-His-Lys; Lys-Arg-Arg, or Lys-Arg-His, or Lys-His-His) amino acid residues.

Where the charged amino acids are contiguous, they may be arranged such that the negatively charged amino acids are contiguous with respect to one another, and the positively charged amino acids are contiguous with respect to one another. Such a sequence is exemplified by, but not limited to, the positively charged sequences Lys-Lys-Arg-His-Lys (SEQ ID NO:3) and Arg-Arg-His-Lys (SEQ ID NO:4) and the negatively charged sequences Asp-Cys-Glu-Asp (SEQ ID NO:5) and Asp-Asp-Glu-Glu-Glu (SEQ ID NO:6). Alternatively, where the charged amino acids are contiguous, they may be arranged such that the negatively charged amino acids are non-contiguous with respect to one another, and/or the positively charged amino acids are non-contiguous with respect to one another.

A sequence of contiguous negatively charged amino acids may be contiguous to a sequence of contiguous positively charged amino acid as described by the formula XnYn, where X is a sequence of contiguous positively charged amino acids, Y is a sequence of contiguous negatively charged amino acids, and n is an integer from 1 to 50, more preferably from 1 to 25, yet more preferably from 1 to 10 amino acids. This is exemplified by the sequences Asp-Lys, Glu-Arg, Glu-Cys-Lys-Arg (SEQ ID NO:7), and Asp-Cys-Glu-His-Arg-Lys (SEQ ID NO:8).

Further, the sequence of contiguous charged amino acids may occur in the reactive peptide as a repeating sequence. The term "repeating sequence" when made in reference to an amino acid sequence that is contained in a peptide sequence means that the amino acid sequence is reiterated from 1 to 2 times, more preferably from 1 to 10 times, and most preferably from 1 to 100 times, in the peptide sequence. The repeats of the peptide sequence may be non-contiguous or contiguous. The term "non-contiguous repeat" when made in reference to a repeating peptide sequence means that at least one amino acid (or amino acid analog) is placed between the repeating sequences. The term "contiguous repeat" when made in reference to a repeating peptide sequence means that there are no intervening amino acids (or amino acid analogs) between the repeating sequences.

In one preferred embodiment, the reactive peptide contains a repeating sequence of contiguous positively charged amino acids as well as a repeating sequence of contiguous negatively charged amino acids, where the total number of positively charged amino acid residues in the sequence of contiguous positively charged amino acids is the same as the total number of negatively charged amino acid residues in the sequence of contiguous negatively charged amino acids. In a yet more preferred embodiment, the sequence of contiguous positively charged amino acids is contiguous with the sequence of contiguous negatively charged amino acids. This is exemplified by the sequences Asp-Lys-Asp-Lys-Asp-Lys-Asp-Lys-Asp-Lys-Asp-Lys (SEQ ID NO:9), Glu-Cys-Lys-Arg-Glu-Cys-Lys-Arg-Glu-Cys-Lys-Arg (SEQ ID NO:10), Asp-Cys-Glu-His-Arg-Lys-Asp-Cys-Glu-His-Arg-Lys (SEQ ID NO:11), Asp-Cys-Glu-His-Arg-Lys-Asp-Cys-Glu-His-Arg-Lys-Asp-Cys-Glu-His-Arg-Lys (SEQ ID NO:12), Cys-Asp-Asp-Glu-Cys-Lys-Arg-Arg-Arg-His-Cys-Asp-Asp-Glu-Cys-Lys-Arg-Arg-Arg-His-Cys-A sp-Asp-Glu-Cys-Lys-Arg-Arg-Arg-His (SEQ ID NO:13), Glu-Arg-Glu-Arg-Glu-Arg-Glu-Arg (SEQ ID NO:14), Asp-His-Asp-His-Asp-His-Asp-His-Asp-His (SEQ ID NO:15).

In an alternative preferred embodiment, the reactive peptide is contemplated to contain non-contiguous negatively charged amino acids and non-contiguous positively charged amino acids. In other words, the charged amino acids (whether negatively or positively charged) may have disposed between them amino acids (or amino acid analogs) that are either uncharged (for example, glycine, alanine, valine, leucine, isoleucine, serine, threonine, phenylalanine, tyrosine, tryptophan, methionine, proline, asparagine, and glutamine) or that have a different charge. In a more preferred embodiment, the reactive peptide further contains a sequence of contiguous charged amino acids, wherein the sequence of contiguous charged amino acids consists either of contiguous negatively charged amino acids or of contiguous positively charged amino acids. In a more preferred embodiment, the sequence is exemplified by a sequence of the general formula Asp-$Glu_n$-Gly-$Lys_n$-Asp-$Glu_n$ (SEQ ID NO:16), Asp-$Glu_n$-Gly-$Lys_{2n}$-Asp-$Glu_n$ (SEQ ID NO:17), Lys-$Arg_n$-Ser-Gly-Asp-Glu-Asp (SEQ ID NO:18), or Lys-$Arg_n$-His-Pro-Met-$Asp_n$-Glu (SEQ ID NO:19), where n is an integer of from 1 to 40. In yet a more preferred embodiment, the sequence is Asp-Glu-Gly-Lys-Gly-Lys-Gly-Lys-Gly-Lys-Asp-Glu (SEQ ID NO:20).

Any heterologous reactive peptide may be genetically engineered into a plant virus particle in accordance with the teachings above and those of U.S. Pat. Nos. 5,958,422 and 5,874,087. In particular, the heterologous reactive peptide may be expressed at an exposed portion of the coat protein of the plant virus. It is preferred that the reactive peptide be inserted into the plant virus particle such that the reactive amino acids are displayed on the coat protein of the plant virus, more preferably extending outwards from the structure of the capsid, thereby facilitating access by chemical ligands and reagent to the reactive amino acids of the reactive peptide. In one embodiment, the reactive peptide is inserted between alanine 22 and proline 23 of the small coat protein (VP-S) of CPMV.

2. Conjugating a Molecule of Interest to a Reactive Peptide

Any molecule of interest may be conjugated to a reactive peptide (whether wild-type or heterologous) that is displayed by the invention's plant viruses using methods known in the art. For example, methods for conjugating polysaccharides to peptides are exemplified by, but not limited to, coupling via alpha- or epsilon-amino groups to $NaIO_4$-activated oligosaccharide (Bocher et al. (1997) J. Immunol. Methods 27:191-202), using squaric acid diester (1,2-diethoxycyclobutene-3,4-dione) as a coupling reagent (Tietze et al. (1991) Bioconjug Chem. 2:148-153), coupling via a peptide linker wherein the polysaccharide has a reducing terminal and is free of carboxyl groups (U.S. Pat. No. 5,342,770), coupling with a synthetic peptide carrier derived from human heat shock protein hsp65 (U.S. Pat. No. 5,736,146), and using the methods of U.S. Pat. No. 4,639,512. These methods may be applied to polysaccharide antigens including, for example, the *Staphylococcus epidermidis* surface antigen (U.S. Pat. No. 5,961,975). Each of the above-referenced U.S. patents is incorporated herein in its entirety by this reference.

Methods for conjugating glycoproteins to peptides via the carbohydrate moieties of the glycoprotein have been described using, for example, the generation of reactive aldehydes on the carbohydrate moieties by mild oxidation with sodium periodate and subsequent reaction with peroxidase hydrazide (D'Alessandro et al. (1998) Clin. Chim. Acta 22:189-197), hetero-bifunctional cross-linking reagent 4-(4-N-melaeimidoPhenyl)butyric acid hydrazide HCl (MPBH), which allows coupling of carbohydrate-derived aldehydes to free thiols (Chamow et al. (1992) J. Biol. Chem. 267:15916-15922), the organic cyanylating reagent 1-cyano-4-dimethylamino pyridinium tetrafluoroborate (CDAP) to activate polysaccharides prior to coupling to peptides under mild alkaline conditions (pH 7-9) (Lees et al. (1996) Vaccine 14:190-198), carboxyl activation or hydroxyl activation of the polysaccharide (Devi et al. (1995) Infect. Immun. 63:2906-2911), alkali treatment of the polysaccharide prior to coupling to the peptide (Kabir (1987) J. Med. Microbiol. 23:9-18), and the methods of U.S. Pat. No. 4,639,512. These methods may be applied to, for example, conjugating glycoprotein antigens (exemplified by the human immunodeficiency virus type 2 (HIV-2) antigen (U.S. Pat. No. 6,037,165), and the P-glycoprotein cell surface antigen (U.S. Pat. No. 4,837,306)) to the plant virus. Each of the above-referenced U.S. patents is incorporated herein in its entirety by this reference.

Also, either the protein or polysaccharide moiety of a glycoprotein may be used to covalently link the glycoprotein to reactive peptides on the virus by using prior art techniques that have been applied to conjugation of glycoproteins to glycoproteins, such as by photoactivation to an azidobenzoyl derivative of one of the glycoproteins (Rathnam et al. (1980) Biochim. Biophys. Acta 624:436-442).

Methods for conjugating proteins to proteins are described herein (that is, conjugating a reactive heterologous peptide that contains a cysteine residue with a protein of interest that has been activated with n-maleimidobenzoyl-N-hydroxysuccinimide ester (MBS) Example 11). Several additional methods are also known, including the method of conjugating SL protein to protein allergens (Jahn-Schmid et al. (1996) Immunotechnology 2:103), coupling with a synthetic peptide carrier derived from human heat shock protein hsp65 (U.S. Pat. No. 5,736,146) the methods used to conjugate peptides to antibodies (U.S. Pat. Nos. 5,194,254; 4,950,480), the methods used to conjugate peptides to insulin fragments (U.S. Pat. No. 5,442,043), the methods of U.S. Pat. No. 4,639,512, and the method of conjugating the cyclic decapeptide polymyxin B antibiotic to an IgG carrier using EDAC (1-ethyl-3-(3-dimethylaminopropyl)carbodiimide)-mediated amide formation (Drabick et al. (1998) Antimicrob. Agents Chemother. 42:483-588). Each of the above-referenced U.S. patents is incorporated herein in its entirety by this reference.

Approaches to conjugate nucleic acids to proteins are also known in the art, such as those described in U.S. Pat. Nos. 5,574,142; 6,117,631; 6,110,687; each of which is incorporated herein in its entirety by this reference.

Methods for conjugating lipids to peptides have been described in the art including, but not limited to, the use of reductive amination and an ether linkage that contains a secondary or tertiary amine (U.S. Pat. No. 6,071,532), the methods of U.S. Pat. No. 4,639,512, the methods used for covalently coupling peptides to unilamellar liposomes (Friede et al. (1994) Vaccine 12:791-797), the use of coupling human serum albumin to liposomes using the hetero-bifunctional reagent N-succinimidyl-5-acetylthioacetate (SATA) (Kamps et al. (1996) Biochim. Biophys. Acta 1278:183-190), the use of coupling antibody Fab' fragments to liposomes using a phospholipid-poly(ethylene glycol)-maleimide anchor (Shahinian et al. (1995) Biochim. Biophys. Acta 1239:157-167), and the use of coupling *Plasmodium* CTL epitope to palmitic acid via cysteine-serine spacer amino acids (Verheul et al. (1995) J. Immunol. Methods 182:219-226). Each of the above-referenced U.S. patents is incorporated herein in its entirety by this reference.

G. Administering Compositions to Animals

In one embodiment, it is contemplated that the modified viruses of the invention are used for the presentation of antigenic molecules as the immunogenic component of vaccines. The invention's modified plant viruses provide an especially attractive epitope presentation system in the context of vaccine design since they present the antigenic molecule on the plant virus particle so that it is easily recognized by the immune system, for example, by location on an exposed part of the coat protein of the virus. The modified viruses of the invention may be administered to a recipient animal by any desired route (for example, intranasal, oral, parenteral, subcutaneous, intravenous, subcutaneous, intrathecal, intraperitoneal, intramuscular, etc.).

While data presented herein demonstrates that the modified plant viruses of the invention exert their effect on the cellular and/or humoral components of the immune system without regard to the absence or presence of extraneous immunomodulatory agents (for example, adjuvants, cytokines, etc.), the invention is expressly not limited to application of the invention in the absence of these agents. For example, because adjuvants function to enhance the nature of an immune response as well as the particular pathway of the resultant immune reaction, one of skill in the art may consider inclusion of adjuvants together with the modified viruses of the invention to be desirable, regardless of the influence which the adjuvant has on the T helper pathway elicited.

Though the invention was illustrated using the exemplary adjuvants alum, FCA/FICA, and QS-21, it is expressly contemplated that the invention not be limited to these adjuvants. Rather, any adjuvant of interest may be included, such as, but not limited to, those that contain an emulsion system and a synthetic resin material that is capable of complexing with antigens, hormones, drugs, and serum (U.S. Pat. No. 3,919,411), copolymers of polyoxyethylene/polyoxypropylene block copolymers (U.S. Pat. No. 6,086,899), 1H-imidazo[4,5-C]-quinolin-4-amine and its derivatives (U.S. Pat. No. 6,083,505), mutant *Escherichia coli* heat-labile enterotoxin holotoxin (U.S. Pat. No. 6,033,673), formyl methionyl peptide (fMLP) (U.S. Pat. No. 6,017,537), ADP-ribosylating exotoxin, which is particularly suitable for transcutaneous administration (U.S. Pat. No. 5,980,898), interleukin-12 (U.S. Pat. No. 5,976,539), polydimethylsiloxane and a complex emulsifier (U.S. Pat. No. 5,904,925), hemozoin or β-hematin (U.S. Pat. No. 5,849,307), *Saccharomyces cervisiae* glucan (U.S. Pat. No. 5,804,199), zinc hydroxide/calcium hydroxide gel, lecithin, and polyalphaolefin (U.S. Pat. No. 5,232,690), polyoxyethylene sorbitan monoesters (PS) that are useful for topical administration of antigens via mucosal membranes (U.S. Pat. No. 5,942,237), and transdermal liposomes (U.S. Pat. No. 5,910,306). Furthermore, methods of using the crystalline bacterial surface layers (SL) as adjuvants by conjugating antigens to SL are also known in the art (Jahn-Schmid et al. (1997) International Immunology 9:1867-1874). Each of the above-referenced U.S. patents is incorporated in its entirety by this reference.

Further, while not requiring cytokines or excipients for efficacy, the modified viruses of the invention may be co-administered using a cytokine or excipient of interest. Exemplary cytokines include, without limitation, interleukin-1α, interleukin-1β, interleukin-2, interleukin-11, interferon-α, interferon-γ, tumor necrosis factor, the TGF-β family, the inhibin family, the DPP/VG1 family, the Mullerian Inhibiting Substance Family, leukemia inhibitory factor, oncostatin M, and ciliary neurotrophic factor. Pharmaceutical excipients that may find use in combination with the invention's modified plant viruses include the illustrative microcrystalline cellulose-based excipient, which has improved compressibility (U.S. Pat. No. 6,103,219), galactomannan hydrocolloid, which is suitable for increasing the hardness rating of a pharmaceutical tablet containing guar gum (U.S. Pat. No. 6,063,402), cross-linked amylose, which is useful as an excipient for slow release of active compounds from tablets or pellets (U.S. Pat. No. 5,807,575), enzymatically debranched starches, which are compressible into a tablet (U.S. Pat. No. 5,468,286), and lipid vesicle excipients, which may be prepared in sprayable or droppable form for non-irritating delivery to nasal mucosa (U.S. Pat. No. 5,200,393). Each of the above-referenced U.S. patents is incorporated herein in its entirety by this reference.

H. Increasing a TH1-Type Response

The modified viruses of the invention find particular use in increasing a TH1 response to a molecule of interest, thus making the modified viruses of the invention particularly attractive carriers for molecules that target, for example, infectious disease, cancer, and allergy.

The terms "increasing the level of TH1 response" and "increased level of TH1 response" when made in reference to an animal's response to a modified virus containing a molecule of interest means that the level of any one or more of the cellular and/or humoral response that is generated by TH1 lymphocytes upon stimulation by the molecule or the virus is increased by any statistically significant amount as compared to the corresponding response in a control animal. In particular, an increased level of TH1 response in an animal that is exposed to a modified virus containing a molecule of interest refers to (a) an increased level of TH I-associated immunoglobulin, (b) an increased level of TH1-associated cytokine, and/or (c) an increased proliferation level of TH1 cells.

The term "increased level of TH1-associated immunoglobulin" in an animal that is exposed to a modified virus containing a molecule of interest refers to an increase, preferably at least 0.1%, more preferably from 0.1% to 50%, yet more preferably from 0.1% to 20%, and most preferably from 0.1% to 10%, in the quantity of one or more of the TH1-associated immunoglobulin subclasses (for example, mouse $IgG_{2a}$, mouse $IgG_{2b}$, human $IgG_1$, human $IgG_3$, etc.) that is specific for either the molecule of interest or for the virus, relative to the quantity of total TH1-associated immunoglobulin of the same subclass. For example, an increase of 5% in the quantity of molecule-specific (and/or virus-specific) mouse $IgG_{2a}$ relative to the quantity of total mouse $IgG_{2a}$ in the same mouse is considered an increase in the level of TH1 response in the mouse. Similarly, an increase of 1% in the quantity of molecule-specific (and/or virus-specific) mouse $IgG_{2b}$ relative to the quantity of total mouse $IgG_{2b}$ in the same mouse is considered an increase in the level of TH1 response in the mouse (see, for example, Table 4).

Alternatively, the term "increased level of TH1-associated immunoglobulin" in an animal that is exposed to a modified virus containing a molecule of interest refers to an increase, preferably at least a two-fold, more preferably from 2 to 100,000 fold, more preferably from 2 to 10,000 fold, and most preferably from 2 to 2,000 fold, in the ratio of the quantity of one or more of the TH1-associated immunoglobulin subclasses (for example, mouse $IgG_{2a}$, mouse $IgG_{2b}$, human $IgG_1$, human $IgG_3$, etc.) that is specific for either the molecule of interest or for the virus, relative to the quantity of total TH1-associated immunoglobulin of the same subclass, on the one hand, as compared to the ratio of one or more of the TH2-associated immunoglobulin subclasses (for example, mouse $IgG_1$, mouse $IgG_3$, human $IgG_2$, etc.), that is specific for either the molecule of interest or for the virus (respectively), relative to the quantity of total TH2-associated immunoglobulin of the same subclass, on the other hand. For example, an increase of 1,000 fold in the ratio of molecule-specific (and/or virus-specific) mouse $IgG_{2a}$:total $IgG_{2a}$, relative to the ratio of molecule-specific (and/or virus-specific) mouse $IgG_1$:total $IgG_1$ in the same mouse, is considered an increase in the level of TH1 response in the mouse. Similarly, an increase of 2,000 fold in the ratio of molecule-specific (and/or virus-specific) mouse $IgG_{2b}$:total $IgG_{2b}$, relative to the ratio of molecule-specific (and/or virus-specific) mouse $IgG_3$:total $IgG_3$ in the same mouse, is considered an increase in the level of TH1 response in the mouse (see, for example, Table 4).

In yet another alternative, the term "increased level of TH1-associated immunoglobulin" in an animal that is exposed to a modified virus containing a molecule of interest refers to an increase, preferably at least 2 fold, more preferably from 2 to 10,000 fold, yet more preferably from 2 to 1000 fold, even more preferably from 2 to 100 fold, and most preferably from 2 to 50 fold, in the geometric mean endpoint titer of molecule-specific (and/or virus-specific) TH1-associated immunoglobulins as compared to the geometric mean endpoint titer of the molecule-specific (and/or virus-specific) TH1-associated immunoglobulins in a control animal. The term "endpoint titer" is that dilution of antibody that is specific for a given molecule and that is the highest dilution of the antibody that produces a detectable reaction (for example, by ELISA) when combined with the molecule. For example, an increase of 20 fold in the geometric mean endpoint titer of molecule-specific mouse $IgG_{2a}$ in a treated mouse as compared to the geometric mean endpoint titer of the molecule-specific mouse $IgG_{2a}$ in a control mouse is considered an increased level of TH1-associated immunoglobulin (see, for example, Tables 2 and 3).

Methods for quantitating immunoglobulin levels produced by individual B cells (as well as cells fused with B cells such as hybridomas) are readily achieved in vitro using commercially available reagents and a variety of tests, including those described herein, such as ELISA and ELISPOT. See Segwick et al. (1983) J. Immunol. Methods 57:301-309. See also Mazer et al. (1991) J. Allergy Clin. Immunol. 88:235-243.

In yet another alternative, an "increased level of TH1 response" refers to an increase in the level of TH1-associated cytokine. The term "increase in the level of TH1-associated cytokine" in an animal that is exposed to a modified virus containing a molecule of interest means that the amount of a TH1-associated cytokine that is produced by the animal's TH1 cells is increased preferably by at least 2 fold, more preferably from 2 to 10,000 fold, yet more preferably from 2 to 1,000 fold, and most preferably from 1 to 100 fold, in a treated animal relative to the amount of TH1-associated cytokine that is produced by T cells of a control animal. The quantity of cytokines may be determined using, for example, ELISA, as described herein using commercially available reagents (for example, Table 6).

In a further alternative, an "increased level of TH1 response" refers to an increased proliferation level of TH1 cells. The term "increased proliferation level of TH1 cells" in an animal that is exposed to a modified virus containing a molecule of interest means that the number of proliferating TH1 cells that are produced by the animal is increased preferably by at least 2 fold, more preferably from 2 to 10,000 fold, more preferably from 2 to 1,000 fold, and most preferably from 1 to 100 fold, relative to the number of proliferating TH1 cells that are produced by a control animal. The number of proliferating TH1 cells may be determined using methods such as those described herein, and their TH1 type may be determined by examination of supernatants of these cells for the presence of TH1-associated cytokines (for example, Table 6).

In one embodiment, it is contemplated that a therapeutic amount of the modified plant viruses of the invention be administered to a subject.

Data presented herein demonstrates that immunization of mice with the exemplary chimeric virus particles (CVPs) of CPMV generates primarily CPMV- and peptide-specific $IgG_{2a}$ and $IgG_{2b}$ antibodies in sera as determined by ELISA. Enzyme-linked immunospot (ELISPOT) analysis confirmed the bias in the antibody responses toward the TH1-type, demonstrating that the CVPs can prime predominantly CPMV- and peptide-specific $IgG_{2a}$- and $IgG_{2b}$-producing B cells in a spleen. In contrast, only low levels of CPMV- and peptide-specific $IgG_1$ and $IgG_3$ antibody-producing B cells (products of the TH2 immune pathway) were detected, if at all.

Furthermore, the invention discloses that spleen cells (T cells) from CVP-immunized mice proliferated to CPMV in vitro, producing high levels of IFN-γ (a TH1-associated cytokine) but no detectable levels of IL-4 (a TH2-associated cytokine). This suggests that the CVPs elicit a TH1-type response to the viral carrier that, in turn, governs the isotype of the peptide-specific B cell responses. The bias in the response towards the TH1-type was unaffected by the nature of the antigen, the genetic background of the individual inoculated, the choice of adjuvant, or the dose or the regimen of doses of CVPs administered.

While data presented herein demonstrates that, in a preferred embodiment, the level of TH1-associated cytokine (for example, IFN-γ) increased in response to treatment with the modified viruses of the invention in the absence of a change in the level of TH2-associated cytokine (for example, IL-4) it is expressly contemplated that the invention is not limited to an increase in TH1-associated cytokine in the total absence of detectable levels of TH2-associated cytokine. Rather, the invention expressly includes within its scope an increase in the level of TH1-associated cytokine regardless of the change (if any) in the level of TH2-associated cytokine.

The above data demonstrates the ability of the invention's modified viruses, which do not infect or replicate in mammalian cells, to direct the immune response to expressed peptides toward the TH1 effector type without the need for extraneous immunomodulatory agents, such as adjuvants or cytokines, and represents an advantage of the invention's plant viruses as a vaccine carrier system.

Put another way, the modified viruses provided herein behave as inactive viruses in the context of a mammalian inoculation. While inactive viruses are predicted by the prior art to trigger a TH2 response, the inactive viruses provided herein surprisingly elicit a TH1-type response.

I. Reducing a TH2-Type Response

The modified viruses of the invention are useful in applications where it is desirable to reduce a TH2 response to a molecule of interest. For example, where administration of a molecule (for example, bacterial antigen) to an animal is known to generate a TH2 response (whether partial, predominant, or exclusive), the TH2 response in another animal may be reduced by presenting the molecule to the other animal in the context of a modified plant virus as described herein.

The terms "partial TH1 response" and "partial TH2 response" mean that the animal exhibits (a) TH1- and TH2-associated immunoglobulin, (b) TH1- and TH2-associated cytokine, and/or (c) TH1 and TH2 cell proliferation.

A "predominant TH2 response" is a partial TH2 response in which the level of any one or more of TH2-associated immunoglobulin, TH2-associated cytokine, and TH2 cell proliferation is statistically greater than the level of TH1-associated immunoglobulin, TH1-associated cytokine, and TH1 cell proliferation, respectively. In contrast, a "predominant TH1 response" is a partial TH1 response in which the level of any one or more of TH1-associated immunoglobulin, TH1-associated cytokine, and TH1 cell proliferation is statistically greater than the level of TH2-associated immunoglobulin, TH2-associated cytokine, and TH2 cell proliferation, respectively.

An "exclusive TH2 response" is a predominant TH2 response where the animal exhibits TH2-associated immunoglobulin, TH2-associated cytokine, and TH2 cell proliferation in the total absence of TH1-associated immunoglobulin, TH1-associated cytokine, and TH1 cell proliferation. Conversely, an "exclusive TH1 response" is a predominant TH1 response where the animal exhibits TH1-associated immunoglobulin, TH1-associated cytokine, and TH1 cell proliferation in the total absence of TH2-associated immunoglobulin, TH2-associated cytokine, and TH2 cell proliferation.

Furthermore, the invention's modified viruses are also useful where it is desirable to reduce an extant TH2 response in an animal. This is of particular use in applications where booster vaccinations follow a primary vaccination that employed an adjuvant that elicits an undesirable partial, predominant, or exclusive TH2 response. The prior art has noted that a pre-existing TH2 response cannot be overcome by booster application of adjuvant, which would otherwise result in a TH1 response when administered in the primary vaccination. Specifically, while using Quil-A as adjuvant resulted in induction of TH1 responses in mice when immunized with HPV 16 E7 protein, this effect was not seen when there was a pre-existing TH2 response to E7 (induced using algammulin as adjuvant) (Fernando et al. (1998) Scand. J. Immunol. 47:459). This observation indicates that where the primary vaccination of humans has been done with alum (which is the only adjuvant approved for human use and which induces TH2 responses), the resulting undesirable TH2 response that mediates undesirable allergic reactions may heretofore not be reversible. While primed TH2 cells, unlike TH1 cells, are stable and may not be directed toward the TH1 phenotype (Perez et al. (1995) Intl. Immunol. 7:869), it has been shown that in human T cell lines and clones generated from allergic patients, the use of the specific allergen conjugated to a bacterial protein results in the expansion of allergen-specific TH1/THO cells while the unconjugated allergen expanded TH2 cells (Jahn-Schmid et al. (1997) Intl. Immunol. 9:1867). Thus, the immunomodulatory dominance of the CPMV presentation of immunogens (including, but not limited to, allergens) can be extended to shift an established immune response from a deleterious TH2 pathway to a more beneficial TH1 pathway. Thus, the dominant immunomodulatory effect of the invention's modified plant viruses when used as the presentation platform for an antigen offers a means to overcome the extant TH2 response to that antigen that is initiated by the presence of a particular adjuvant.

The terms "reducing the level of TH2 response" and "reduced level of TH2 response" when made in reference to an animal's response to a modified virus containing a molecule of interest means that any one or more of the cellular and/or humoral response that is generated by TH2 lymphocytes upon stimulation by the molecule or the virus is reduced by any statistically significant amount as compared to the corresponding response in a control animal. In particular, a reduced level of a TH2 response in an animal that is exposed to a modified virus containing a molecule of interest refers to (a) a reduced level of TH2-associated immunoglobulin, (b) a reduced level of TH2-associated cytokine, and/or (c) a reduced proliferation level of TH2 cells.

The term "reduced level of TH2-associated immunoglobulin" in an animal that is exposed to a modified virus containing a molecule of interest refers to a reduction of, preferably from 0.1% to 100%, more preferably from 0.1% to 80%, and yet more preferably from 0.1% to 60%, in the quantity of one or more of the TH2-associated immunoglobulin subclasses (for example, mouse $IgG_1$, mouse $IgG_3$, human $IgG_2$, etc.), that is specific for either the molecule of interest or for the virus, relative to the quantity of total TH2-associated immunoglobulin of the same subclass. For example, a reduction of 10% in the quantity of molecule-specific (and/or virus-specific) mouse $IgG_1$ relative to the quantity of total mouse $IgG_1$ in the same mouse is considered a reduced level of TH2 response in the mouse. Similarly, a reduction of 0.1% in the quantity of molecule-specific (and/or virus-specific) mouse $IgG_3$ relative to the quantity of total mouse $IgG_3$ in the same mouse is considered a reduced level of TH2 response in the mouse.

Alternatively, the term "reduced level of TH2-associated immunoglobulin" in an animal that is exposed to a modified virus containing a molecule of interest refers to a reduction by preferably at least 2 fold, more preferably from 2 to 100,000 fold, yet more preferably from 2 to 10,000 fold, and most preferably from 2 to 2,000 fold, in the ratio of one or more of the TH2-associated immunoglobulin subclasses (for example, mouse $IgG_1$, mouse $IgG_3$, human $IgG_2$, etc.) that is specific for either the molecule of interest or for the virus, relative to the quantity of total TH2-associated immunoglobulin of the same subclass, on the one hand, relative to the ratio of the quantity of one or more of the TH1-associated immunoglobulin subclasses (for example, mouse $IgG_{2a}$, mouse $IgG_{2b}$, human $IgG_1$, human $IgG_3$, etc.) that is specific for either the molecule of interest or for the virus (respectively), relative to the quantity of total TH2-associated immunoglobulin of the same subclass, on the other hand. For example, a reduction of 1,000 fold in the ratio of molecule-specific (and/or virus-specific) mouse $IgG_1$:total $IgG_1$ relative to the ratio of molecule-specific (and/or virus-specific) mouse $IgG_{2a}$:total $IgG_{2a}$ in the same mouse is considered a reduced level of TH2 response in the mouse. Similarly, a reduction of 2,000 fold in the ratio of molecule-specific (and/or virus-specific) mouse $IgG_3$:total $IgG_3$ relative to the ratio of molecule-specific (and/or virus-specific) mouse $IgG_{2a}$:total $IgG_{2a}$ in the mouse is considered a reduced level of TH2 response in the mouse.

In a further alternative, the term "reduced level of TH2-associated immunoglobulin" in an animal that is exposed to a modified virus containing a molecule of interest refers to a reduction by preferably at least 2 fold, more preferably from 2 to 10,000 fold, even more preferably from 2 to 1,000 fold, and yet more preferably from 2 to 100 fold, in the geometric mean endpoint titer of molecule-specific (and/or virus-specific) TH2-associated immunoglobulins as compared to the geometric mean endpoint titer of the molecule-specific (and/or virus-specific) TH2-associated immunoglobulins in a control animal. For example, a reduction by 2 fold in the geometric mean endpoint titer of molecule-specific mouse $IgG_1$ in a treated mouse as compared to the geometric mean end-point titer of the molecule-specific mouse $IgG_1$ in a control mouse is considered a reduced level of TH2-associated immunoglobulin.

In yet another alternative, a "reduced level of TH2 response" refers to a reduced level of TH2-associated cytokine. The term "reduced level of TH2-associated cytokine" in an animal that is exposed to a modified virus containing a molecule of interest means that the amount of a TH2-associated cytokine that is produced by the animal's TH2 cells is reduced preferably by at least 2 fold, more preferably from 2 to 10,000 fold, yet more preferably from 2 to 1,000 fold, and most preferably from 1 to 100 fold, in a treated animal relative to the amount of TH2-associated cytokine that is produced by T cells of a control animal.

In a further alternative, a "reduced level of TH2 response" refers to a reduced proliferation level of TH2 cells. The term "reduced proliferation level of TH2 cells" in an animal that is exposed to a modified virus containing a molecule of interest means that the number of proliferating TH2 cells that are produced by the animal is reduced preferably by at least 2 fold, more preferably from 2 to 10,000 fold, more preferably from 2 to 1,000 fold, and most preferably from 1 to 100 fold, in the treated animal relative to number of proliferating T cells that are produced by a control animal. The number of proliferating T cells may be determined using methods such as those described herein, and their TH2 type may be determined by examination of supernatants of these cells for the presence of TH2-associated cytokines.

EXPERIMENTAL

The following Examples serve to illustrate certain preferred embodiments and aspects of the present invention and are not to be construed as limiting the scope thereof.

Unless otherwise stated, the experimental procedures and materials in each of the following Examples conform to the general descriptions listed below.

Experimental Animals

Female C57BL/6 (H-$2^b$, BALB/c (H-$2^d$), NIH(H-$2^q$), DBA/1(H-$2^5$) and Biozzi ABH(H-$2^{dq1}$) mice, aged 6-8 weeks, were housed at the Department of Pathology, University of Cambridge, United Kingdom. All procedures were performed according to the United Kingdom Home Office guidelines for animals in medical research.

Construction, Propagation and Purification of CVPs

The methods used for the expression of foreign peptides on both the S and L subunits of CPMV were as described in Porta et al. (1994) Virology 202:949. The various specific CVPs used in this investigation are described in Table 1.

TABLE 1

CVPs used for immunization

| CVP | Foreign sequence |
|---|---|
| CPMV-PAE5 | Amino acids 282-295 (NEYGVEGGRVNAVG; SEQ ID NO:21) of the outer membrane protein F (OM protein F) of *Pseudomonas aeruginosa* linked by S and G residues to residues 305-318 (NATAEGRAINRRVE; SEQ ID NO:22) of protein F on L subunit of CPMV |
| CPMV-MAST1 | Amino acids 1-30 of the fibronectin-binding (FnBP) of *Staphylococcus aureus*; GQNNGNQSFEEDTEKDKPKYEQGGNIIDID (SEQ ID NO:23) on the S subunit of CPMV |
| CPMV-HCG1 | C-terminal 37 amino acids of the β subunit of human chorionic gonadotrophin (βhCG-CTP37); TCDDPRFQDSSSSKAPPPSLPSPSRLPGPSDTPILPQ (SEQ ID NO:24) on the S subunit of CPMV |
| CPMV-HCG3 | Amino acids 109-118 and 132-145 from the C-terminus of βhCG (truncated form of the CTP37 peptide): TCDDPRFQDSSRLPGPSDTPILPQ (SEQ ID NO:25) on the S subunit of CPMV |
| CPMV-AGY2 | A 14 amino acid peptide (ELDVCVEEAEGEAP; SEQ ID NO:26) from the Cε4 extracellular segment of human mIgE on the S subunit of CPMV |
| CPMV-EGFR1 | The first 13 amino acids (LEEKKGNYVVTDH; SEQ ID NO:27) of the N-terminus of human mutant epidermal growth factor receptor variant III (EGFRvIII) on the S subunit of CPMV |
| CPMV-PARV09 | Amino acids 3-19 (DGAVQPDGGQPAVRNER; SEQ ID NO:28) from the 3L17 peptide derived from the VP2 protein of canine parvovirus on both the S and L subunits of CPMV |

ELISA to Determine Peptide-Specific and Total Isotype Concentrations

In some cases the $OD_{405}$ values reported in the examples that follow were converted into micrograms of antibody. Where this was done, the following procedure was used as the basis for the calculation: wells were coated with either goat anti-mouse IgG (Southern Biotechnologies Inc., USA) or with peptide. Serial dilutions of a known concentration of an $IgG_{2a}$ kappa mAB (Sigma-Aldrich, UK) were added to wells coated with anti-mouse IgG and dilutions of CVP-immunized sera were added to wells coated with either anti-mouse IgG or with peptide. The ELISA was carried out as reported elsewhere in the specification using the alkaline phosphatase (AP)-labeled anti-mouse $IgG_{2a}$ conjugate for detection. Byplotting the $OD_{405}$ obtained from the interaction of the goat anti-mouse IgG and monoclonal $IgG_{2a}$ against the known concentrations of $IgG_{2a}$, the $OD_{405}$ units of anti-peptide $IgG_{2a}$ in test serum were converted to micrograms of peptide-specific $IgG_{2a}$. An $OD_{405}$ was read at a suitable point on the $IgG_{2a}$ standard curve. Using the same standard curve, $OD_{405}$ units from sera incubated in wells coated with anti-IgG can be converted into micrograms of total $IgG_{2a}$ present in the serum sample. The percentage of peptide-specific $IgG_{2a}$ was calculated for each serum sample. The same method was utilized to measure total and peptide-specific $IgG_1$, $IgG_{2b}$ and $IgG_3$.

Statistics

Differences between groups were evaluated using the student's t-test where P<0.05 was considered statistically significant.

Example 1

DT- and KLH-conjugated Peptides do not Elicit Dominant TH1-type Serum Antibody Responses Any bias seen in the T helper pathway of an immune response generated by an antigen may be governed by the intrinsic immunological properties of the peptide concerned.

To test this, C57BL/6 mice were immunized with the CTP37 peptide, derived from human chorionic gonadotrophin, conjugated to diphtheria toxin (DT; Prof. V. Stevens, Ohio State University), or with a peptide (peptide 10) derived from an outer membrane protein (Omp F protein) of *Pseudomonas aeruginosa* conjugated to KLH (Prof. H. E. Gilleland, Louisiana State University). Both conjugates were inoculated in the presence of the adjuvant QS-21. Either two immunizations (on days 0 and 21) or three immunizations (on days 0, 14 and 28) were administered subcutaneously. Blood was collected by tail-bleeding or following exsanguination on day 42 and sera were collected and stored for later ELISA determinations at −20° C. For the detection of antibodies to *P. aeruginosa* OM protein F and PhCG-CTP37 (peptides were synthesized and purified by Genosys Inc., Cambridge, UK), microtiter plate wells were coated with 0.5 μg/well of the respective peptides (see Table 1, supra) for 3 h at 37° C. A series of doubling dilutions of serum were incubated on the antigen-coated plates for 1 h at 37° C. Bound antibody was detected with either alkaline phosphatase (AP)-conjugated goat anti-mouse $IgG_1$, $IgG_{2a}$, $IgG_{2b}$ or $IgG_3$ (Southern Biotechnologies Inc., USA) using p-nitrophenyl phosphate (PNPP, Sigma-Aldrich) as the substrate. These anti-mouse isotype reagents were first titrated against standard mouse myeloma proteins representing the four IgG subclasses and a dilution of 1:2000 of each conjugate gives less than 10% variation between myeloma binding. This was the dilution used in all subsequent assays. Endpoint titers were calculated as described previously (Brennan et al. (1999) Microbiol. 145:211; Brennan et al. (1999) J. Virol 73:930). The results are shown in Table 2.

TABLE 2

DT- and KLH-conjugated peptides do not elicit dominant TH1-type serum antibody responses

| Immunization schedule | | | | Mean peptide-specific titer ± SD | | | |
|---|---|---|---|---|---|---|---|
| Conjugate | Strain | Regimen[a] | Adjuvant | $IgG_1$ | $IgG_{2a}$ | $IgG_{2b}$ | $IgG_3$ |
| *DT-•HCG-CTP37 | C57BL/6 | 2 × 10 μg | QS-21 | 400661± | 141655± | 221702± | 43372± |
| KLH-OM protein F | C57BL/6 | 2 × 10 μg | QS-21 | 48337± | 7106± | 26210± | 1346± |

[a]Immunization of C57BL/6 mice used six animals/group.
*Sera were collected on day 29 and examined for βhCG-CTP37- and OM protein F-specific $IgG_1$, $IgG_{2a}$, $IgG_{2b}$ or $IgG_3$ by ELISA.

As shown in Table 2, both DT-βhCG-CTP37 and KLH-OM protein F elicited significantly higher levels of peptide-specific $IgG_1$ compared to $IgG_{2a}$ ($P<0.05$ and $P<0.01$ for DT-βhCG-CTP37 and KLH-OM protein F, respectively), demonstrating that presentation of these peptides on non-replicating vaccine carrier systems does not generate a bias towards a TH1-type response.

Example 2

Expression of Peptides on CPMV Overcomes a TH2 Bias in the Immune Response Stimulated by the Peptides on other Macromolecular Carrier Systems Leading to a TH1-type Response In contrast to the previous example, four peptides, including the two (DT-βhCG-CTP37 and KLH-OM protein F) from Example 1 were expressed on CPMV. Four groups of eight BALB/C mice were immunized subcutaneously in the presence of FIA/FCA in a total volume of 100 μl per dose. Three immunizations (on days 0 and 21 or on days 0, 14 and 28) were conducted by injecting, respectively, 100 μg, 25 μg and a further 25 μg of CVPs. Blood was collected by tail-bleeding or exsanguination on day 42; sera were collected and stored at −20° C.

For the detection of anti-CPMV antibody, wells were coated with 0.1 μg/well of CPMV for 3 h at 37° C. A series of doubling dilutions of serum were incubated on the antigenmated plates for 1 h at 37° C. Bound antibody was detected with either alkaline phosphatase (AP)-conjugated goat-anti-mouse $IgG_1$, $IgG_{2a}$, $IgG_{2b}$, or $IgG_3$ (Southern Biotechnologies Inc., USA) with p-nitrophenyl phosphate (PNPP) (Sigma-Aldrich) as the substrate. As before, these anti-mouse isotope reagents were first titrated against standard mouse myeloma proteins representing the four IgG subclasses. A dilution of 1:2000 of each conjugate gave less than 10% variation between myeloma binding; therefore, this dilution was used in all subsequent assays. Endpoint titers were calculated as described previously. For CPMV-specific titers, the results were expressed as endpoint titers, calculated as the inverse of the dilution that gives a mean $OD_{405}$ higher than the $OD_{405}$ obtained with a 1:50 dilution of pooled serum from unimmunized mice.

For peptide-specific titers, endpoint titers were the inverse of the dilution that gives a mean $OD_{405}$ higher than the $OD_{405}$ obtained with a 1:50 dilution of pooled serum from wild-type CPMV-immunized mice. The results are demonstrated in Table 3, rows 5 and 7.

TABLE 3

Isotype of peptide-specific serum IgG elicited by CVPs expressing a variety of different peptides

| Immunization schedule | | | | Mean peptide-specific titer ± SD | | | |
|---|---|---|---|---|---|---|---|
| Group. CVP[a] | Strain[b] | Regimen[c] | Adjuvant[d] | $IgG_1$ | $IgG_{2a}$ | $IgG_{2b}$ | $IgG_3$ |
| 1. AGY2+ | BALB/C | 100/25/25 | FCA/FICA | 793± | 10832± | 238± | 131± |
| 2. EGFR1 | DBA/1 | 3 × 100 μg | QS-21 | 405± | 10930± | 446± | NT |
| 3. PARVO9 | NIH | 2 × 100 μg | QS-21 | 346± | 26365± | 5157± | 412± |
| 4. PARVO9* | NIH | 2 × 100 μg | None | 372± | 14589± | 2579± | 313± |

TABLE 3-continued

Isotype of peptide-specific serum IgG elicited by CVPs expressing a variety of different peptides

| Immunization schedule | | | | Mean peptide-specific titer ± SD | | | |
|---|---|---|---|---|---|---|---|
| Group. CVP[a] | Strain[b] | Regimen[c] | Adjuvant[d] | $IgG_1$ | $IgG_{2a}$ | $IgG_{2b}$ | $IgG_3$ |
| 5. HCG1 | BALB/c | 100/25/25 | QS-21 | 498± | 14172± | 613± | 205± |
| 6. HCG3 | C57BL/6 | 100/25/25 | QS-21 | 499± | 21040± | 15116± | 919± |
| 7. PAE5 | C57BL/6 | 3 × 50 μg | QS-21 | 151± | 19751± | 4276± | 762± |
| 8. MAST1 | C57BL/6 | 2 × 5 μg | None | 2483± | 16890± | 44572± | 3553± |
| 9. MAST1 | C57BL/6 | 2 × 5 μg | Alum | 1426± | 10770± | 20770± | 357± |
| 10. MAST1 | C57BL/6 | 2 × 5 μg | QS-21 | 17704± | 162696± | 197958± | 5840± |
| 11. MAST1 | C57BL/6 | 2 × 5 μg | QS-21 | 1080± | 32650± | 39727± | 348± |
| 12. MAST1 | Biozzi | 3 × 10 μg | QS-21 | 200 | 1021± | 6552± | 87± |

Mouse strains[b] of different H-2 haplotypes were immunized[a] (5-9/group) subcutaneously or *intranasally with a number of CVPs[a] in either FCA/FICA, QS-21 or alum adjuvants or without adjuvant[d]. Sera were collected on day 42 (+day 83) and examined for mIgE-(AGY2), EGFRvIII-(EGFR1), VP2-(PARVO9), βhCG-CTP37-(HCG1), OM protein F-(PAE5) and FnBP-(MAST1)-specific-$IgG_1$, $IgG_{2a}$, $IgG_{2b}$, or $IgG_3$ by ELISA. Titers are expressed as geometric mean end-point titres ± SD.

Mouse strains[b] of different H-2 haplotypes were immunized[a] (5-9/group) subcutaneously or *intranasally with a number of CVPs[a] in either FCA/FICA, QS-21 or alum adjuvants or without adjuvant[d]. Sera were collected on day 42 (+day 83) and examined for mIgE-(AGY2), EGFRvIII-(EGFR1), VP2-(PARVO9), βhCG-CTP37-(HCG1), OM protein F-(PAE5) and FnBP-(MAST1)-specific-$IgG_1$, $IgG_{2a}$, $IgG_{2b}$, or $IgG_3$ by ELISA. Titers are expressed as geometric mean endpoint titers ±SD.

The term "endpoint titer" is that dilution of antibody that is specific for a given antigen and that is the highest dilution of the antibody that produces a detectable reaction when combined with the antigen.

As demonstrated by Table 3, in this case where epitopes were presented on CPMV, these epitopes elicited much lower levels of $IgG_1$ than $IgG_{2a}$, demonstrating a bias towards a TH1-type immune response. Indeed, in contrast to the two epitopes (that is, DT-PhCG-CTP37 and KLH-OM protein F), which were presented in the absence of CPMV presentation (Example 1), presentation of these same epitopes on CPMV elicited much lower levels of $IgG_1$ than $IgG_{2a}$.

Example 3

The Presentation of Peptides on CPMV Elicits a TH1-type Response in the Presence of Extraneous Immunomodulatory Agents, for Example, Specific Adjuvants Known to Favor TH2-type Immune Responses The adjuvant alum generally favors the induction of a TH2-type immune response. In order to determine whether the TH2-type immune response that is favored by adjuvants could be bypassed by the invention's CPMV presentation system, three groups of C57BL/6 mice were immunized subcutaneously on days 0 and 21 on each occasion with 5 μg CPMV-MAST1 (expressing a peptide derived from the fibronectin-binding protein of *Staphylococcus aureus*) either alone or with alum or QS-21. Sera were collected on day 42 and assayed for MAST1 peptide-specific immunoglobulins of the classes: $IgG_1$, $IgG_{2a}$, $IgG_{2b}$, or $IgG_3$ by ELISA, essentially as described in Examples 1 and 2, above. The titers indicated a strong bias towards a TH1 response in all three groups of mice including the control group in which no adjuvant was added (Table 3, supra, rows 8, 9 and 10). Thus, the immunomodulatory effect of adjuvants known to favor TH2 responses was completely bypassed by the presentation of peptides on chimeric CPMVs. Also, the absence of an extraneous adjuvant in part of this investigation serves to emphasize the intrinsic TH1-biasing effect of the CPMV platform itself (Table 3, supra, row 8).

Example 4

Peptides Derived from a Variety of Proteins Elicit Predominantly Peptide-specific TH1-type Antibodies in sera when Expressed on CPMV Independently of the Genetic Background of the Immunized Individual To verify the universal utility of CPMV as a carrier capable of producing a TH1-type response, and in order to demonstrate that the immunological effect was independent of the genetic constitution of an immunized individual, mice of different MHC Class II haplotypes were inoculated with CVPs expressing peptides derived from a number of different sources. CPMV-AGY2 (Table 3, row 1) expresses a peptide from the heavy chain of human membrane-bound immunoglobulin E (IgE); CPMV-EGFR1 (Table 3, row 2) expresses a peptide derived from protein, epithelial growth factor receptor, present on human cancer cells; CPMV-HCG3 (Table 3, row 6) express peptides derived from the human hormone, chorionic gonadotrophin (hCG); CPMV-PARVO9 (Table 3, rows 3 and 4) expresses a peptide from canine parvovirus, and CPMV-MAST1 (Table 3, rows 8-12) and CPMV-PAE5 (Table 3, row 7) express peptides derived from bacterial membrane proteins (of *S. aureus* and *P. aeruginosa*, respectively). Four mouse strains representative of different haplotypes (genotypes) were used: DBA/1 (H-2s); NIH (H-2s); C57BL/6; and Biozzi/ABH. Mice were immunized subcutaneously with the various CVPs in the presence of QS-21 (10 μg/dose; Aquila Biopharmaceutical Inc., Worcester, Mass.) in a total volume of 100 μl/dose. Either two immunizations on days 0 and 21 or three immunizations on days 0, 14 and 28 were administered (see Table 3, supra). Blood was collected by tail-bleeding or exsanguination on day 42 as above; sera were collected and stored at −20° C. For the detection of anti-CPMV antibody, wells were coated with 0.1 μg/well of CPMV for 3 h at 37° C. A series of doubling dilutions of serum were incubated on the antigen-coated plates for 1 h at 37° C. Bound antibody was detected with either alkaline phosphatase (AP)-conjugated goat anti-mouse $IgG_1$, $IgG_{2a}$, $IgG_{2b}$, or $IgG_3$ (Southern Biotechnologies Inc., USA) with p-nitrophenyl phosphate (PNPP) (Sigma-Aldrich) as the substrate.

These anti-mouse isotype reagents were first titrated against standard mouse myeloma proteins representing the four IgG subclasses. A dilution of 1:2000 of each conjugate gives less than 10% variation between myeloma binding. This dilution was used in all subsequent assays. Endpoint titers were calculated as above. For CPMV-specific titers, the results were expressed as endpoint titers, calculated as the inverse of the dilution that gives a mean $OD_{405}$ higher than the $OD_{405}$ obtained with a 1:50 dilution of pooled serum from unimmunized mice. For peptide-specific titers, endpoint titers were the inverse of the dilution that gives a mean $OD_{405}$ higher than the $OD_{405}$ obtained with a 1:50 dilution of pooled serum from wild-type CPMV-immunized mice.

All four constructs were shown to elicit high levels of peptide-specific $IgG_{2a}$ relative to levels of $IgG_1$ or $IgG_3$ ($P<0.01$ in all cases), despite the presence of a known TH2 immunomodulatory adjuvant (that is, QS-21 or alum). Levels of peptide-specific IgG, and $IgG_3$ were correspondingly much lower within all of the immunization groups (Table 3, supra). Some of the CVPs also produced significant quantities of peptide-specific $IgG_{2b}$. Where this occurred, the levels were lower than the levels of $IgG_{2a}$ with the exception of CPMV-MAST1, which in some cases elicited levels of $IgG_{2b}$ that were higher than levels of $IgG_{2a}$ (Table 3, supra). Thus, CVPs elicited predominantly peptide-specific TH1-type responses that appear to be influenced by neither the source nor sequence of the expressed peptide nor the presence of adjuvant with TH2 immunomodulatory potential.

Crucially, however, the CVPs in this experiment elicited TH1-type responses in mice of four different H-2 haplotypes. This indicated that the effect was not determined or governed by immune response genes (Ir genes). In other words, the genetic disposition of an individual was not an inhibiting factor in the ability of CPMV to elicit a TH1 bias in the immune response triggered by a particular peptide. It was especially significant that the effect of TH1 bias in an immune response was seen in Biozzi/ABH mice inoculated with CPMV-MAST1. Biozzi/ABH mice are genetically predisposed to favor a TH2-biased response, even before the potential biasing effects of extraneous adjuvants or of the peptides themselves were taken into account.

Hence, the CPMV-associated TH1 response was capable of overriding strong intrinsic genetic factors generally considered to govern to a significant extent the immune reaction of an individual. This was emphasized further by analysis of the specificity of immunoglobulins from TH1 and TH2 pathway subtypes. Less than 1% of $IgG_1$ produced was peptide-specific, compared with 25% to 100% of total $IgG_{2a}$ in all mice in the test group. In summary, the use of CPMV as a carrier and presentation system for peptides can overcome barriers at the level of the genetics of an individual, thereby providing a means to obviate vaccine-genomic considerations in the design of prophylactic and therapeutic agents.

Example 5

Presentation of Peptides on CPMV Particles Induces TH1-biased Immune Responses Over a Wide Range of Dosage Regimens It was apparent from a consideration of the IgG titration data in Table 3, supra, that higher levels of peptide-specific $IgG_{2a}$ (indicative of a TH1-type response) than of peptide-specific $IgG_1$ (indicative of a TH2-type response) were generated to several different antigens regardless of whether high or low doses (ranging from 300 μg CVPs down to 2 μg) were utilized in the immunization protocol. Thus, a further advantage of the immunomodulatory characteristics of CPMV as a carrier system was the lower amount of material that is required to elicit a desired type of response.

Example 6

CVPs Elicit a TH1-type Response Whether Presented Parenterally or Mucosally, Indicating that the Method of Particle Administration does not Affect the Nature of the Immune Response that was Stimulated NIH mice were immunized intranasally with CPMV-PARVO9, a CVP displaying a peptide derived from the VP2 protein of canine parvovirus. No adjuvant was used for this inoculation directly onto a mucosal surface (see Table 3, row 3). Two doses, each containing 100 μg of CVPs, were administered on days 0 and 14. On day 42, blood was collected essentially as described above and assayed for the presence of subclasses of immunoglobulins specific for the PARVO9 peptide (Table 3; supra, group 4). The concentration of peptide (VP2)-specific antibody was expressed as a percentage of the total antibody for each of the four isotypes within individual mice as shown in Table 4. Also, the mean percentage values for each of the four isotypes are shown in Table 4.

TABLE 4

Relative concentration of total and peptide-specific IgG isotypes in CVP-immunized mice

| | Mean total isotype concentration (μg/ml) | Mean peptide-specific isotype concentration (μg/ml) | % peptide-specific isotype of total isotype concentration |
|---|---|---|---|
| $IgG_1$ | 94.5 ± 40.7 | <0.004 μg | <0.004% |
| $IgG_{2a}$ | 135.0 ± 9.7 | 8.9 ± 3.9 μg | 6.6% |
| $IgG_{2b}$ | 96.5 ± 17.9 | 4.7 ± 3.1 μg | 4.9% |
| $IgG_3$ | 44.0 ± 14.3 | <0.004 μg | <0.004% |

Although high levels of total $IgG_1$ and $IgG_3$ (which were almost exclusively CPMV specific) were detected, the total concentrations of $IgG_{2a}$ and $IgG_{2b}$ were also high. Furthermore, significant proportions were peptide-specific (Table 4, supra), highlighting again the bias in the responses towards the TH1 type and the fact that such a response can be elicited regardless of the route of administration of the antigen presented on CPMVs.

Example 7

Use of a Chimeric Virus Particle-containing Immunogenic Complex to Alter the Nature of an Extant Immune Response There are situations in which particular antigens are presented as vaccines in the presence of adjuvants that elicit a predominantly TH2-type response. Indeed, the approval to date of only alum (which elicits predominantly a TH2-type immune response) as an adjuvant that is considered safe for human vaccine applications indicates that many vaccines that will become available will contain, a priori, a factor that elicits a TH2-type immune response with adverse side effects. This emphasizes the need for immunomodulation of a response towards the TH1 pathway and away from the TH2 pathway induced in such circumstances. Since many vaccines require multiple inoculations to be effective, it is possible to address the issue of altering a TH2 response (that is associated with a given peptide in a subunit vaccine) in favor of a TH1-type response by boosting the initial response with a formulation containing a CPMV-presented peptide. The strength of the immunomodulatory dominance of the CPMV platform bypasses the TH2 pathway potential of the adjuvant, while still achieving the required boosting of the immune response to the peptide in question.

To demonstrate this, mice are immunized with MAST1 protein (Table 1) in the presence of alum and/or QS-21 adjuvants to induce a TH2 response as determined by protein-specific IgG levels. Test mice are subsequently immunized with CPMV-MAST1, with control mice receiving no subsequent immunization. IgG levels in the test and control mice are determined as described supra. An increase in the ratio of peptide-specific $IgG_1:IgG_{2a}$, $IgG_3:IgG_{2a}$, $IgG_1:IgG_{2b}$, and/or $IgG_3/IgG_{2b}$ in the test animals relative to the control animals demonstrates that the chimeric viruses of the invention overcome the TH2 response that is induced by the adjuvant in the primary immunization.

Example 8

The Use of CPMV Virus Particles Engineered to Express and Present Chemically Reactive Peptides to Conjugate Immunogenic Proteinaceous and Non-proteinaceous Moieties, Especially Carbohydrate Moieties Deoxyribonucleotides encoding the amino acid sequence with the formula DEGKGKGKGKDE (SEQ ID NO:29) are cloned into the vector pCP2 corresponding to a cDNA copy of the RNA2 molecule of CPMV. The insertion is made such that the reactive peptide is inserted into the βB-βC loop of VP-S (the smaller of the two CPMV virus coat proteins) between alanine 22 and proline 23 as previously described (U.S. Pat. Nos. 5,958,422 and 5,874,087; each of which is incorporated herein in its entirety by this reference). Purified carbohydrates are chemically conjugated to reactive lysine residues in the peptide and the resulting carbohydrate-conjugated CVPs are purified by affinity-chromatography using, for example, a carbohydrate-specific antibody or by DEAE-cellulose chromatography. Carbohydrate-conjugated CVPs are inoculated into mice following essentially the same immunization regimen as described in Examples 2 and 3 above. Tail bleeds are taken on day 42 and the sera assayed for IgG subclasses specific for the carbohydrate. A predominance of TH1-response IgG subclasses is seen consistent with the immunomodulatory dominance of CPMV.

Example 9

CVPs Prime Predominantly CPMV- and Peptide-specific $IgG_{2a}$- and $IgG_{2b}$-producing B Cells in Spleen as Determined by ELISPOT Spleen cells from CPMV-MAST1 (Table 3, row 10) in QS-21 immunized mice were pooled and the red blood cells removed by cold lysis in 0.8% $NH_4Cl$. The cells were washed twice with RPMI 1640, counted and resuspended at concentrations of either $5\times10^6$, $5\times10^5$ or $5\times10^4$ viable cells/ml. Each cell suspension (100 µl/well) was added to the wells of 96-well MultiScreen Immobilon IP plates (Millipore, Billerica, MA), which were precoated overnight at 4° C. with either CPMV or FnBP peptide in sterile carbonate buffer, pH 9.6, and blocked with RPMI 1640 containing 10% FCS for one hour at 37° C. Negative control wells were coated only with buffer or with an irrelevant control peptide. The cells were incubated on the plates for 20 h at 37° C. and then washed three times with PBS. Bound antibody was detected with the appropriate alkaline phosphatase (AP)-conjugated goat anti-mouse $IgG_1$, $IgG_{2a}$, $IgG_{2b}$, or $IgG_3$ (Southern Biotechnologies Inc., USA). After two hours at 37° C., the plates were washed four times with PBST, and streptavidin-peroxidase (100 µl/well) was added for 30 minutes at 37° C. Following washing with PBST, SIGMA FAST™ DAB (3,3'-diaminobenzidine tetrahydrochloride) substrate was added (100 µl/well) until maximal color intensity developed. Plates were washed gently with tap water, dried for 30 minutes at 37° C., and the spots counted using a dissection microscope (Nikon SMZ-1). The results were expressed as mean spot-forming cells (SFC) per 106 spleen cells (SFC/$10^6$ spleen cells) ±SD for both CPMV and peptide, as shown in Table 5.

TABLE 5

CVPs prime predominantly CPMV and peptide-specific $IgG_{2a}$ and $IgG_{2a}$-producing B cells in spleen

|  | $IgG_1$ | $IgG_{2a}$ | $IgG_{2b}$ | $IgG_3$ |
|---|---|---|---|---|
| [a]Mean CPMV-specific titer ± SD | 22200± | 666555± | 921600± | 13000± |
| [b]Mean No. CPMV-specific SFC/$10^6$ spleen cells ± SD | 2 ± 3 | 240 + 6.8 | 44 ± 15 | 0.3 ± 0.8 |
| [a]Mean peptide-specific titer ± SD | 17704± | 162696± | 197958± | 5840± |
| [b]Mean No. peptide-specific SFC/$10^6$ spleen cells ± SD | 0.6 ± 1 | 41 ± 8.3 | 13 ± 3.7 | 0.3 ± 0.8 |

[a]C57BL/6 mice were immunized subcutaneously with CPMV-MAST1 in QS-21 (Table 3, row 10). Sera were collected on day 42 and examined for CPMV- and FnBP-specific $IgG_1$, $IgG_{2a}$, $IgG_{2b}$ or $IgG_3$ by ELISA. Titers are expressed as geometric mean end-point titer ± SD.

[b]Spleen cells were pooled and examined for the presence of CPMV- and FnBP-specific $IgG_1$, $IgG_{2a}$, $IgG_{2b}$ or $IgG_3$- producing SFC by ELISPOT. The results are expressed as arithmetic mean number of SFC/$10^6$ spleen cells ± SD.

ELISPOT analysis of immunoglobulins elicited by CPMV-MAST1 in QS-21 showed similarly high numbers of $IgG_{2a}$ and $IgG_{2b}$ spot-forming cells in the spleens of the immunized mice in contrast with the much lower numbers of $IgG_1$ and $IgG_3$ SFCs (Table 5). There were approximately 4-fold higher titers of CPMV-specific $IgG_{2a}$ and $IgG_{2b}$ antibody and SFCs compared to peptide (FnBP)-specific antibody and SFC in these mice (Table 5). Interestingly, although levels of FnBP-specific $IgG_{2a}$ and $IgG_{2b}$ in sera were very similar, much higher numbers of $IgG_{2a}$-producing SFCs than $IgG_{2b}$-producing SFCs were detected in spleen by ELISPOT (Table 5), suggesting that CPMV-MAST1 primes a larger number of FnBP-specific $IgG_{2a}$-producing B cells. Thus, C57BL/6 mice immunized with CPMV-MAST1 elicited very high concentrations of predominantly CPMV-specific $IgG_{2a}$ and $IgG_{2b}$ in serum, with lower but significant levels of CPMV-specific $IgG_1$ and $IgG_3$ (Table 5).

Example 10

CPMV-specific T Cells in Spleen Primed by CVPs Proliferate to Produce IFN-γ (a TH1-associated Cytokine), not IL-4 (a TH2-associated Cytokine)

Spleens from mice immunized with CVPs were removed 42 days after primary immunization and single-cell suspensions were made. Following washing and lysis of red blood cells with ice-cold 0.85% $NH_4Cl$, the splenocytes from five mice were pooled and dispensed into round-bottomed 96-well plates ($2\times10^5$/100 μl; Nunclon Delta Surface, Nunc, Denmark) in RPMI 1040 medium (Gibco, Paisley, UK) containing 1 mM L-glutamine, 10 mM penicillin/streptomycin and 10% fetal calf serum (FCS). Cells were cultured with 2.5 μg/ml concanavalin A (ConA, Sigma-Aldrich) or wild-type CPMV (50 or 5 μg/ml) for five days at 37° C. in 5% $CO_2$. In the last 12 hours of culture, 0.5 μCi/well of (methyl-3H) thymidine (G.E. Healthcare) were added. Cells were harvested onto filter mats (Wallac Oy, Turku, Finland) and incorporation of label measured using a 1450 Microbeta Trilux liquid scintillation and luminescence counter (Wallac). Data were expressed as stimulation indices, where counts per minute in the presence of adjuvant were divided by counts measured in the absence of antigen (medium only). A value of 3 or greater was considered significant. Spleen cells from mice immunized with CPMV-MAST1 proliferated very strongly in vitro to stimulation with even low concentrations (5 μg/ml) of CPMV, indicating a highly specific T cell induction mediated by the peptide carrier.

Pooled spleen cells were subsequently cultured alone or with either ConA (2.5 μg/ml) or wild-type CPMV (50 or 5 μg/ml) in 24-well plates ($5\times10^6$/well in 2 ml volume). After 48 h, 0.5 ml of cell culture supernatant were collected into Eppendorf tubes and stored at −80° C. The supernatants were tested for the presence of both IFN-γ and IL-4 by ELISA essentially as described above. Briefly, 96-well ELISA plates (Immulon-4) were coated overnight with 2 μg/well of either rat mAb anti-mouse IFN-γ or rat mAb anti-mouse IL-4 (both Pharmingen, San Diego, Calif.) at 4° C. After blocking of the plates with PBS containing 0.05% TWEEN® and 5% BSA, serial dilutions of mouse spleen cell culture supernatant were added to the wells. As controls, dilutions of recombinant mouse IFN-γ and IL-4 (Pharmingen), starting at 4 ng/ml and 15 ng/ml for IL-4 and IFN-γ, respectively, were added. After one hour at 37° C., bound cytokine was detected using biotinylated rat anti-mouse IFN-γ or anti-IL-4 mAbs (both Pharmingen) for one hour at 37° C. These mAbs recognize different epitopes on IFN-γ and IL-4 than the mAbs used for the capture step earlier in the procedure. Streptavidin peroxidase (Sigma-Aldrich; 2 μg/ml) was added for 30 minutes at 37° C. followed by O-phenylenediamine dihydrochloride (OPD) substrate (1 mg/ml). After 30 minutes at 37° C., the reaction was stopped by the addition of 50 μl/well 2.5 $MH_2SO_4$, and the absorbance read at 492 nm using an automated Anthos HT II ELISA plate reader. The results are shown in Table 6.

TABLE 6

CPMV stimulates proliferation and cytokine production by spleen cells of the TH1 phenotype

| Antigen | [a]Mean CPM ± SD | [b]SI | [c]Mean IFN-γ concentration ± SD | [d]Mean IL-4 concentration ± SD |
|---|---|---|---|---|
| | | (A) | | |
| None | 520 ± 160 | — | 0.21 ng/ml | 0.04 ng/ml |
| CPMV | 13381 ± 2143 | 25.7 | 19.24 ng/ml | 0.04 ng/ml |
| ConA | 11442 ± 1383 | 22.0 | 10.70 ng/ml | 0.10 ng/ml |
| | | (B) | | |
| None | 384 + 184 | — | NT | NT |
| CPMV | 316 ± 79 | 0.82 | 0.239 ng/ml | 0.04 ng/ml |
| ConA | 9333 ± 3559 | 24.3 | NT | NT |

[a,b]C57BL/6 mice are immunized subcutaneously with CPMV-MAST1 in QS-21 (Table 3, row 10). Spleen cells from these mice (A) and from unimmunized mice (B) were pooled and cultured for 5 days either alone or with 2.5 μg/ml ConA or 50 μg/ml CPMV. T cell proliferation is expressed both as mean CPM ± SD[a] and SI[b].
[c,d]The supernatants from these cultures were also examined for the presence of IFN-γ[c] and IL-4[d] protein by ELISA. The results are expressed as arithmetic mean ng/ml ± SD. (NT = not tested).

The supernatants from these proliferating cells were shown to contain high levels of IFN-γ and low or undetectable levels of IL-4 (Table 6A). Unimmunized mice by comparison contain no CPMV-specific antibody or SFC (not shown) and do not proliferate, nor do they produce IFN-γ or IL-4 in response to CPMV stimulation (Table 6B).

Example 11

Conjugation of Peptides

In this example, a chimeric plant virus in accordance with the invention is engineered to express a reactive peptide that contains a cysteine residue and that is capable of conjugating with any peptide that has been activated using n-maleimidobenzoyl-N-hydroxysuccinimide ester ("MBS" available from Pierce).

Deoxyribonucleotides encoding the amino acid sequence with the formula Arg-Glu-Arg-Glu-His-Cys (SEQ ID NO:30) are cloned into the vector pCP2 corresponding to a cDNA copy of the RNA2 molecule of CPMV. The insertion is made such that the reactive peptide is inserted into the βB-βC loop of VP-S (the smaller of the two CPMV virus coat proteins) between alanine 22 and proline 23 as previously described (U.S. Pat. Nos. 5,958,422 and 5,874,087; each of which is incorporated herein in its entirety by this reference).

The protein molecule of interest that is sought to be conjugated to the invention's plant virus is activated using MBS as follows. The protein is dissolved in buffer (for example, 0.01 M $NaPO_4$, pH 7.0) to a final concentration of approximately 20 mg/ml. At the same time, MBS is dissolved in N,N-dimethyl formamide to a concentration of 5 mg/ml. The MBS solution, 0.51 ml, is added to 3.25 ml of the protein solution and incubated for 30 minutes at room temperature with stirring every 5 minutes. The resulting MBS-activated protein is then purified by chromatography on a BIO-GEL® P-10 column (Bio-Rad; 40 ml bed volume) equilibrated with 50 mM $NaPO_4$, pH 7.0 buffer. Peak fractions are pooled (6.0 ml).

The chimeric plant virus expressing Arg-Glu-Arg-Glu-His-Cys (SEQ ID NO:30) (20 mg) is added to the MBS-activated protein solution, stirred until the peptide is dissolved and incubated three hours at room temperature. Within 20 minutes, the reaction mixture becomes cloudy and precipitates are formed. After three hours, the reaction mixture is centrifuged at 10,000×g for 10 minutes and the supernatant analyzed for protein content. The conjugate precipitate is washed three times with PBS and stored at 4° C. The resulting purified protein-conjugated CVPs are inoculated into mice following essentially the same immunization regimen as described in Examples 2 and 3 above. Tail bleeds are taken on day 42 and the sera assayed for IgG subclasses specific for the carbohydrate. A predominance of TH1 response IgG subclasses is seen consistent with the immunomodulatory dominance of CPMV.

From the above, it is clear that the invention provides methods and compositions that are effective in modulating the nature and/or level of an immune response to any molecule of interest exemplified by, but not limited to, an antigen or immunogen. In particular, data presented herein demonstrates that the invention provides methods and means for effecting a TH1 bias in the immune response to molecules such as antigens or immunogens, and/or reducing a TH2 bias in the immune response to such molecules. More particularly, the above shows that invention provides methods and means for increasing a TH1 immune response that is directed against molecules that otherwise generally stimulate a TH2-type response. From the above, it is also evident that the invention further provides compositions and methods to reduce a TH2 immune response to molecules. The above additionally shows that the invention furnishes compositions and methods for altering (that is, increasing or decreasing) the level of TH1- and TH2-associated immunoglobulins, the level of proliferation of TH1- and TH2-associated cytokines, and the level of proliferation of TH1 and TH2 cells.

All publications and patents mentioned in the above specification were herein incorporated by reference. Various modifications and variations of the described methods and system of the invention will be apparent to those skilled in the art without departing from the scope and spirit of the invention. Although the invention has been described in connection with a specific preferred embodiment, it should be understood that the invention as claimed should not be unduly limited to such specific embodiment. Indeed, various modifications of the described modes for carrying out the invention that are obvious to those skilled in the art and in fields related thereto are intended to be within the scope of the following claims.

The following useful plant viral vectors are on deposit at the American Type Culture Collection (ATCC), Manassa, VA, USA, under the terms of the Budapest Treaty on the International Recognition of the Deposit of Microorganisms for the Purposes of Patent Procedure and Regulations thereunder: pTB2 (ATCC No. 75280) and pTBU5 (ATCC No 75281). The construction details for these plasmids are set forth in U.S. Pat. No. 5,589,367, hereby incorporated herein by this reference.

What is claimed is:

1. A process for producing a virus-like particle comprising:

providing a plant virus expressing a heterologous peptide on an exposed portion of a coat protein of said plant virus, which is capable of conjugating to a peptide of interest, wherein said plant virus is a cowpea mosaic virus (CPMV), and wherein said heterologous peptide comprises one or more acidic amino acids and an equal number of basic amino acids; and conjugating said peptide of interest to said heterologous peptide to generate a conjugate.

2. The process of claim 1, wherein conjugating said peptide of interest comprises chemically conjugating said peptide of interest.

3. The process of claim 1, wherein said peptide of interest is an antigen of a source selected from the group consisting of an animal pathogen and a cancer cell.

4. The process of claim 1, wherein said acidic amino acids are selected from aspartic acid, glutamic acid, and cysteine, and said basic amino acids are selected from lysine, arginine, and histidine.

5. The process of claim 1, wherein said heterologous peptide comprises a sequence of contiguous charged amino acids selected from a first sequence consisting of contiguous acidic amino acids and a second sequence consisting of contiguous basic amino acids.

6. The process of claim 5, wherein said sequence of contiguous charged amino acids occurs in said heterologous peptide as a repeating sequence.

7. The process of claim 5, wherein said heterologous peptide comprises said first and second sequences, and wherein said first sequence is contiguous with said second sequence.

8. The process of claim 7, wherein said contiguous first and second sequences occur in said heterologous peptide as a repeating sequence.

9. The process of claim 1, wherein said heterologous peptide comprises Asp-Glu-Gly-Lys-Gly-Lys-Gly-Lys-Gly-Lys-Asp-Glu listed as SEQ ID NO :29.

10. The process of claim 1, wherein said conjugate is immunogenic.

11. A process for producing a virus-like particle comprising:

providing a plant virus containing a polynucleotide encoding a heterologous peptide that is expressed on an exposed portion of a coat protein of said plant virus, said heterologous peptide being capable of conjugating to a peptide of interest, wherein said plant virus is a comovirus, and wherein said heterologous peptide comprises one or more acidic amino acids and an equal number of basic amino acids;

infecting a host cell with said plant virus; and allowing replication and expression of said polynucleotide in the host cell.

12. The process of claim 11, wherein said acidic amino acids are selected from aspartic acid, glutamic acid, and cysteine, and said basic amino acids are selected from lysine, arginine, and histidine.

13. The process of claim 11, wherein said heterologous peptide comprises a sequence of contiguous charged amino acids selected from a first sequence consisting of contiguous acidic amino acids and a second sequence consisting of contiguous basic amino acids.

14. The process of claim 13, wherein said sequence of continuous charged amino acids occurs in said heterologous peptide as a repeating sequence.

15. The process of claim 13, wherein said heterologous peptide comprises said first and second sequences, and wherein said first sequence is contiguous with said second sequence.

16. The process of claim 15, wherein said contiguous first and second sequences occur in said heterologous peptide as a repeating sequence.

17. The process of claim 11, wherein said heterologous peptide comprises Asp-Glu-Gly-Lys-Gly-Lys-Gly-Lys-Gly-Lys-Asp-Glu listed as SEQ ID NO:29.

18. The process of claim 11, wherein said plant virus is a cowpea mosaic virus (CPMV).

* * * * *